US010053454B2

(12) United States Patent
Poss et al.

(10) Patent No.: US 10,053,454 B2
(45) Date of Patent: Aug. 21, 2018

(54) CARBAZOLE COMPOUNDS USEFUL AS BROMODOMAIN INHIBITORS

(71) Applicant: Bristol-Myers Squibb Company, Princeton, NJ (US)

(72) Inventors: Michael A. Poss, Lawrenceville, NJ (US); David R. Tortolani, Skillman, NJ (US); Ashok Vinayak Purandare, Pennington, NJ (US); John S. Tokarski, Princeton, NJ (US); Christopher P. Mussari, Princeton, NJ (US); Muthoni G. Kamau, Lawrenceville, NJ (US); Dharmpal S. Dodd, Princeton, NJ (US); Ashvinikumar V. Gavai, Princeton Junction, NJ (US); Daniel O'Malley, New Hope, PA (US); Tram N. Huynh, Pennington, NJ (US); Wayne Vaccaro, Yardley, PA (US); Lalgudi S. Harikrishnan, Skillman, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/770,230

(22) PCT Filed: Feb. 27, 2014

(86) PCT No.: PCT/US2014/018914
§ 371 (c)(1),
(2) Date: Aug. 25, 2015

(87) PCT Pub. No.: WO2014/134267
PCT Pub. Date: Sep. 4, 2014

(65) Prior Publication Data
US 2016/0009701 A1    Jan. 14, 2016

Related U.S. Application Data

(60) Provisional application No. 61/770,021, filed on Feb. 27, 2013.

(51) Int. Cl.
| | | |
|---|---|---|
| C07D 413/04 | (2006.01) |
| C07D 413/10 | (2006.01) |
| C07D 413/14 | (2006.01) |
| C07D 417/14 | (2006.01) |
| A61K 31/422 | (2006.01) |
| A61K 31/427 | (2006.01) |
| A61K 31/4439 | (2006.01) |
| A61K 31/454 | (2006.01) |
| A61K 31/5355 | (2006.01) |
| A61K 31/5377 | (2006.01) |
| A61K 31/541 | (2006.01) |
| A61K 31/553 | (2006.01) |

(52) U.S. Cl.
CPC .......... *C07D 413/10* (2013.01); *A61K 31/422* (2013.01); *A61K 31/427* (2013.01); *A61K 31/4439* (2013.01); *A61K 31/454* (2013.01); *A61K 31/5355* (2013.01); *A61K 31/5377* (2013.01); *A61K 31/541* (2013.01); *A61K 31/553* (2013.01); *C07D 413/04* (2013.01); *C07D 413/14* (2013.01); *C07D 417/14* (2013.01)

(58) Field of Classification Search
CPC .. C07D 413/04; C07D 413/10; C07D 413/14; C07D 417/14
See application file for complete search history.

(56) References Cited

U.S. PATENT DOCUMENTS

| | | | |
|---|---|---|---|
| 8,815,840 B2* | 8/2014 | Purandare | C07D 209/88 514/210.21 |
| 9,708,311 B2 | 7/2017 | Peters et al. | |
| 2003/0129448 A1 | 7/2003 | Lin et al. | |
| 2012/0058988 A1* | 3/2012 | Purandare | C07D 209/88 514/210.21 |
| 2012/0071668 A1 | 3/2012 | Suzuki et al. | |
| 2013/0026426 A1 | 1/2013 | Harada et al. | |

FOREIGN PATENT DOCUMENTS

| | | |
|---|---|---|
| CN | 102167913 B | 9/2013 |
| JP | 54-5433 | 1/1979 |
| WO | WO2010/080474 A1 | 7/2010 |
| WO | WO2014/134232 A1 | 9/2014 |
| WO | WO2015/100282 A1 | 7/2015 |

OTHER PUBLICATIONS

Hewlins, Michael et al., "Exploratory Routes to Carbazole Derivatives Prelusive to 6H-Pyrido[4,3-b] carbazole synthesis". Journal of Chemical Research, vol. 8, pp. 2645-2696 (1986).
Kikugawa, Yasuo et al., "Synthesis of Carbazoles from N-(N,N-Diarylamino)phthalimides with Aluminum Chloride via Diarylnitrenium Ions", Journal of Organic Chemistry, vol. 66, pp. 8612-8615 (2001).
Norris, et al., U.S. Appl. No. 62/159,991, filed May 12, 2015.
Quesnelle, et al., U.S. Appl. No. 62/159,497, filed May 11, 2015.
Han, et al., U.S. Appl. No. 62/159,996, filed May 12, 2015.
Lyakhova, Ekaterina G., "Bromine-containing alkaloids from the marine sponge *penares* sp.", Tetrahedron Letters, 2012, vol. 53, pp. 6119-6122.

\* cited by examiner

*Primary Examiner* — Rebecca L Anderson
(74) *Attorney, Agent, or Firm* — Elliott Korsen

(57) ABSTRACT

The present invention is directed to carbazole compounds, pharmaceutically acceptable compositions comprising compounds of the invention and methods of using the compositions in the treatment of various disorders.

5 Claims, No Drawings

SEQUENCE LISTING

```
<160> NUMBER OF SEQ ID NOS: 3

<210> SEQ ID NO 1
<211> LENGTH: 21
<212> TYPE: PRT
<213> ORGANISM: Tobacco vein mottling virus

<400> SEQUENCE: 1

Met Gly Ser Ser His His His His His His Ser Ser Gly Glu Thr Val
1               5                   10                  15

Arg Phe Gln Ser Met
            20

<210> SEQ ID NO 2
<211> LENGTH: 39
<212> TYPE: PRT
<213> ORGANISM: Tobacco vein mottling virus

<400> SEQUENCE: 2

Met Gly Ser Ser His His His His His His Ser Ser Gly Glu Thr Val
1               5                   10                  15

Arg Phe Gln Gly Leu Asn Asp Ile Phe Glu Ala Gln Lys Ile Glu Trp
            20                  25                  30

His Glu Asp Thr Gly His Met
        35

<210> SEQ ID NO 3
<211> LENGTH: 21
<212> TYPE: PRT
<213> ORGANISM: Artificial Sequence
<220> FEATURE:
<223> OTHER INFORMATION: Biotinylated histone peptide
<220> FEATURE:
<221> NAME/KEY: MOD_RES
<222> LOCATION: (5)..(5)
<223> OTHER INFORMATION: ACETYLATION
<220> FEATURE:
<221> NAME/KEY: MOD_RES
<222> LOCATION: (8)..(8)
<223> OTHER INFORMATION: ACETYLATION
<220> FEATURE:
<221> NAME/KEY: MOD_RES
<222> LOCATION: (12)..(12)
<223> OTHER INFORMATION: ACETYLATION
<220> FEATURE:
<221> NAME/KEY: MOD_RES
<222> LOCATION: (16)..(16)
<223> OTHER INFORMATION: ACETYLATION
```

```
<400> SEQUENCE: 3

Ser Gly Arg Gly Lys Gly Gly Lys Gly Leu Gly Lys Gly Gly Ala Lys
1               5                   10                  15

Arg His Arg Lys Val
                20
```

CARBAZOLE COMPOUNDS USEFUL AS BROMODOMAIN INHIBITORS

FIELD OF THE INVENTION

The invention relates to compounds, pharmaceutical compositions comprising the compounds and to their use in therapy.

BACKGROUND OF THE INVENTION

The genomes of eukaryotic organisms are highly organized within the nucleus of the cell. The long strands of duplex DNA are wrapped around an octomer of histone proteins to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. There has been appreciation recently that chromatin templates form a fundamentally important set of gene control mechanisms referred to as epigenetic regulation. By conferring a wide range of specific chemical modifications to histones and DNA (such as acetylation, methylation, phosphorylation, ubiquitinylation and SUMOylation) epigenetic regulators modulate the structure, function and accessibility of our genome, thereby exerting a huge impact in gene expression.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell. The BET family of bromodomain containing proteins comprises 4 proteins (BRD2, BRD3, BRD4 and BRD-T) which contain tandem bromodomains capable of binding to two acetylated lysine residues in close proximity, increasing tile specificity of the interaction.

BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-I3 complex to inducible genes, resulting in phosphorylation of RNA polymerase and increased transcriptional output (Hargreaves et al, Cell, 2009 138(1): 1294145). All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Recent articles relating to this target include Prinjha et al., Trends in Pharmacalogical Sciences, March 2012, Vol. 33, No. 3, pp. 146-153; Conway, ACS Med. Chem. Lett., 2012, 3, 691-694 and Hewings et al., J. Med. Chem., 2012, 55, 9393-9413.

Small molecule BET inhibitors that are reported to be in development include GSK-525762A, OTX-015 as well as others from the University of Oxford and Constellation Pharmaceuticals Inc.

Hundreds of epigenetic effectors have been identified, many of which are chromatin-binding proteins or chromatin-modifying enzymes. These proteins have been associated with a variety of disorders such as neurodegenerative disorders, metabolic diseases, inflammation and cancer. Thus, these compounds which inhibit the binding of a bromodomain with its cognate acetylated proteins, promise new approaches in the treatment of a range of autoimmune and inflammatory diseases or conditions and in the treatment of various types of cancer.

SUMMARY OF THE INVENTION

In a first aspect of the present invention, there is provided a compound of formula (I)

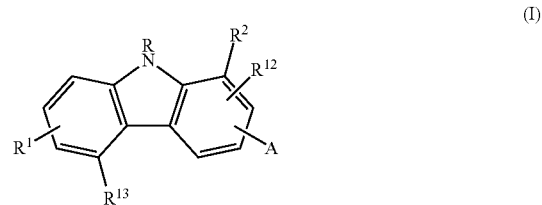

(I)

wherein:

A is optionally substituted heteroaryl, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-$SO_2$—, optionally substituted $(C_1-C_6)$alkyl-$SO_2$—, optionally substituted $(C_3-C_8)$cycloalkyl-$SO_2$—, optionally substituted heteroaryl-$SO_2$—, optionally substituted $(C_1-C_6)$alkyl-OCO— or optionally substituted $(C_3-C_8)$cycloalkyl-OCO—;

$R^1$ is halogen, —CN, OH, —$NR^3R^4$, —$CONR^3R^4$, —COOH, —$OCONR^3R^4$, —$NHOCOR^7$, —$NHCONR^7R^8$, —$NHSO_2NR^7R^8$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl-CO—, optionally substituted $(C_3-C_8)$cycloalkyl-$SO_2$—, optionally substituted aryl $(C_1-C_6)$ alkoxy, optionally substituted $(C_3-C_8)$cycloalkyl $(C_1-C_6)$ alkoxy, optionally substituted heterocyclyl-CO—, optionally substituted heterocyclyl, optionally substituted $(C_1-C_6)$alkyl-$SO_2$—, —$NHSO_2$-optionally substituted $(C_1-C_6)$alkyl, —$NHSO_2$-optionally substituted heterocyclo, optionally substituted $(C_1-C_6)$alkyl-$NHSO_2$— or optionally substituted heterocyclo-$NHSO_2$—;

$R^2$ is H, halogen, —CN, —COOH, —$CONR^7R^8$, —$OCONR^3R^4$, —$NHSO_2R^7$, —$NHCOR^7$, —$NHCOOR^7$, optionally substituted $(C_1-C_6)$alkyl, optionally substituted $(C_2-C_6)$alkynyl, optionally substituted $(C_1-C_6)$alkoxy, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, R⁴ is hydrogen, optionally substituted (C₁-C₆)alkyl or optionally substituted (C₃-C₈)cycloalkyl;

or R³ and R⁴ may be taken together with the nitrogen atom to which they are attached to form an optionally substituted (C₂-C₈) heteroaryl or (C₂-C₈) heterocyclic ring;

R⁷ and R⁸ are independently hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy (C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl(C₁-C₆)alkyl;

or R⁷ and R⁸ may be taken together with the nitrogen atom to which they are attached to form an optionally substituted (C₄-C₈) heteroaryl or (C₄-C₈) heterocyclic ring;

R¹² and R¹³ are independently hydrogen, halogen, —CN, OH, —CONR³R⁴, —NHCOOR⁴, —NHCONR³R⁴, —NHCOR⁴, —NHSO₂R⁷, —SO₂NR³R⁴, —NHSO₂NR³R⁴, optionally substituted (C₁-C₆)alkyl, optionally substituted (C₃-C₈)cycloalkyl, optionally substituted (C₁-C₆) alkoxy, optionally substituted aryl, optionally substituted (C₁-C₆) alkyl-SO₂—, optionally substituted aryl-SO₂—, optionally substituted heteroaryl or optionally substituted heterocyclo;

R¹⁴ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

R¹⁵ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

R¹⁶ is hydrogen, optionally substituted (C₁-C₆)alkyl, (C₁-C₆)alkoxy, halogen, —CN, —NR³R⁴, OH, —NHOCOR⁷, —OCONR⁷R⁸, —NHCONR⁷R⁸ or —CF₃;

with the proviso that at least one of R¹⁴, R¹⁵ and R¹⁶ is not hydrogen;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, for use in the treatment of a disease or condition for which a bromodomain inhibitor is indicated.

In another aspect, there is provided a method of treating autoimmune and inflammatory diseases or conditions which comprises administering to a subject in need thereof a therapeutically effective amount of a bromodomain inhibitor.

In another aspect of the present invention, there is provided a method for treating a bromodomain-containing protein mediated disorder in a patient in need thereof, comprising the step of administering to said patient a compound of the invention.

DETAILED DESCRIPTION OF THE INVENTION

In a first aspect, the invention provides a compound of Formula (I):

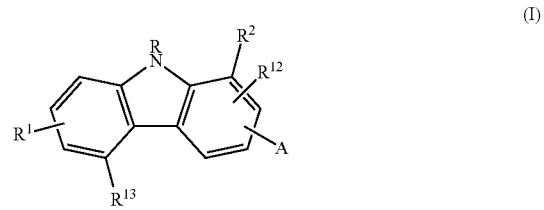

wherein:

A is optionally substituted heteroaryl, wherein the substituents are one or more R¹⁴, R¹⁵ or R¹⁶;

R is hydrogen, optionally substituted (C₁-C₆)alkyl, optionally substituted (C₃-C₈)cycloalkyl(C₁-C₆)alkyl, optionally substituted aryl(C₁-C₆)alkyl, optionally substituted heteroaryl(C₁-C₆)alkyl, optionally substituted heterocyclo(C₁-C₆)alkyl, optionally substituted (C₁-C₆)alkyl-CO—, optionally substituted aryl-CO—, optionally substituted (C₃-C₈)cycloalkyl-CO—, optionally substituted heteroaryl, optionally substituted heterocyclo-CO—, optionally substituted aryl-SO₂—, optionally substituted (C₁-C₆)alkyl-SO₂—, optionally substituted (C₃-C₈)cycloalkyl-SO₂—, optionally substituted heteroaryl-SO₂—, optionally substituted (C₁-C₆)alkyl-OCO— or optionally substituted (C₃-C₈)cycloalkyl-OCO—;

R¹ is halogen, —CN, OH, —NR³R⁴, —CONR³R⁴, —COOH, —OCONR³R⁴, —NHOCOR⁷, —NHCONR⁷R⁸, —NHSO₂NR⁷R⁸, optionally substituted (C₁-C₆)alkyl, optionally substituted (C₂-C₆)alkenyl, optionally substituted (C₂-C₆)alkynyl, optionally substituted (C₁-C₆)alkoxy, optionally substituted (C₃-C₈)cycloalkyl, optionally substituted (C₃-C₈)cycloalkyl-CO—, optionally substituted (C₃-C₈)cycloalkyl-SO₂—, optionally substituted aryl (C₁-C₆) alkoxy, optionally substituted (C₃-C₈)cycloalkyl (C₁-C₆) alkoxy, optionally substituted heterocyclyl-CO—, optionally substituted heterocyclyl, optionally substituted (C₁-C₆)alkyl-SO₂—, —NHSO₂-optionally substituted (C₁-C₆)alkyl, —NHSO₂-optionally substituted heterocyclo, optionally substituted (C₁-C₆)alkyl-NHSO₂— or optionally substituted heterocyclo-NHSO₂—;

R² is H, halogen, —CN, —COOH, —CONR⁷R⁸, —OCONR³R⁴, —NHSO₂R⁷, —NHCOR⁷, —NHCOOR⁷, optionally substituted (C₁-C₆)alkyl, optionally substituted (C₂-C₆)alkynyl, optionally substituted (C₁-C₆)alkoxy, optionally substituted heteroaryl or optionally substituted heterocyclo;

R³ is hydrogen, optionally substituted (C₁-C₆)alkyl, optionally substituted (C₃-C₈)cycloalkyl, optionally substituted (C₂-C₆)alkenyl, optionally substituted (C₂-C₆)alkynyl, cyano(C₁-C₆)alkyl, hydroxy(C₁-C₆)alkyl, optionally substituted aryl, optionally substituted aryl(C₁-C₆)alkyl, optionally substituted aryloxy(C₁-C₆)alkyl, optionally substituted (C₁-C₆)alkyl-SO₂—, optionally substituted heterocyclyl, optionally substituted heterocyclyl(C₁-C₆)alkyl, optionally substituted heteroaryl or optionally substituted heteroaryl (C₁-C₆)alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_2-C_8)$ heteroaryl or $(C_2-C_8)$ heterocyclic ring;

$R^7$ and $R^8$ are independently hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl$(C_1-C_6)$alkyl;

or $R^7$ and $R^8$ may be taken together with the nitrogen atom to which they are attached to form an optionally substituted $(C_4-C_8)$ heteroaryl or $(C_4-C_8)$ heterocyclic ring;

$R^{12}$ and $R^{13}$ are independently hydrogen, halogen, —CN, OH, —CONR$^3$R$^4$, —NHCOOR$^4$, —NHCONR$^3$R$^4$, —NHCOR$^4$, —NHSO$_2$R$^7$, —SO$_2$NR$^3$R$^4$, —NHSO$_2$NR$^3$R$^4$, optionally substituted $(C_1-C_6)$alkyl, optionally substituted $(C_3-C_8)$cycloalkyl, optionally substituted $(C_1-C_6)$ alkoxy, optionally substituted aryl, optionally substituted $(C_1-C_6)$alkyl-$SO_2$—, optionally substituted aryl-$SO_2$—, optionally substituted heteroaryl or optionally substituted heterocyclo;

$R^{14}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

$R^{15}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

$R^{16}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

with the proviso that at least one of $R^{14}$, $R^{15}$ and $R^{16}$ is not hydrogen;

and/or a pharmaceutically acceptable salt, tautomer or stereoisomer thereof.

In another aspect, there is provided a compound of formula (II)

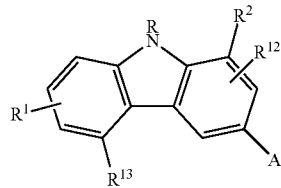

(II)

wherein:

A is optionally substituted heteroaryl, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-$SO_2$—, optionally substituted $(C_1-C_6)$alkyl-$SO_2$—, optionally substituted $(C_3-C_8)$cycloalkyl-$SO_2$—, optionally substituted heteroaryl-$SO_2$—, optionally substituted $(C_1-C_6)$alkyl-OCO— or optionally substituted $(C_3-C_8)$cycloalkyl-OCO—;

$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl-CO—, optionally substituted $(C_3-C_8)$cycloalkyl-$SO_2$—, optionally substituted aryl $(C_1-C_6)$alkoxy, optionally substituted $(C_3-C_8)$cycloalkyl $(C_1-C_6)$alkoxy, optionally substituted heterocyclyl-CO—, optionally substituted heterocyclyl, optionally substituted $(C_1-C_6)$alkyl-$SO_2$—, —NHSO$_2$-optionally substituted $(C_1-C_6)$alkyl, —NHSO$_2$-optionally substituted heterocyclo, optionally substituted $(C_1-C_6)$alkyl-NHSO$_2$— or optionally substituted heterocyclo-NHSO$_2$—;

$R^2$ is H, halogen, —CN, —COOH, —CONR$^7$R$^8$, —OCONR$^3$R$^4$, —NHSO$_2$R$^7$, —NHCOR$^7$, —NHCOOR$^7$, optionally substituted $(C_1-C_6)$alkyl, optionally substituted $(C_2-C_6)$alkynyl, optionally substituted $(C_1-C_6)$alkoxy, optionally substituted heteroaryl or optionally substituted heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl $(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_2-C_8)$ heteroaryl or $(C_2-C_8)$ heterocyclic ring;

$R^7$ and $R^8$ are independently hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-$SO_2$—, optionally substituted heterocyclyl, optionally substituted heterocyclyl$(C_1-C_6)$alkyl, optionally substituted heteroaryl or optionally substituted heteroaryl$(C_1-C_6)$alkyl;

or $R^7$ and $R^8$ may be taken together with the nitrogen atom to which they are attached to form an optionally substituted $(C_4-C_8)$ heteroaryl or $(C_4-C_8)$ heterocyclic ring;

$R^{12}$ and $R^{13}$ are independently hydrogen, halogen, —CN, OH, —CONR$^3$R$^4$, —NHCOOR$^4$, —NHCONR$^3$R$^4$, —NHCOR$^4$, —NHSO$_2$R$^7$, —SO$_2$NR$^3$R$^4$, —NHSO$_2$NR$^3$R$^4$, optionally substituted $(C_1-C_6)$alkyl, optionally substituted $(C_3-C_8)$cycloalkyl, optionally substituted $(C_1-C_6)$ alkoxy, optionally substituted aryl, optionally substituted $(C_1-C_6)$alkyl-$SO_2$—, optionally substituted aryl-$SO_2$—, optionally substituted heteroaryl or optionally substituted heterocyclo;

$R^{14}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

$R^{15}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

$R^{16}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

with the proviso that at least one of $R^{14}$, $R^{15}$ or $R^{16}$ is not hydrogen;

and/or a pharmaceutically acceptable salt, tautomer or stereoisomer thereof.

In another aspect, there is provided a compound of formula (III)

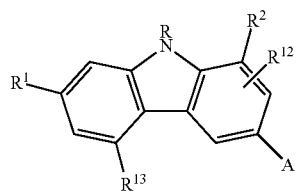

(III)

wherein

A is optionally substituted heteroaryl, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted $(C_3-C_8)$cycloalkyl-SO$_2$—, optionally substituted heteroaryl-SO$_2$—, optionally substituted $(C_1-C_6)$alkyl-OCO— or optionally substituted $(C_3-C_8)$cycloalkyl-OCO—;

$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_3-C_8)$cycloalkyl, optionally substituted $(C_3-C_8)$cycloalkyl-CO—, optionally substituted $(C_3-C_8)$cycloalkyl-SO$_2$—, optionally substituted aryl $(C_1-C_6)$ alkoxy, optionally substituted $(C_3-C_8)$cycloalkyl $(C_1-C_6)$ alkoxy, optionally substituted heterocyclyl-CO—, optionally substituted heterocyclyl, optionally substituted $(C_1-C_6)$alkyl-SO$_2$—, —NHSO$_2$-optionally substituted $(C_1-C_6)$alkyl, —NHSO$_2$-optionally substituted heterocyclo, optionally substituted $(C_1-C_6)$alkyl-NHSO$_2$— or optionally substituted heterocyclo-NHSO$_2$—;

$R^2$ is H, halogen, —CN, —COOH, —CONR$^7$R$^8$, —OCONR$^3$R$^4$, —NHSO$_2$R$^7$, —NHCOR$^7$, —NHCOOR$^7$, optionally substituted $(C_1-C_6)$alkyl, optionally substituted $(C_2-C_6)$alkynyl, optionally substituted $(C_1-C_6)$alkoxy, optionally substituted heteroaryl or optionally substituted heterocyclo;

$R^3$ is hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl$(C_1-C_6)$alkyl, $R^4$ is hydrogen, optionally substituted $(C_1-C_6)$alkyl or optionally substituted $(C_3-C_8)$cycloalkyl;

or $R^3$ and $R^4$ may be taken together with the nitrogen atom to which they are attached to form an optionally substituted $(C_2-C_8)$ heteroaryl or $(C_2-C_8)$ heterocyclic ring;

$R^7$ and $R^8$ are independently hydrogen, optionally substituted $(C_1-C_6)$alkyl, optionally substituted $(C_3-C_8)$cycloalkyl, optionally substituted $(C_2-C_6)$alkenyl, optionally substituted $(C_2-C_6)$alkynyl, cyano$(C_1-C_6)$alkyl, hydroxy$(C_1-C_6)$alkyl, optionally substituted aryl, optionally substituted aryl$(C_1-C_6)$alkyl, optionally substituted aryloxy$(C_1-C_6)$alkyl, optionally substituted $(C_1-C_6)$alkyl-SO$_2$—, optionally substituted heterocyclyl, optionally substituted heterocyclyl$(C_1-C_6)$alkyl, optionally substituted heteroaryl or optionally substituted heteroaryl$(C_1-C_6)$alkyl;

or $R^7$ and $R^8$ may be taken together with the nitrogen atom to which they are attached to form an optionally substituted $(C_4-C_8)$ heteroaryl or $(C_4-C_8)$ heterocyclic ring;

$R^{12}$ and $R^{13}$ are independently hydrogen, halogen, —CN, OH, —CONR$^3$R$^4$, —NHCOOR$^4$, —NHCONR$^3$R$^4$, —NHCOR$^4$, —NHSO$_2$R$^7$, —SO$_2$NR$^3$R$^4$, —NHSO$_2$NR$^3$R$^4$, optionally substituted $(C_1-C_6)$alkyl, optionally substituted $(C_3-C_8)$cycloalkyl, optionally substituted $(C_1-C_6)$ alkoxy, optionally substituted aryl, optionally substituted $(C_1-C_6)$ alkyl-SO$_2$—, optionally substituted aryl-SO$_2$—, optionally substituted heteroaryl or optionally substituted heterocyclo;

$R^{14}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

$R^{15}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

$R^{16}$ is hydrogen, optionally substituted $(C_1-C_6)$alkyl, $(C_1-C_6)$alkoxy, halogen, —CN, —NR$^3$R$^4$, OH, —NHOCOR$^7$, —OCONR$^7$R$^8$, —NHCONR$^7$R$^8$ or —CF$_3$;

with the proviso that at least one of $R^{14}$, $R^{15}$ and $R^{16}$ is not hydrogen;

and/or a pharmaceutically acceptable salt, tautomer or stereoisomer thereof.

In another aspect, there is provided a compound of the formula

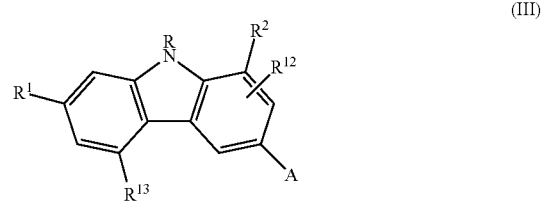

(III)

wherein

A is optionally substituted heteroaryl, wherein the substituents are one or more $R^{14}$, $R^{15}$ or $R^{16}$;

R is hydrogen, optionally substituted $(C_1-C_6)$alkyl, optionally substituted $(C_3-C_8)$cycloalkyl$(C_1-C_6)$alkyl, optionally substituted aryl$(C_1-C_6)$alkyl, optionally substituted heteroaryl$(C_1-C_6)$alkyl, optionally substituted heterocyclo$(C_1-C_6)$alkyl, optionally substituted $(C_1-C_6)$alkyl-CO—, optionally substituted aryl-CO—, optionally substituted $(C_3-C_8)$cycloalkyl-CO—, optionally substituted heteroaryl, optionally substituted heterocyclo-CO—, optionally substituted aryl-SO$_2$—, optionally substituted $(C_1-C_6)$alkyl-SO$_2$—, optionally substituted $(C_3-C_8)$cycloalkyl-SO$_2$—, optionally substituted heteroaryl-SO$_2$—, optionally substituted (C$_1$-C$_6$)alkyl-OCO— or optionally substituted (C$_3$-C$_8$)cycloalkyl-OCO—;

R$^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted heterocyclyl, optionally substituted (C$_1$-C$_6$)alkyl-SO$_2$—, —NHSO$_2$-optionally substituted (C$_1$-C$_6$)alkyl, —NHSO$_2$-optionally substituted heterocyclo, optionally substituted (C$_1$-C$_6$)alkyl-NHSO$_2$— or optionally substituted heterocyclo-NHSO$_2$—;

R$^2$ is H, halogen, —CN, —COOH, —CONR$^7$R$^8$, —OCONR$^3$R$^4$, —NHSO$_2$R$^7$, —NHCOR$^7$, —NHCOOR$^7$, optionally substituted (C$_1$-C$_6$)alkyl, optionally substituted (C$_2$-C$_6$)alkynyl, optionally substituted (C$_1$-C$_6$)alkoxy, optionally substituted heteroaryl or optionally substituted heterocyclo;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, R$^4$ is hydrogen, optionally substituted (C$_1$-C$_6$)alkyl or optionally substituted (C$_3$-C$_8$)cycloalkyl;

or R$^3$ and R$^4$ may be taken together with the nitrogen atom to which they are attached to form an optionally substituted (C$_2$-C$_8$) heteroaryl or (C$_2$-C$_8$) heterocyclic ring;

R$^7$ and R$^8$ are independently hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl(C$_1$-C$_6$)alkyl;

or R$^7$ and R$^8$ may be taken together with the nitrogen atom to which they are attached to form an optionally substituted (C$_4$-C$_8$) heteroaryl or (C$_4$-C$_8$) heterocyclic ring;

R$^{12}$ and R$^{13}$ are independently hydrogen, halogen, —CN, OH, —CONR$^3$R$^4$, —NHCOOR$^4$, —NHCONR$^3$R$^4$, —NHCOR$^4$, —NHSO$_2$R$^7$, —SO$_2$NR$^3$R$^4$, —NHSO$_2$NR$^3$R$^4$, optionally substituted (C$_1$-C$_6$)alkyl, optionally substituted (C$_3$-C$_8$)cycloalkyl, optionally substituted (C$_1$-C$_6$) alkoxy, optionally substituted aryl, optionally substituted (C$_1$-C$_6$)alkyl-SO$_2$—, optionally substituted aryl-SO$_2$—, optionally substituted heteroaryl or optionally substituted heterocyclo;

R$^{14}$ is hydrogen or optionally substituted (C$_1$-C$_6$)alkyl;
R$^{15}$ is hydrogen or optionally substituted (C$_1$-C$_6$)alkyl;
R$^{16}$ is hydrogen or optionally substituted (C$_1$-C$_6$)alkyl;
with the proviso that at least one of R$^{14}$, R$^{15}$ and R$^{16}$ is not hydrogen;

and/or a pharmaceutically acceptable salt, tautomer or stereoisomer thereof.

In another aspect, there is provided a compound of the formula

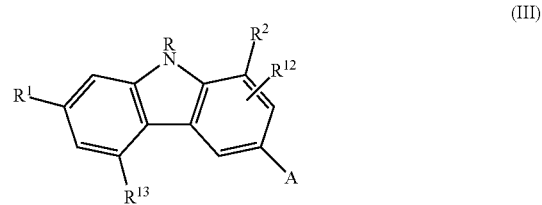

(III)

wherein

A is optionally substituted heteroaryl, wherein the substituents are one or more R$^{14}$, R$^{15}$ or R$^{16}$;

R is hydrogen, optionally substituted (C$_1$-C$_6$)alkyl, optionally substituted (C$_3$-C$_8$)cycloalkyl(C$_1$-C$_6$)alkyl, optionally substituted aryl(C$_1$-C$_6$)alkyl, optionally substituted heteroaryl(C$_1$-C$_6$)alkyl, optionally substituted heterocyclo(C$_1$-C$_6$)alkyl, optionally substituted (C$_1$-C$_6$)alkyl-CO—, optionally substituted aryl-CO—, optionally substituted (C$_3$-C$_8$)cycloalkyl-CO—, optionally substituted heteroaryl, optionally substituted heterocyclo-CO—, optionally substituted aryl-SO$_2$—, optionally substituted (C$_1$-C$_6$)alkyl-SO$_2$—, optionally substituted (C$_3$-C$_8$)cycloalkyl-SO$_2$—, optionally substituted heteroaryl-SO$_2$—, optionally substituted (C$_1$-C$_6$)alkyl-OCO— or optionally substituted (C$_3$-C$_8$)cycloalkyl-OCO—;

R$^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkoxy, optionally substituted (C$_3$-C$_8$)cycloalkyl, optionally substituted (C$_3$-C$_8$)cycloalkyl-CO—, optionally substituted (C$_3$-C$_8$)cycloalkyl-SO$_2$—, optionally substituted aryl (C$_1$-C$_6$)alkoxy, optionally substituted (C$_3$-C$_8$)cycloalkyl (C$_1$-C$_6$)alkoxy, optionally substituted heterocyclyl-CO—, optionally substituted heterocyclyl, optionally substituted (C$_1$-C$_6$)alkyl-SO$_2$—, —NHSO$_2$-optionally substituted (C$_1$-C$_6$)alkyl, —NHSO$_2$-optionally substituted heterocyclo, optionally substituted (C$_1$-C$_6$)alkyl-NHSO$_2$— or optionally substituted heterocyclo-NHSO$_2$—;

R$^2$ is —CN, —COOH or —CONR$^7$R$^8$;

R$^3$ is hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-C$_6$)alkyl, optionally substituted (C$_1$-C$_6$)alkyl-SO$_2$—, optionally substituted heterocyclyl, optionally substituted heterocyclyl(C$_1$-C$_6$)alkyl, optionally substituted heteroaryl or optionally substituted heteroaryl (C$_1$-C$_6$)alkyl, R$^4$ is hydrogen, optionally substituted (C$_1$-C$_6$)alkyl or optionally substituted (C$_3$-C$_8$)cycloalkyl;

or R$^3$ and R$^4$ may be taken together with the nitrogen atom to which they are attached to form an optionally substituted (C$_2$-C$_8$) heteroaryl or (C$_2$-C$_8$) heterocyclic ring;

R$^7$ and R$^8$ are independently hydrogen, optionally substituted (C$_1$-C$_6$)alkyl, optionally substituted (C$_3$-C$_8$)cycloalkyl, optionally substituted (C$_2$-C$_6$)alkenyl, optionally substituted (C$_2$-C$_6$)alkynyl, cyano(C$_1$-C$_6$)alkyl, hydroxy(C$_1$-C$_6$)alkyl, optionally substituted aryl, optionally substituted aryl(C$_1$-C$_6$)alkyl, optionally substituted aryloxy(C$_1$-

$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ and $R^{13}$ are independently hydrogen, halogen, —CN, OH, —CONR$^3$R$^4$, —NHCOOR$^4$, —NHCONR$^3$R$^4$, —NH-COR$^4$, —NHSO$_2$R$^7$, —SO$_2$NR$^3$R$^4$, —NHSO$_2$NR$^3$R$^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$) alkyl-$SO_2$—, optionally substituted aryl-$SO_2$—, optionally substituted heteroaryl or optionally substituted heterocyclo;

$R^{14}$ is hydrogen or optionally substituted ($C_1$-$C_6$)alkyl;
$R^{15}$ is hydrogen or optionally substituted ($C_1$-$C_6$)alkyl;
$R^{16}$ is hydrogen or optionally substituted ($C_1$-$C_6$)alkyl;

with the proviso that at least one of $R^{14}$, $R^{15}$ and $R^{16}$ is not hydrogen;

and/or a pharmaceutically acceptable salt, tautomer or stereoisomer thereof.

In another aspect, there is provided a compound of the formula

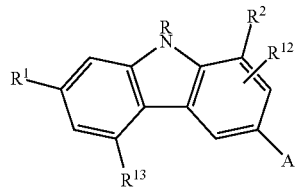

(III)

wherein:

A is optionally substituted heteroaryl, wherein the substituents are one or more $R^{14}$, $R^{15}$ or $R^{16}$;

R is optionally substituted ($C_1$-$C_6$)alkyl, optionally substituted ($C_3$-$C_8$)cycloalkyl($C_1$-$C_6$)alkyl, optionally substituted ($C_1$-$C_6$)alkyl-$SO_2$— or optionally substituted ($C_3$-$C_8$)cycloalkyl-$SO_2$;

$R^1$ is halogen, —CN, OH, —NR$^3$R$^4$, —CONR$^3$R$^4$, —COOH, —OCONR$^3$R$^4$, —NHOCOR$^7$, —NHCONR$^7$R$^8$, —NHSO$_2$NR$^7$R$^8$, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)alkoxy, optionally substituted ($C_3$-$C_8$)cycloalkyl, optionally substituted ($C_3$-$C_8$)cycloalkyl-CO—, optionally substituted ($C_3$-$C_8$)cycloalkyl-$SO_2$—, optionally substituted aryl ($C_1$-$C_6$) alkoxy, optionally substituted ($C_3$-$C_8$)cycloalkyl ($C_1$-$C_6$) alkoxy, optionally substituted heterocyclyl-CO—, optionally substituted heterocyclyl, optionally substituted ($C_1$-$C_6$)alkyl-$SO_2$—, —NHSO$_2$-optionally substituted ($C_1$-$C_6$)alkyl, —NHSO$_2$-optionally substituted heterocyclo, optionally substituted ($C_1$-$C_6$)alkyl-NHSO$_2$— or optionally substituted heterocyclo-NHSO$_2$—;

$R^2$ is —CN, —COOH or —CONR$^7$R$^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_2$-$C_8$) heteroaryl or ($C_2$-$C_8$) heterocyclic ring;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ and $R^{13}$ are independently hydrogen, halogen, —CN, OH, —CONR$^3$R$^4$, —NHCOOR$^4$, —NHCONR$^3$R$^4$, —NH-COR$^4$, —NHSO$_2$R$^7$, —SO$_2$NR$^3$R$^4$, —NHSO$_2$NR$^3$R$^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$) alkyl-$SO_2$—, optionally substituted aryl-$SO_2$—, optionally substituted heteroaryl or optionally substituted heterocyclo;

$R^{14}$ is hydrogen or optionally substituted (C1-C6)alkyl;
$R^{15}$ is hydrogen or optionally substituted (C1-C6)alkyl;
$R^{16}$ is hydrogen or optionally substituted (C1-C6)alkyl;

with the proviso that at least one of $R^{14}$, $R^{15}$ or $R^{16}$ is not hydrogen;

and/or a pharmaceutically acceptable salt, tautomer or stereoisomer thereof.

In another aspect, there is provided a compound of the formula

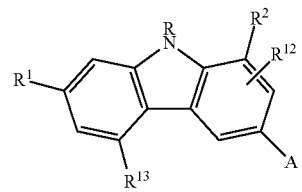

(III)

wherein:

A is optionally substituted heteroaryl, wherein the substituents are one or more $R^{14}$, $R^{15}$ or $R^{16}$;

R is optionally substituted ($C_1$-$C_6$)alkyl, optionally substituted ($C_3$-$C_8$)cycloalkyl($C_1$-$C_6$)alkyl, optionally substituted ($C_1$-$C_6$)alkyl-$SO_2$— or optionally substituted ($C_3$-$C_8$)cycloalkyl-$SO_2$;

$R^1$ is optionally substituted ($C_1$-$C_6$)alkyl, optionally substituted ($C_1$-$C_6$)alkyl-$SO_2$—, optionally substituted ($C_3$-$C_8$)cycloalkyl-CO—, optionally substituted ($C_3$-$C_8$)cycloalkyl-$SO_2$— or optionally substituted heterocyclyl-CO—;

$R^2$ is —CN, —COOH or —CONR$^7$R$^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_2$-$C_8$) heteroaryl or ($C_2$-$C_8$) heterocyclic ring;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy ($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ and $R^{13}$ are independently hydrogen, halogen, —CN, OH, —$CONR^3R^4$, —$NHCOOR^4$, —$NHCONR^3R^4$, —$NHCOR^4$, —$NHSO_2R^7$, —$SO_2NR^3R^4$, —$NHSO_2NR^3R^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$) alkyl-$SO_2$—, optionally substituted aryl-$SO_2$—, optionally substituted heteroaryl or optionally substituted heterocyclo;

$R^{14}$ is hydrogen or optionally substituted (C1-C6)alkyl;

$R^{15}$ is hydrogen or optionally substituted (C1-C6)alkyl;

$R^{16}$ is hydrogen or optionally substituted (C1-C6)alkyl;

with the proviso that at least one of $R^{14}$, $R^{15}$ or $R^{16}$ is not hydrogen;

and/or a pharmaceutically acceptable salt, tautomer or stereoisomer thereof.

In another aspect, there is provided a compound of the formula (III)

wherein

A is

-continued

R is optionally substituted ($C_1$-$C_6$)alkyl, optionally substituted ($C_3$-$C_8$)cycloalkyl($C_1$-$C_6$)alkyl, optionally substituted ($C_1$-$C_6$)alkyl-$SO_2$— or optionally substituted ($C_3$-$C_8$) cycloalkyl-$SO_2$;

$R^1$ is optionally substituted ($C_1$-$C_6$)alkyl, optionally substituted ($C_1$-$C_6$)alkyl-$SO_2$—, optionally substituted ($C_3$-$C_8$) cycloalkyl-CO—, optionally substituted ($C_3$-$C_8$)cycloalkyl-$SO_2$— or optionally substituted heterocyclyl-CO—;

$R^2$ is —CN, —COOH or —$CONR^7R^8$;

$R^3$ is hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl ($C_1$-$C_6$)alkyl, $R^4$ is hydrogen, optionally substituted ($C_1$-$C_6$)alkyl or optionally substituted ($C_3$-$C_8$)cycloalkyl;

or $R^3$ and $R^4$ may be taken together with the nitrogen atom to which they are attached to form an optionally substituted ($C_2$-$C_8$) heteroaryl or ($C_2$-$C_8$) heterocyclic ring;

$R^7$ and $R^8$ are independently hydrogen, optionally substituted ($C_1$-$C_6$)alkyl, optionally substituted ($C_3$-$C_8$)cycloalkyl, optionally substituted ($C_2$-$C_6$)alkenyl, optionally substituted ($C_2$-$C_6$)alkynyl, cyano($C_1$-$C_6$)alkyl, hydroxy ($C_1$-$C_6$)alkyl, optionally substituted aryl, optionally substituted aryl($C_1$-$C_6$)alkyl, optionally substituted aryloxy($C_1$-$C_6$)alkyl, optionally substituted ($C_1$-$C_6$)alkyl-$SO_2$—, optionally substituted heterocyclyl, optionally substituted heterocyclyl($C_1$-$C_6$)alkyl, optionally substituted heteroaryl or optionally substituted heteroaryl($C_1$-$C_6$)alkyl;

or $R^7$ and $R^8$ may be taken together with the nitrogen atom to which they are attached to form an optionally substituted ($C_4$-$C_8$) heteroaryl or ($C_4$-$C_8$) heterocyclic ring;

$R^{12}$ and $R^{13}$ are independently hydrogen, halogen, —CN, OH, —$CONR^3R^4$, —$NHCOOR^4$, —$NHCONR^3R^4$, —$NHCOR^4$, —$NHSO_2R^7$, —$SO_2NR^3R^4$, —$NHSO_2NR^3R^4$, optionally substituted ($C_1$-$C_6$)alkyl, optionally substituted ($C_3$-$C_8$)cycloalkyl, optionally substituted ($C_1$-$C_6$) alkoxy, optionally substituted aryl, optionally substituted ($C_1$-$C_6$) alkyl-$SO_2$—, optionally substituted aryl-$SO_2$—, optionally substituted heteroaryl or optionally substituted heterocyclo;

$R^{14}$ is hydrogen or optionally substituted (C1-C6)alkyl;

$R^{15}$ is hydrogen or optionally substituted (C1-C6)alkyl;

$R^{16}$ is hydrogen or optionally substituted (C1-C6)alkyl;

with the proviso that at least one of $R^{14}$, $R^{15}$ and $R^{16}$ is not hydrogen;

and/or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

One embodiment of the invention provides compounds wherein A is optionally substituted isoxazole, preferably substituted with one or more $C_1$-$C_6$ alkyl groups.

Another embodiment of the invention provides compounds wherein A is

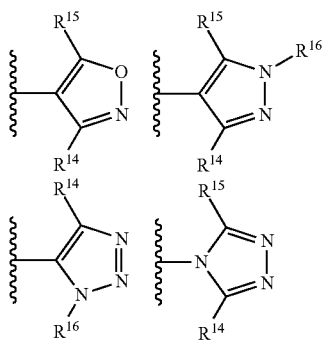

and $R^{14}$, $R^{15}$ and $R^{16}$ are as defined above.

Another embodiment of the invention provides compounds wherein $R^1$ is optionally substituted heterocyclyl-CO—.

Another embodiment of the invention provides compounds wherein $R^1$ is optionally substituted ($C_3$-$C_8$) cycloalkyl-CO—.

Another embodiment of the invention provides compounds wherein $R^1$ is optionally substituted ($C_3$-$C_8$) cycloalkyl-$SO_2$—.

Another embodiment of the invention provides compounds wherein $R^1$ is optionally substituted $C_1$-$C_6$ alkyl-$SO_2$—.

Another embodiment of the invention provides compounds wherein $R^1$ is optionally substituted $C_1$-$C_6$ alkyl.

Another embodiment of the invention provides compounds wherein R is optionally substituted $C_1$-$C_6$ alkyl.

Another embodiment of the invention provides compounds wherein R is optionally substituted ($C_3$-$C_8$) cycloalkyl ($C_1$-$C_6$)alkyl.

Another embodiment of the invention provides compounds wherein R is optionally substituted benzyl.

Another embodiment of the invention provides compounds wherein R is —$SO_2$-optionally substituted $C_1$-$C_6$ alkyl.

Another embodiment of the invention provides compounds wherein R is —$SO_2$-optionally substituted ($C_3$-$C_8$) cycloalkyl.

Another embodiment of the invention provides compounds wherein $R^2$ is —$CONR^7R^8$, where $R^7$ and $R^8$ are preferably hydrogen or $C_1$-$C_6$ alkyl.

Another embodiment of the invention provides compounds wherein $R^2$ is COOH.

Another embodiment of the invention provides compounds wherein $R^2$ is —CN.

In another embodiment, the compounds of the invention have $IC_{50}$ values ≤5 µM.

In another embodiment, the compounds of the invention have $IC_{50}$ values ≤0.5 µM.

In another embodiment, the compounds of the invention have $IC_{50}$ values ≤0.05 µM.

II. Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for inhibiting activity of a bromodomain-containing protein mediated disorder in a patient in need thereof comprising the step of administering to said patient at least one compound of the invention.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a method of inhibiting a bromodomain-containing protein comprising contacting said protein with any exemplified compound or a pharmaceutically acceptable salt or composition thereof.

III. Therapeutic Applications

The compounds of formula (I) of the invention are bromodomain inhibitors and have potential utility in the treatment of diseases and conditions for which a bromodomain inhibitor is indicated.

In one embodiment there is provided a method for the treatment of a disease or condition, for which a bromodomain inhibitor is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may also be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or acute or chronic pancreatitis. In another embodiment the bromodomain inhibitor is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus.

The term "diseases or conditions for which a bromodomain inhibitor is indicated" is intended to include any of or all of the above disease states.

In one embodiment, there is provided a method for inhibiting a bromodomain which comprises contacting the bromodomain with a compound of formula (1) or a pharmaceutically acceptable salt thereof.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as, alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols, this is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

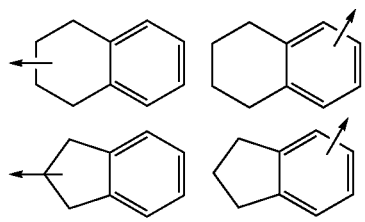

Arrowed lines drawn from the ring system indicate that the bond may be attached to any of the suitable ring atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heteroaryl" or "aromatic heterocyclic group" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furanyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

The term "heteroarylalkyl" refers to a heteroaryl or substituted heteroaryl bonded to an alkyl group connected to the carbazole core of the compound.

As used herein, the terms "heterocyclo", "heterocyclic" or "heterocyclyl" are used interchangeably and refer to a 3-7-membered monocyclic or 7-10-membered bicyclic heterocyclic moiety that is either saturated or partially saturated, and having, in addition to carbon atoms, one or more, preferably one to four, heteroatoms as defined above. Examples of heterocycles include, but are not limited to, pyrrolidinyl, tetrahydrofuranyl, tetrahydropyranyl, piperidyl, pyrrolinyl, piperazinyl, imidazolinyl, morpholinyl, imidazolidinyl, pyrazolidinyl and pyrazolinyl.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a di-substituted hydrazine, R4-M and R7-M, a nucleophile, a hydrazine reducing agent, an activator, a strong base, a hindered amine base and a cyclizing agent. Such amine protecting groups fitting these criteria include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs,* Bundgaard, H., ed., Elsevier (1985), and *Methods in Enzymology,* 112:309-396, Widder, K. et al., eds., Academic Press (1985);

b) Bundgaard, H., Chapter 5, "Design and Application of Prodrugs," *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice,* King, F. D., ed., The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); *The Practice of Medicinal Chemistry,* Wermuth, C. G., ed., Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of compounds of Formula (I) may be accomplished as summarized in Schemes 1-10.

Scheme 1

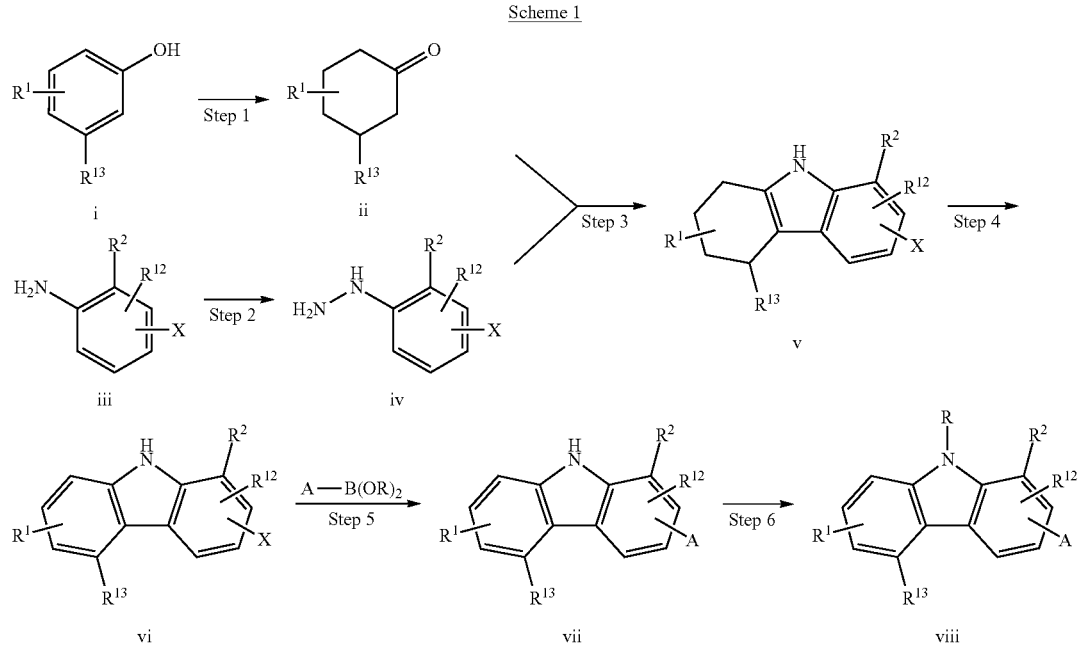

In Step 1 of Scheme 1, a substituted phenol of type i is converted under appropriate conditions to a cyclohexanone of type ii. This may be accomplished, for example, by reduction under hydrogen atmosphere with an appropriate catalyst, such as rhodium on alumina in a suitable solvent such as ethanol followed by oxidation of the resulting alcohol under a variety of conditions known to one skilled in the art, such as the use of chromium (VI) oxide and sulfuric acid in a solvent such as acetone.

Step 2: The second step of Scheme 1 may be accomplished by the conversion of a substituted aniline iii, to a diazonium intermediate under a variety of conditions, such as reaction with sodium nitrite in the presence of a suitable acid, such as hydrochloric acid, in a suitable solvent, such as water, followed by reduction to a hydrazine of type iv under suitable conditions, such as reduction with tin(II) chloride in the presence of hydrochloric acid.

Step 3: Intermediates ii and iv may be converted to a tetrahydrocarbazole of type v under a number of conditions, such as heating in an appropriate solvent, such as acetic acid. Optionally, at this point, the functionality of intermediate iv may be adjusted if desired. For example, if group $R^2$ of intermediate iv is a carboxylic acid, it may be converted to an amide at this point by a variety of conditions known to one skilled in the art, such as by reaction with the desired amine in the presence of a coupling agent, such as EDC and HOBt, in a suitable solvent or mixture of solvents, such as THF and DCM.

Step 4: Intermediate v may be converted to a carbazole of type vi by oxidation with a suitable reagent, such as DDQ, in an appropriate solvent, such as toluene.

Step 5: At this point, if desired, group X of intermediate vi may be converted to group A of Formula (I). For example, if X is a halide and the desired group A is an aryl or heteroaryl ring, the conversion of intermediate vi to intermediate vii may be performed under a variety of conditions known to one skilled in the art, such as reaction with a suitable boronic acid or ester in the presence of a palladium catalyst, such as $PdCl_2(dppf)$ and a suitable base, for example tripotassium phosphate, in an appropriate solvent, such as DMF.

Step 6: At this point, if desired, the group R of Formula (I) may be installed under appropriate conditions. One skilled in the art will recognize that the appropriate conditions depend on the nature of the group R. For example, when R is an alkyl group, the conversion of vii to viii may be effected by reaction of R with an appropriate alkyl halide, for example a bromide or iodide, in the presence of an appropriate base, such as potassium carbonate in a suitable solvent such as acetone. Alternatively, when R is a sulfonyl group, this transformation may be accomplished by the reaction of vii with a suitable sulfonyl chloride in the presence of a suitable base, such as potassium tert-butoxide in a suitable solvent such as THF.

One skilled in the art will recognize that the order of these steps may be changed as necessary or desired to effect the synthesis of a compound of Formula (I), as shown in Scheme 2.

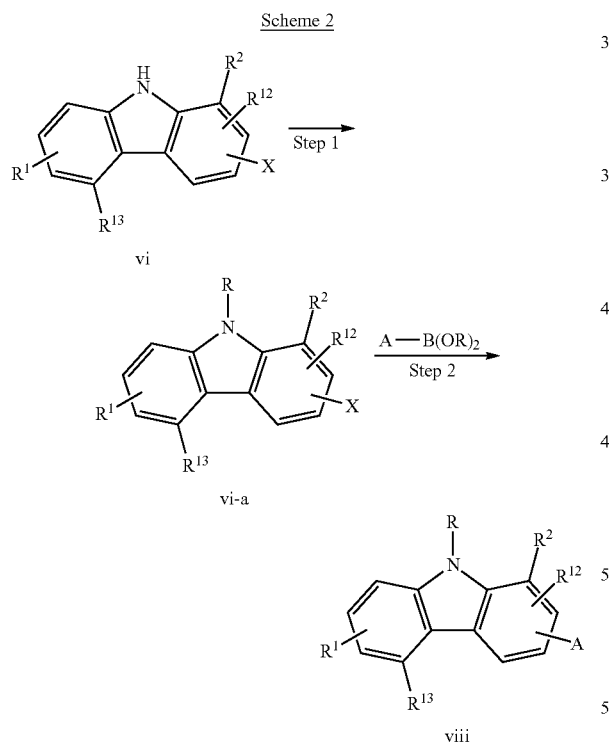

Step 1: One skilled in the art will recognize that the appropriate conditions for Step 1 depend on the nature of the group R. For example, when R is an alkyl group, the conversion of vi to vi-a may be effected by reaction of R with an appropriate alkyl halide, for example a bromide or iodide, in the presence of an appropriate base, such as potassium carbonate in a suitable solvent such as acetone. Alternatively, when R is a sulfonyl group, this transformation may be accomplished by the reaction of vi with a suitable sulfonyl chloride in the presence of a suitable base, such as potassium tert-butoxide in a suitable solvent such as THF.

Step 2: At this point, if desired, group X of intermediate vi-a may be converted to group A of Formula (I). For example, if X is a halide and the desired group A is an aryl or heteroaryl ring, the conversion of intermediate vi-a to intermediate viii may be performed under a variety of conditions known to one skilled in the art, such as reaction with a suitable boronic acid or ester in the presence of a palladium catalyst, such as $PdCl_2(dppf)$ and a suitable base, for example tripotassium phosphate, in an appropriate solvent, such as DMF.

At this point, if desired, further modification of the substituents $R^1$-$R^{13}$ may be conducted as illustrated in Schemes 3-9.

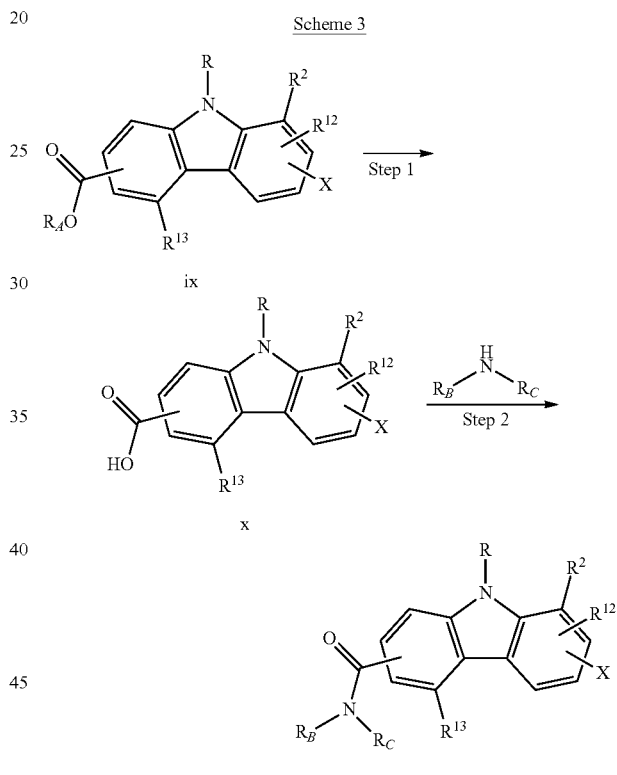

In the event that group $R^1$ of intermediate ix is an ester, it may be modified as shown in Scheme 3.

Step 1: The first step of Scheme 3 may be accomplished by a number of conditions known to one skilled in the art. For example when $R_A$ is ethyl, the ester may be hydrolyzed by reaction with a base such as sodium hydroxide in a solvent or mixture of solvents such as THF, MeOH, and water to give carboxylic acid intermediate x.

Step 2: The second step of Scheme 3 may be accomplished by a number of methods known to one skilled in the art. For example, reaction of intermediate x with an appropriate coupling agent such as HCTU and the desired amine in a suitable solvent such as DMF gives amide intermediate xi, which may be used as desired, for example, in Step 5 or Step 6 of Scheme 1.

Scheme 4

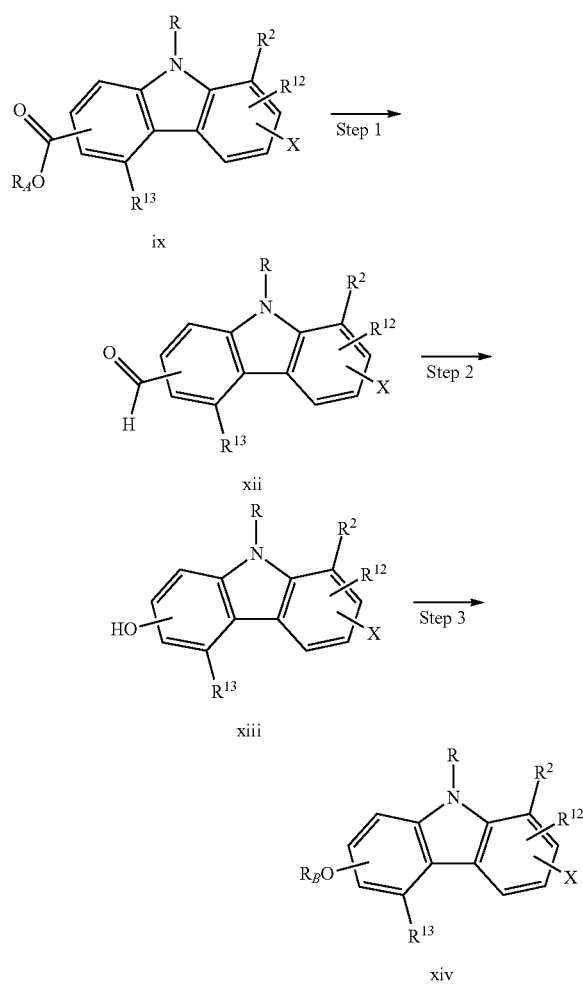

In the event that group R¹ of intermediate ix is an ester, it may be modified as shown in Scheme 4.

Step 1: The first step of Scheme 4 may be accomplished by a number of conditions known to one skilled in the art. For example, the ester of intermediate ix may be reduced to an alcohol with an appropriate reducing agent, such as lithium aluminum hydride in an appropriate solvent, such as THF. This alcohol may then be oxidized to aldehyde intermediate xii by employing suitable oxidation conditions, for example, by using Dess-Martin Periodinane in a solvent such as DCM.

Step 2: Intermediate xii may be converted to phenol intermediate xiii under a variety of conditions, such as by the use of a peroxide such as hydrogen peroxide in a suitable solvent such as methanol.

Step 3: If desired, intermediate xiii may be further modified by the installation of the group $R_B$. One skilled in the art will recognize that the appropriate conditions for this transformation will depend upon the nature of the substituent $R_B$. For example, when $R_B$ is alkyl, it may be installed by reacting intermediate xiii with a suitable alkyl halide, for example methyl iodide, in the presence of a suitable base, such as potassium carbonate in an appropriate solvent, such as acetone. Alternatively, if $R_B$ is a carbamate, it may be installed by reaction of intermediate xiii with a suitably functionalized carbamic chloride in the presence of an appropriate base, such as pyridine. Intermediate xiv may be used as desired, for example, in Step 5 or Step 6 of Scheme 1.

Scheme 5

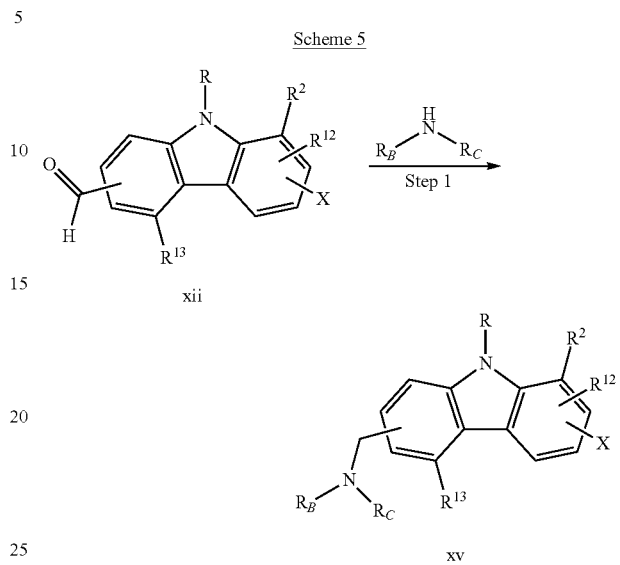

In step 1 of Scheme 5, aldehyde intermediate xii is converted to amine intermediate xv by means of a reductive amination. One skilled in the art will recognize that there are multiple means to accomplish this transformation, such as by reaction of intermediate xii with desired amine in a suitable solvent, such as DMF, followed by the addition of a suitable reducing agent, such as sodium triacetoxyborohydride. Intermediate xv may be used as desired, for example, in Step 5 or Step 6 of Scheme 1.

Scheme 6

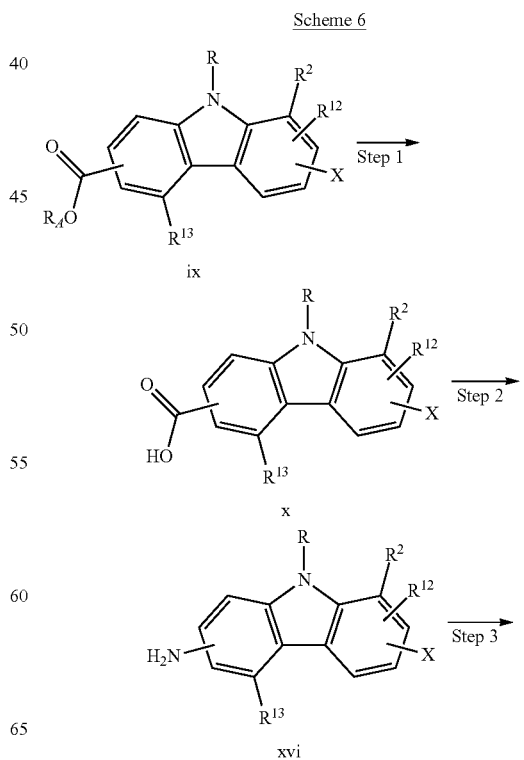

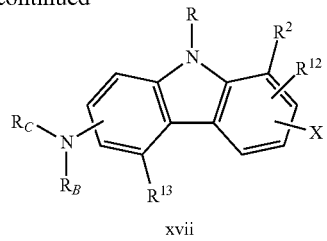

xvii

In the event that group $R^1$ of intermediate ix is an ester, it may be modified as shown in Scheme 6.

Step 1: The first step of Scheme 6 may be accomplished by a number of conditions known to one skilled in the art. For example when $R_A$ is ethyl, the ester may be hydrolyzed by reaction with a base such as sodium hydroxide in a solvent or mixture of solvents such as THF, MeOH, and water to give carboxylic acid intermediate xii.

Step 2: Carboxylic acid intermediate x may be converted to amine intermediate xvi under a variety of conditions, for example by reaction with diphenyl phosphoryl azide in the presence of a base such as triethylamine in a suitable solvent such as dioxane. Addition of an alcohol such as tert-butanol will produce the corresponding carbamate; if this is done a second step may optionally be added to remove the carbamate. For example, a tert-butyl carbamate may be treated with TFA in a solvent such as DCM to produce amine intermediate xvi. Optionally, if group X is a halide such as bromide, it may be converted to group A prior to removal of the carbamate. For example, if the desired group A is an aryl or heteroaryl ring, the conversion of intermediate xii to intermediate xvi may be performed under a variety of conditions known to one skilled in the art, such as reaction with a suitable boronic acid or ester in the presence of a palladium catalyst, such as $PdCl_2(dppf)$ and a suitable base, for example tripotassium phosphate, in an appropriate solvent, such as DMF.

Step 3: Optionally, if further functionalization of amine intermediate xvi is desired by installation of one or more groups $R_B$ and/or $R_C$, this may be done at this point. One skilled in the art will recognize that the appropriate conditions for this transformation will depend upon the nature of the substituent(s) $R_B$ and/or $R_C$. For example, when $R_B$ and/or $R_C$ is alkyl, it may be installed by reacting intermediate xvi with a suitable alkyl halide, for example methyl iodide, in the presence of a suitable base, such as potassium carbonate in an appropriate solvent, such as acetone. Alternatively, if $R_B$ and/or $R_C$ is a carbamate, it may be installed by reaction of intermediate xvi with a suitably functionalized chloroformate, such as ethyl chloroformate, in the presence of an appropriate base such as pyridine, in a suitable solvent such as DCM. If $R_B$ and/or $R_C$ is an acyl group, it may be installed by reaction of intermediate xvi with a suitable acyl halide, such as acetyl chloride, in the presence of a suitable base such as pyridine, in a suitable solvent such as DCM. If $R_B$ and/or $R_C$ is a urea, it may be installed by the reaction of intermediate xvi with the appropriate isocyanate in the presence of a base such as pyridine and a catalyst such as DMAP in a suitable solvent such as DCM. One skilled in the art will recognize that if non-identical groups $R_B$ and $R_C$ are desired, that they may be installed in two steps by sequential application of the appropriate conditions listed above.

Intermediate xvii may be used as desired, for example, in Step 5 or Step 6 of Scheme 1.

Scheme 7

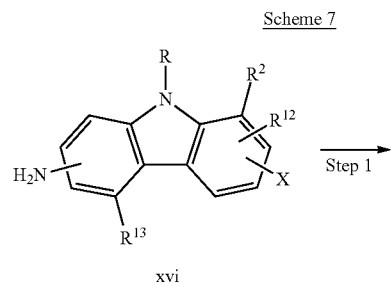

xvi

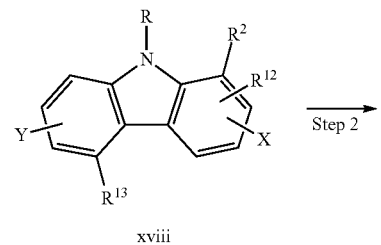

xviii

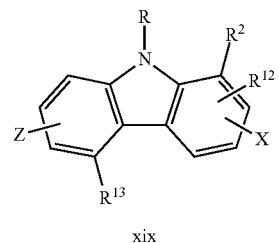

xix

Step 1: In step 1 of Scheme 7, the amine of intermediate xvi may be converted to a halide Y, such as bromide, by reaction of intermediate xvi with an alkyl nitrite such as t-butyl nitrite and a copper source, such as copper(II) bromide, in a suitable solvent, such as acetonitrile.

Step 2: Optionally, the halide Y of intermediate xviii may be converted to a different functional group Z. One skilled in the art will recognize that the appropriate conditions for this transformation will depend upon the nature of the substituent Z. For example, if the desired group Z is an aryl or heteroaryl group is an aryl or heteroaryl ring, the conversion of intermediate xviii to intermediate xix may be performed under a variety of conditions known to one skilled in the art, such as reaction with a suitable boronic acid or ester in the presence of a palladium catalyst, such as $PdCl_2(dppf)$ and a suitable base, for example tripotassium phosphate, in an appropriate solvent, such as THF. Intermediate xix may be used as desired, for example, in Step 5 or Step 6 of Scheme 1.

Scheme 8

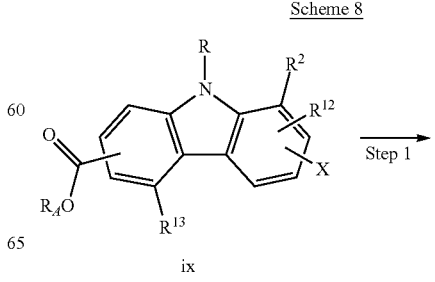

ix

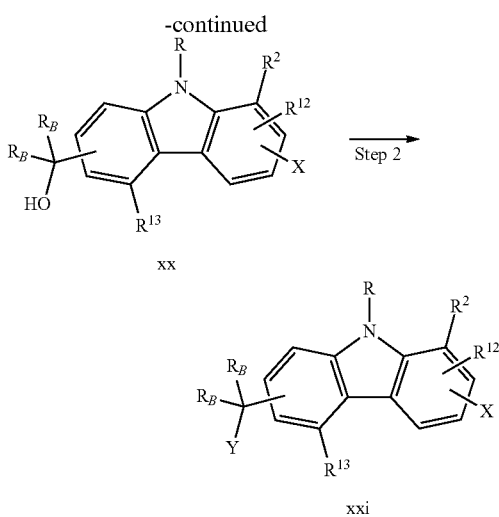

Step 1: The ester intermediate ix may be converted to a dialkyl carbinol intermediate xx under a variety of conditions, for example, by reaction of intermediate ix with a suitable organometallic reagent, for example methylmagnesium bromide in a suitable solvent or mixture of solvents, such as THF and diethyl ether.

Step 2: Optionally, the alcohol in intermediate xx may be converted to a different functional group Y at this point. One skilled in the art will recognize that the appropriate conditions for this transformation will depend upon the nature of the substituent Y. For example, if the desired group Y is an amine, this transformation may be accomplished by reacting intermediate xx with a suitable acid, such as hydrochloric acid, in a suitable solvent, such as diethyl ether followed by the addition of the desired amine. Intermediate xxi may be used as desired, for example, in Step 5 or Step 6 of Scheme 1.

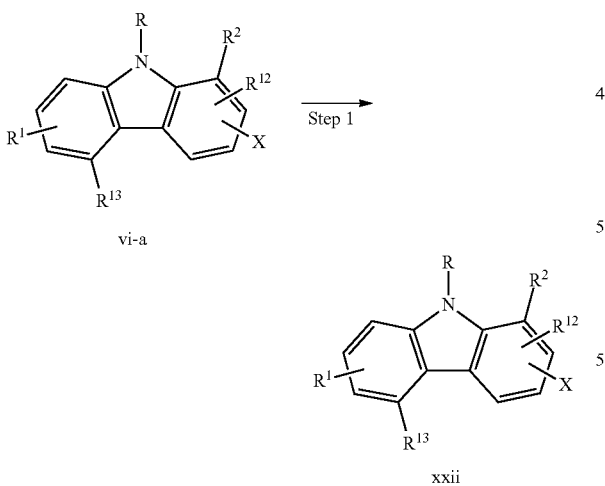

At any convenient point, the functional group $R^2$ of intermediates v-viii in Scheme 1 may be adjusted if desired. For example, the group $R^2$ of intermediate vi may be altered as described in Scheme 9.

Step 1: In step 1 of Scheme 9, functional group $R^2$ of intermediate vi-a may optionally be converted to another functional group $R^2$ of intermediate xxii One skilled in the art will recognize that the appropriate conditions for this transformation will depend upon the nature of the substituents $R^2$ in vi-a and xxii. For example, if $R^2$ intermediate vi-a is a primary amide and the desired group $R^2$ of intermediate xxii is a nitrile, the transformation may be accomplished by reacting intermediate vi-a with a suitable dehydrating agent, such as Burgess reagent in a suitable solvent such a DCM. Alternatively, if $R^2$ of intermediate vi-a is a primary amide and the desired group $R^2$ of intermediate xxii is a thioamide, the transformation may be accomplished by reacting intermediate vi-a with a reagent such as phosphorous pentasulfide and a base such as sodium bicarbonate in an appropriate solvent such as diglyme. Alternatively, if $R^2$ of intermediate vi-a is a primary amide and the desired group $R^2$ of intermediate xxii is an isoxazole, the transformation may be accomplished by reacting intermediate vi-a with a reagent such as 2,3-dibromoprop-1-ene and a base such as cesium carbonate in a suitable solvent such as DMF. Intermediate xxii may be used as desired, for example, in Step 5 or Step 6 of Scheme 1.

Alternatively, carbazole intermediate viii may be prepared as shown in Scheme 10.

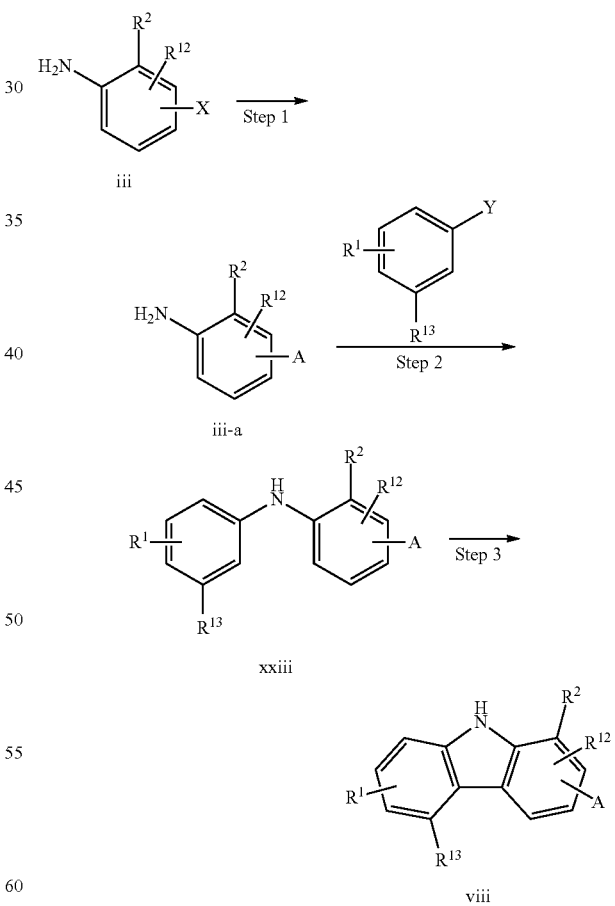

Step 1: Optionally, in step 1 of Scheme 10, group A of Formula (I) may be installed from a suitable halide or pseudohalide in intermediate iii. For example, if X is a bromide and the desired group A is an aryl or heteroaryl ring, the conversion of intermediate iii to intermediate iii-a may be performed under a variety of conditions known to one skilled in the art, such as reaction with a suitable boronic acid or ester in the presence of a palladium catalyst, such as PdCl$_2$(dppf) and a suitable base, for example tripotassium phosphate, in an appropriate solvent, such as THF.

Step 2: In step 2 of Scheme 10, intermediate iii-a is converted to intermediate xxiii by reaction with an aryl halide or pseudohalide in the presence of a suitable catalyst, such as chloro(2-dicyclohexylphosphino-2',4',6'-triisopropyl-1,1'-biphenyl)[2-(2'-amino-1,1'-biphenyl)]palladium (II), in the presence of a suitable base, such as cesium carbonate, in an appropriate solvent, such as toluene.

Step 3: The third step of Scheme 10 may be accomplished by reaction of intermediate xxiii with a suitable catalyst, such as palladium(II) acetate, in a suitable solvent, such as pivalic acid, to give intermediate viii. Intermediate viii may be used as desired, for example, in Step 5 or Step 6 of Scheme 1.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

ACN acetonitrile
AcOH acetic acid
AlMe$_3$ trimethyl aluminum
aq aqueous
Bn benzyl
Boc tert-butoxycarbonyl
Boc$_2$O di-tert-butyl dicarbonate
Burgess Reagent 1-methoxy-N-triethylammoniosulfonyl-methanimidate
CBz benzyloxycarbonyl
DCC 1,3-dicyclohexylcarbodiimide
DCM dichloromethane
DDQ 2,3-dichloro-5,6-dicyano-1,4-benzoquinone
DIEA diisopropylethylamine
DMAP 4-dimethylaminopyridine
DME dimethoxyethane
DMF dimethylformamide
DMSO dimethyl sulfoxide
Pd(dppf)$_2$Cl$_2$ [1,1'-bis(diphenylphosphino)ferrocene]dichloropalladium(II)
EDC 1-(3-dimethylaminopropyl)-3-ethylcarbodiimide hydrochloride
Et$_2$AlCl diethyl aluminum chloride
Et$_3$N triethyl amine
Et$_2$O diethyl ether
EtOH ethanol
EtOAc ethyl acetate
equiv. equivalent(s)
g gram(s)
h or hr hour(s)
HCTU O-(6-Chlorobenzotriazol-1-yl)-N,N,N',N'-tetramethyluronium hexafluorophosphate
HOBt hydroxybenzotriazole
HPLC high pressure liquid chromatography
iPrOH isopropyl alcohol
KOtBu potassium tert-butoxide
LCMS Liquid Chromatography-Mass Spectroscopy
LDA lithium diisopropylamide
LiHMDS lithium bis(trimethylsilyl)amide
Me methyl
MeI methyl iodide
MeOH methanol
min minute(s)
mL milliliter(s)
mmol millimolar
MTBE methyl t-butyl ether
NaHMDS sodium bis(trimethylsilyl)amide
n-BuLi n-butyl lithium
NH$_4$OAc ammonium acetate
NMP N-methylpyrrolidinone
Pd(OAc)$_2$ palladium acetate
RT or Rt retention time
r.t. room temperature
sat saturated
t-Bu tertiary butyl
t-BuLi t-butyl lithium
tBuOH tertiary butyl alcohol
tBuOMe tert-butyl methyl ether
TBTU O-(1H-benzotriazol-1-yl)-N,N,N',N'-tetramethyluronium tetrafluoroborate
TEA triethylamine
TFA trifluoroacetic acid
Tf$_2$O trifluoromethylsulfonic anhydride
THF tetrahydrofuran
18-Crown-6 [C$_2$H$_4$O]$_6$ IUPAC name—1,4,7,10,13,16-hexaoxacyclooctadecane Example 1

3-(3,5-dimethyl-4-isoxazolyl)-7-(1-piperidinylcarbonyl)-9H-carbazole-1-carboxamide

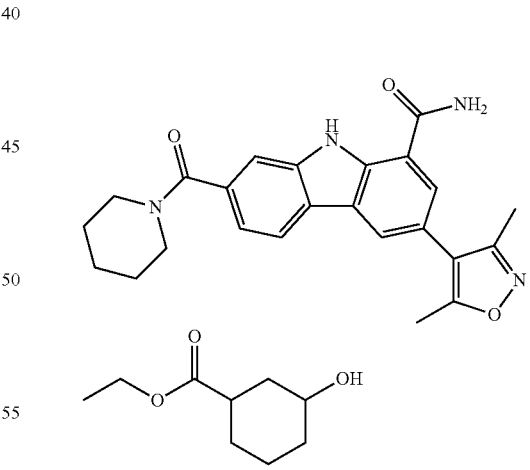

Step 1a: Ethyl 3-hydroxycyclohexanecarboxylate

A solution of ethyl 3-hydroxybenzoate (50 g, 301 mmol) in ethanol (700 mL) was combined with rhodium, 5% on alumina (5 g, 2.429 mmol) in a 2 liter Parr pressure bottle and shaken under a hydrogen atmosphere (60 psi) at room temperature. The bottle was repressurized with hydrogen three times over the next 8 hours, then shaken for three days.

The mixture was filtered through Celite, the solids were rinsed with ethanol and the filtrate was concentrated under vacuum to provide a colorless liquid (53.3 g). HPLC Ret. Time=1.05 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=173 [M+H]$^+$.

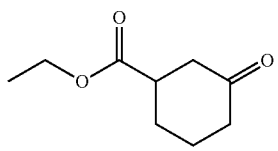

Step 1b: Ethyl 3-oxocyclohexanecarboxylate

A solution of ethyl 3-hydroxycyclohexanecarboxylate (53.3 g, 294 mmol) in acetone (700 mL) was stirred in an ice-water bath (internal temperature 10-15° C.) and treated dropwise with Jones reagent (120 mL, 320 mmol). After addition of all of the Jones reagent, a yellow color persisted. The reaction was stirred 25 minutes at 10-15° C., then 40 ml isopropanol was added and the reaction was stirred 15 minutes at 10-15° C.

The solution turned blue-green. The supernatant was decanted from the sludge, which was stirred and triturated three times with fresh acetone and decanted through a Celite pad. The combined supernatants were concentrated under vacuum and the residue was taken up in ether, washed with a 1:1 mixture of saturated NaHCO$_3$ solution and brine, dried over MgSO$_4$ and concentrated under vacuum to provide the desired product (52.2 g, 95%) as a colorless oil.

HPLC Ret. Time=1.07 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=171 [M+H]$^+$.

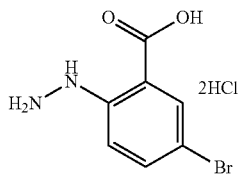 [SMILES: NNc1ccc(Br)cc1C(=O)O]

Step 1c: 5-bromo-2-hydrazinylbenzoic acid dihydrochloride

A solution of sodium nitrite (7.00 g, 101 mmol) in H$_2$O, (34 mL) was added dropwise to a cooled (−14° C., ice-salt bath), cream-colored suspension of 2-amino-5-bromobenzoic acid (20.87 g, 97 mmol) in conc. HCl (96 mL), at such rate that the temperature did not exceed 0° C. (over 12 min). The light brown-colored solution was stirred at 0° C. for 6 min, and was then added in portions to a cooled (−20° C., isopropanol/dry ice) and rapidly stirred solution of Tin (II) chloride (55.0 g, 290 mmol) in con. HCl (34.0 mL), at such a rate that the temperature stayed between −20° C. and −5° C. (over 30 min). In between additions, the flask containing the diazonium intermediate was kept in a ice/salt bath. After completion of the addition, the reaction mixture was stirred for 45 minutes at −10° C., then the cooling bath was removed. The resulting cream-colored suspension was warmed up to room temperature and stirred at room temperature for 1 h. The solid was collected by filtration, washed with water and ether, dried by sucking air through the filter cake to afford the desired product (21.98 g) as a grey solid.

HPLC Ret. Time=0.56 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=231 [M+H]$^+$.

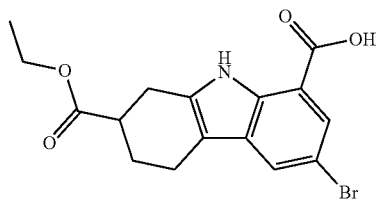 [SMILES: CCOC(=O)C1CCc2c([nH]c3c(C(=O)O)cc(Br)cc23)C1]

Step 1d: 6-bromo-2-(ethoxycarbonyl)-2,3,4,9-tetrahydro-1H-carbazole-8-carboxylic acid A cream colored suspension of 5-bromo-2-hydrazinylbenzoic acid dihydrochloride (21.9 g, 69.9 mmol) and ethyl 3-oxocyclohexanecarboxylate (15.0 g, 80 mmol) in AcOH (175 mL) was heated at reflux (oil bath temperature 130° C.) for 4 h. Heating was stopped and the reaction mixture was cooled to room temperature and filtered. The solid was washed with acetic acid and dried in a nitrogen stream to give the desired product (19.9 g).

HPLC Ret. Time=1.45 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=366 [M+H]$^+$.

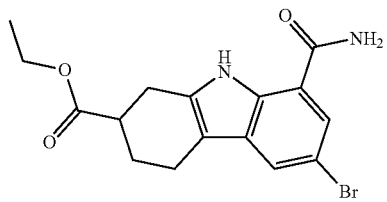 [SMILES: CCOC(=O)C1CCc2c([nH]c3c(C(N)=O)cc(Br)cc23)C1]

Step 1e: Ethyl 6-bromo-8-carbamoyl-2,3,4,9-tetrahydro-1H-carbazole-2-carboxylate To a light suspension of 6-bromo-2-(ethoxycarbonyl)-2,3,4,9-tetrahydro-1H-carbazole-8-carboxylic acid (18.5 g, 42.4 mmol), EDC (10.58 g, 55.2 mmol), and 1-hydroxybenzotriazole hydrate (8.45 g, 55.2 mmol) in THF/CH$_2$Cl$_2$ (5/1) (480 mL) was added ammonium hydroxide (9.91 mL, 76 mmol). The reaction was stirred at room temperature over the weekend. The reaction mixture was concentrated and then triturated with 500 ml water (sonicate for 2 minutes), then filtered through a medium porosity glass frit. The solids were washed with water and dried in a nitrogen stream to give the desired product (15.1 g).

HPLC Ret. Time=1.94 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=365 [M+H]⁺.

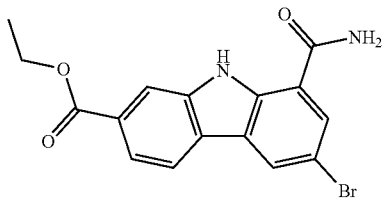 [SMILES: CCOC(=O)c1ccc2c(c1)[nH]c1c(C(N)=O)cc(Br)cc12]

Step 1f: Ethyl 6-bromo-8-carbamoyl-9H-carbazole-2-carboxylate

Ethyl 6-bromo-8-carbamoyl-2,3,4,9-tetrahydro-1H-carbazole-2-carboxylate (15.1 g, 39.7 mmol), DDQ (23.5 g, 101 mmol) and toluene (500 ml) were combined in a 1 liter round bottom flask equipped with a reflux condenser and heated to reflux for 45 minutes. The reaction mixture was cooled to room temperature and filtered through a medium porosity glass frit. Solids were washed with toluene and dried under a stream of nitrogen. The crystalline product was dissolved in a mixture of ethyl acetate and 1 M aqueous Na₂CO₃ solution. The layers were separated; the aqueous extracted two more times with 1 M aqueous Na₂CO₃ solution, then once with sat. aq. NH₄Cl solution, then with brine. All aqueous layers were back-extracted with ethyl acetate once. The organic phase was dried over MgSO₄, filtered and concentrated.

The mother liquor from the filtration was concentrated under vacuum, then dissolved in ethyl acetate and extracted with 1M Na₂CO₃ solution 3×, then once with sat. aq. NH₄Cl solution and then with brine. The organic layer was dried over MgSO₄, filtered and concentrated under vacuum. This material was combined with the material from the previous extraction to give the desired product (17.0 g, 83%), which was used without further purification.

HPLC Ret. Time=1.96 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=361 [M+H]⁺.

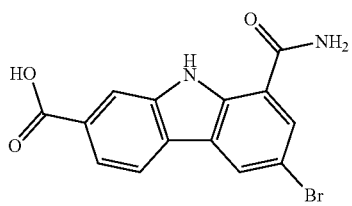 [SMILES: NC(=O)c1cc(Br)cc2c1[nH]c1cc(C(=O)O)ccc12]

Step 1 g: 6-bromo-8-carbamoyl-9H-carbazole-2-carboxylic acid

Ethyl 6-bromo-8-carbamoyl-9H-carbazole-2-carboxylate (13.60 g, 26.4 mmol) was suspended into THF (240 ml)/MeOH (50 ml) (290 mL). NaOH (1M) (79 mL, 79 mmol) was added. The resulting mixture was stirred overnight at r.t. An additional 30 ml of 1N NaOH was added and the mixture was stirred for additional 3 hrs at r.t. The mixture was concentrated to almost dryness. 1 L of water was added and the mixture was sonicated for 30 mins. 110 ml of 1N HCl was added to above mixture while stirring. Brown precipitate was filtered and washed with H₂O and dried overnight via air-suction. The desired product (12.1 g) was obtained and used without further purification.

HPLC Ret. Time=0.97 min, column: Luna, 3.0×55 mm; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 1-minute hold at 100% B; Flow: 4 mL/min. MS (ES): m/z=333 [M+H]⁺.

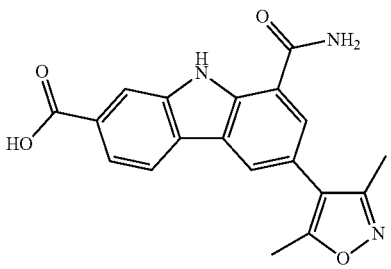 [SMILES: Cc1noc(C)c1-c1cc(C(N)=O)c2[nH]c3cc(C(=O)O)ccc3c2c1]

Step 1 h: 8-carbamoyl-6-(3,5-dimethylisoxazol-4-yl)-9H-carbazole-2-carboxylic acid To 6-bromo-8-carbamoyl-9H-carbazole-2-carboxylic acid (1050 mg, 3.15 mmol), 3,5-dimethyl-4-(4,4,5,5-tetramethyl-1,3,2-dioxaborolan-2-yl)isoxazole (1055 mg, 4.73 mmol) was added DMF (12 mL). The reaction was degassed and then PdCl₂(dppf)-CH₂Cl₂Adduct (129 mg, 0.158 mmol) and aqueous tripotassium phosphate (3.15 mL, 9.46 mmol) were added. The reaction was degassed and heated at 80° C. 10% LiCl was added and the reaction was extracted with EtOAc, dried, and concentrated to give the desired product (800 mg), which was used without further purification.

HPLC Ret. Time=0.74, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 2 minute, then a 2-minute hold at 98% B; Flow: 0.8 mL/min. MS (ES): m/z=350 [M+H]⁺.

To 8-carbamoyl-6-(3,5-dimethylisoxazol-4-yl)-9H-carbazole-2-carboxylic acid (26 mg, 0.074 mmol), was added HCTU (89 mg, 0.223 mmol), N,N-dimethylpyridin-4-amine (27.3 mg, 0.223 mmol) and DMF (1.0 mL). Piperidine (38.0 mg, 0.447 mmol) was then added and the reaction was allowed to stir at room temperature for 2 h. The crude material was filtered and purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate;

Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation.

The yield of the final product was 3.7 mg, and its estimated purity by LCMS analysis was 100%. Two analytical LC/MS injections were used to determine the final purity. Injection 1 conditions: Retention Time: 1.51 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=416 [M+H$^+$]. Injection 2 conditions: Retention Time: 1.52 min; Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Example 2

9-(cyclopropylmethyl)-3-(3,5-dimethyl-4-isoxazolyl)-7-((cis-2,6-dimethyl-4-morpholinyl)carbonyl)-9H-carbazole-1-carboxamide

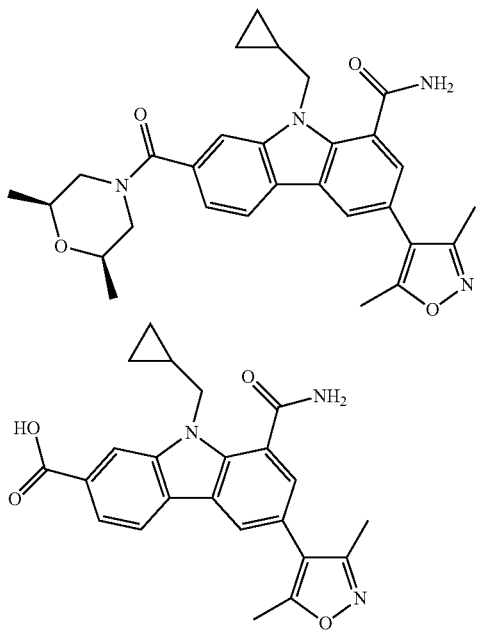

Step 2a: 8-carbamoyl-9-(cyclopropylmethyl)-6-(3,5-dimethylisoxazol-4-yl)-9H-carbazole-2-carboxylic acid To 8-carbamoyl-6-(3,5-dimethylisoxazol-4-yl)-9H-carbazole-2-carboxylic acid (800 mg, 2.290 mmol) was added acetone (1.0 mL), potassium carbonate (1266 mg, 9.16 mmol), 18C6 (60.5 mg, 0.229 mmol) and (bromomethyl) cyclopropane (3092 mg, 22.90 mmol). The reaction was allowed to heat to 70° C. After 24 hours, the reaction was concentrated. The residue was dissolved in MeOH (1.0 mL) and sodium hydroxide (2.186 mL, 21.86 mmol) was added. The reaction was stirred for two hours at room temperature. The reaction was concentrated, 1N HCl was added, and the precipitate was collected to give the desired product (970 mg).

HPLC Ret. Time=0.77, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 2 minute, then a 2-minute hold at 98% B; Flow: 0.8 mL/min. MS (ES): m/z=404 [M+H]$^+$.

To 8-carbamoyl-9-(cyclopropylmethyl)-6-(3,5-dimethylisoxazol-4-yl)-9H-carbazole-2-carboxylic acid (52 mg, 0.129 mmol) in DMF (1.0 mL) was added HCTU (154 mg, 0.387 mmol), DMAP (47.2 mg, 0.387 mmol) and cis-2,6-dimethylmorpholine (89 mg, 0.773 mmol). The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation. The yield of the final product was 28.3 mg, and its estimated purity by LCMS analysis was 95%. Two analytical LC/MS injections were used to determine the final purity.

Injection 1 conditions: Retention Time: 1.554 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=501 [M+H$^+$].

Injection 2 conditions: Retention Time: 1.548 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS(ES) m/z=501[M+H$^+$].

$^1$H NMR (400 MHz, DMSO-d$_6$) δ 8.35-8.31 (m, 2H), 8.25 (s, 1H), 7.82 (s, 1H), 7.75 (s, 1H), 7.45 (d, J=1.8 Hz, 1H), 7.26 (dd, J=7.9, 1.1 Hz, 1H), 4.55 (d, J=6.8 Hz, 2H), 3.61 (d, J=6.6 Hz, 2H), 2.48 (s, 2H), 2.31 (s, 2H), 1.30-0.86 (m, 7H), 0.37 (d, J=6.8 Hz, 4H).

Example 3

3-(3,5-dimethyl-4-isoxazolyl)-7-(4-morpholinylcarbonyl)-9H-carbazole-1-carboxamide

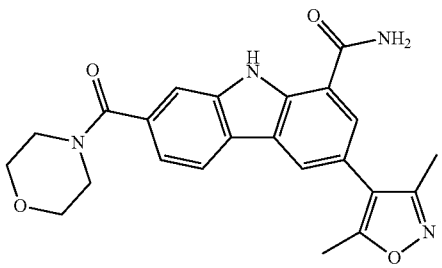

-continued

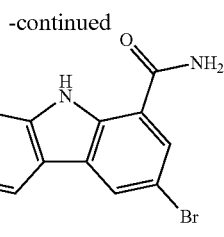

Step 3a: 3-bromo-7-(morpholine-4-carbonyl)-9H-carbazole-1-carboxamide

To 6-bromo-8-carbamoyl-9H-carbazole-2-carboxylic acid (542 mg, 1.302 mmol) in DMF (5.0 mL) was added HCTU (518 mg, 1.302 mmol), DMAP (477 mg, 3.90 mmol) and morpholine (680 mg, 7.81 mmol). After 2 hours 10% LiCl in water was added and the precipitate was collected. The solid was washed with water and air dried to give the desired product (385 mg).

HPLC Ret. Time=0.77, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 2 minute, then a 2-minute hold at 98% B; Flow: 0.8 mL/min. MS (ES): m/z=402 [M+H]$^+$.

To 3-bromo-7-(morpholine-4-carbonyl)-9H-carbazole-1-carboxamide (300 mg, 0.746 mmol) and 3,5-dimethyl-4-(4,4,5,5-tetramethyl-1,3,2-dioxaborolan-2-yl)isoxazole (233 mg, 1.044 mmol) was added DMF (5 ml). The reaction was degassed and then PdCl$_2$(dppf)-CH$_2$Cl$_2$Adduct (15.23 mg, 0.019 mmol) and aqueous tripotassium phosphate (0.746 ml, 2.237 mmol) were added. The reaction was degassed and heated at 80° C. overnight. Water was added and the precipitate was collected. The solid was washed with water and dried to give the desired product (320 mg).

HPLC Ret. Time=0.74, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 2 minute, then a 2-minute hold at 98% B; Flow: 0.8 mL/min. MS (ES): m/z=419 [M+H]$^+$.

Example 4

9-(cyclopropylmethyl)-3-(3,5-dimethyl-4-isoxazolyl)-7-(4-morpholinylcarbonyl)-9H-carbazole-1-carboxamide

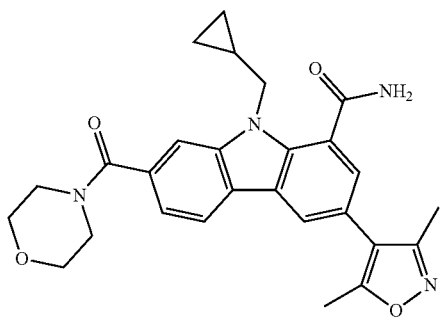 [SMILES: Cc1noc(C)c1-c1cc(C(N)=O)c2c(c1)c1ccc(C(=O)N3CCOCC3)cc1n2CC1CC1]

To 3-(3,5-dimethylisoxazol-4-yl)-7-(morpholine-4-carbonyl)-9H-carbazole-1-carboxamide (36 mg, 0.086 mmol) in Acetone (1 mL) was added (bromomethyl)cyclopropane (116 mg, 0.860 mmol), and potassium carbonate (47.6 mg, 0.344 mmol). The reaction was heated to 70° C. overnight. The reaction was filtered and concentrated.

The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation. The yield of the compound was 12.6 mg.

HPLC Ret. Time=0.78, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 2 minute, then a 2-minute hold at 98% B; Flow: 0.8 mL/min. MS (ES): m/z=473 [M+H]$^+$.

Example 5

3-(3,5-dimethyl-4-isoxazolyl)-9-(methylsulfonyl)-7-(4-morpholinylcarbonyl)-9H-carbazole-1-carboxamide

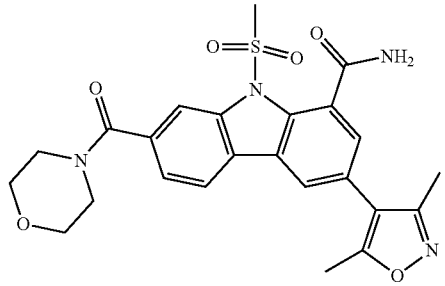 [SMILES: Cc1noc(C)c1-c1cc(C(N)=O)c2c(c1)c1ccc(C(=O)N3CCOCC3)cc1n2S(C)(=O)=O]

To 3-(3,5-dimethylisoxazol-4-yl)-7-(morpholine-4-carbonyl)-9H-carbazole-1-carboxamide (64 mg, 0.153 mmol) in DMF (1.0 mL) was added sodium hydride (60% dispersion in mineral oil, 18.35 mg, 0.459 mmol). The reaction was allowed to stir at room temperature for 15 min then methanesulfonyl chloride (0.012 mL, 0.153 mmol) was added. The reaction mixture was stirred at room temperature for 1 h. The reaction was quenched with a drop of water and filtered.

The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 99%. Two analytical LC/MS injections were used to determine the final purity.

Injection 1 conditions: Retention Time: 1.162 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=497 [M+H⁺].

Injection 2 conditions: Retention Time: 1.174 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS(ES) m/z=497 [M+H⁺].

Example 6

7-((4-cyano-1-piperidinyl)carbonyl)-3-(3,5-dimethyl-4-isoxazolyl)-9-(methylsulfonyl)-9H-carbazole-1-carboxamide

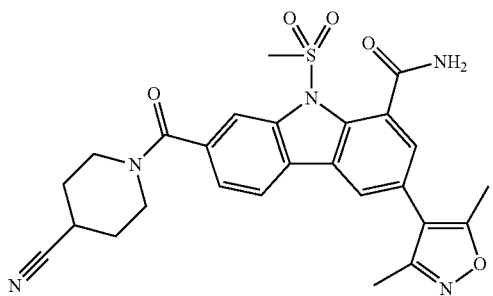

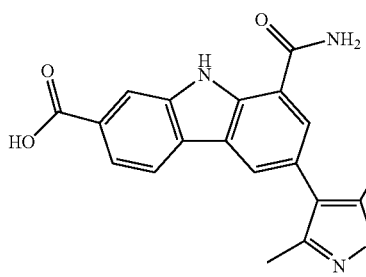

Step 6a: 8-carbamoyl-6-(3,5-dimethylisoxazol-4-yl)-9H-carbazole-2-carboxylic acid To a degassed solution of 6-bromo-8-carbamoyl-9H-carbazole-2-carboxylic acid (2 g, 6.00 mmol), (3,5-dimethylisoxazol-4-yl)boronic acid (1.269 g, 9.01 mmol) in DMF (60.0 ml) was added PdCl₂(dppf)-CH₂Cl₂ adduct (300 mg, 0.367 mmol) and K₂CO₃ (2.489 g, 18.01 mmol) under nitrogen. The reaction mixture was purged with nitrogen and heated at 95° C. for 2 h. The reaction mixture was filtered, and neutralized to pH ~7 with 1N aq. HCl. The reaction mixture was poured over 800 mL of ice and stirred overnight at room temp. The precipitate was filtered through at fritted funnel to give 8-carbamoyl-6-(3,5-dimethylisoxazol-4-yl)-9H-carbazole-2-carboxylic acid (2.42 g, 6.93 mmol, 115% yield). LC/MS; (M+H)'=350.1

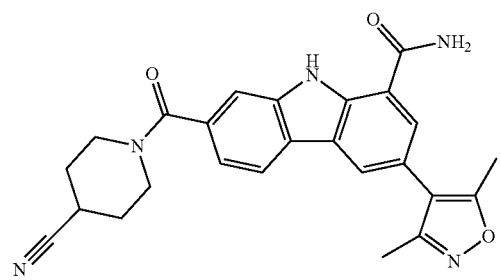 [SMILES: Cc1noc(C)c1-c1cc(C(N)=O)c2[nH]c3cc(C(=O)N4CCC(C#N)CC4)ccc3c2c1]

Step 6b: 7-(4-cyanopiperidine-1-carbonyl)-3-(3,5-dimethylisoxazol-4-yl)-9H-carbazole-1-carboxamide To a solution of 8-carbamoyl-6-(3,5-dimethylisoxazol-4-yl)-9H-carbazole-2-carboxylic acid (80 mg, 0.229 mmol) in DMF (2 mL) was added piperidine-4-carbonitrile (76 mg, 0.687 mmol) and DIPEA (0.120 mL, 0.687 mmol) followed by HOBT (105 mg, 0.687 mmol) and EDC (132 mg, 0.687 mmol). The reaction mixture was stirred at room temperature overnight. The reaction mixture was poured over ice water to give a precipitate. Filtration yielded 7-(4-cyanopiperidine-1-carbonyl)-3-(3,5-dimethylisoxazol-4-yl)-9H-carbazole-1-carboxamide (96 mg, 0.217 mmol, 95% yield) as a brown solid. LC/MS; (M+H)'=442.4

To a suspension of 7-(4-cyanopiperidine-1-carbonyl)-3-(3,5-dimethylisoxazol-4-yl)-9H-carbazole-1-carboxamide (46 mg, 0.104 mmol) in THF (2 mL) at room temperature was added KOtBu (1M in THF, 0.135 mL, 0.135 mmol). The reaction mixture turns yellow and was stirred for 5 min followed by addition of methanesulfonyl chloride (0.024 mL, 0.313 mmol). The reaction mixture was stirred at room temperature for 10 min then concentrated. The crude material was purified via preparative LC/MS with the following conditions: Column: Waters XBridge C18, 19×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 15 minutes, then a 5-minute hold at 100% B; Flow: 20 mL/min. Fractions containing the desired product were combined and dried via centrifugal evaporation.

The yield of the product was 3.9 mg, and its estimated purity by LCMS analysis was 89%. Two analytical LC/MS injections were used to determine the final purity.

Injection 1 conditions: Retention Time: 1.16 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=520 [M+H⁺].

Injection 2 conditions: Retention Time: 1.16 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS(ES) m/z=520 [M+H⁺].

The examples in Table 1 were synthesized by the same procedure given for Example 6:

TABLE 1

| # | Structure | Name | RT (min) | LC/MS (M + H)+ |
|---|---|---|---|---|
| 7 | 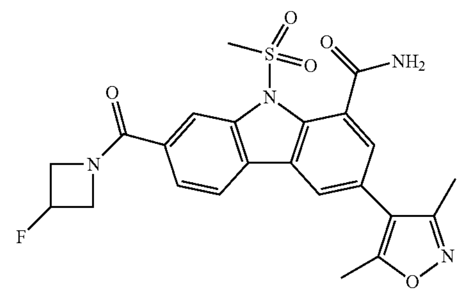 [SMILES: Cc1noc(C)c1-c1cc(C(N)=O)c2c(c1)c1ccc(C(=O)N3CC(F)C3)cc1n2S(C)(=O)=O] | 3-(3,5-dimethyl-4-isoxazolyl)-7-((3-fluoro-1-azetidinyl)carbonyl)-9-(methylsulfonyl)-9H-carbazole-1-carboxamide | 1.14[A] | 485.0 |
| 8 | 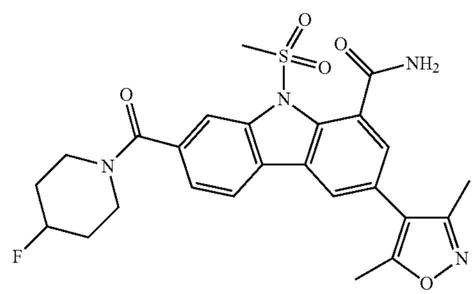 [SMILES: Cc1noc(C)c1-c1cc(C(N)=O)c2c(c1)c1ccc(C(=O)N3CCC(F)CC3)cc1n2S(C)(=O)=O] | 3-(3,5-dimethyl-4-isoxazolyl)-7-((4-fluoro-1-piperidinyl)carbonyl)-9-(methylsulfonyl)-9H-carbazole-1-carboxamide | 1.23[B] | 513.2 |
| 9 | 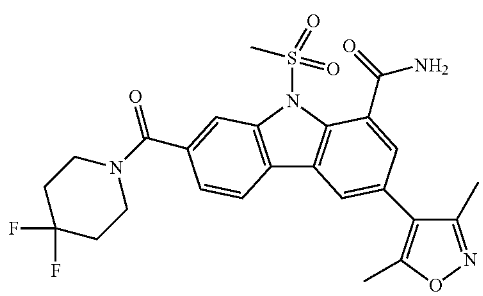 [SMILES: Cc1noc(C)c1-c1cc(C(N)=O)c2c(c1)c1ccc(C(=O)N3CCC(F)(F)CC3)cc1n2S(C)(=O)=O] | 7-((4,4-difluoro-1-piperidinyl)carbonyl)-3-(3,5-dimethyl-4-isoxazolyl)-9-(methylsulfonyl)-9H-carbazole-1-carboxamide | 1.37[B] | 531.1 |
| 10 | 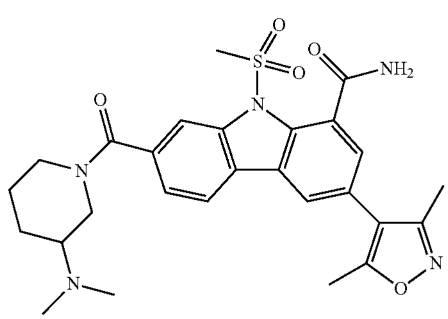 [SMILES: Cc1noc(C)c1-c1cc(C(N)=O)c2c(c1)c1ccc(C(=O)N3CCCC(N(C)C)C3)cc1n2S(C)(=O)=O] | 7-((3-(dimethylamino)-1-piperidinyl)carbonyl)-3-(3,5-dimethyl-4-isoxazolyl)-9-(methylsulfonyl)-9H-carbazole-1-carboxamide | 0.84[B] | 538.2 |
| 11 | 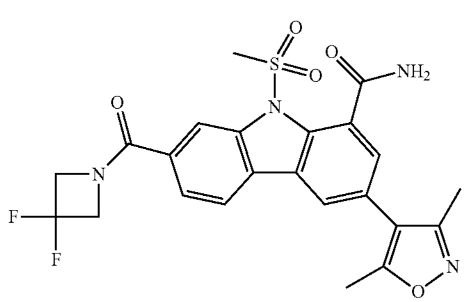 [SMILES: Cc1noc(C)c1-c1cc(C(N)=O)c2c(c1)c1ccc(C(=O)N3CC(F)(F)C3)cc1n2S(C)(=O)=O] | 7-((3,3-difluoro-1-azetidinyl)carbonyl)-3-(3,5-dimethyl-4-isoxazolyl)-9-(methylsulfonyl)-9H-carbazole-1-carboxamide | 1.27[B] | 503.1 |

TABLE 1-continued

| # | Structure | Name | RT (min) | LC/MS (M + H)+ |
|---|---|---|---|---|
| 12 | 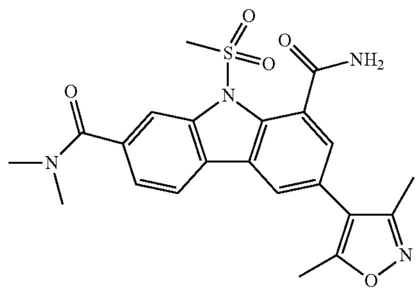 | 3-(3,5-dimethyl-4-isoxazolyl)-N7,N7-dimethyl-9-(methylsulfonyl)-9H-carbazole-1,7-dicarboxamide | 1.08[B] | 455.1 |
| 13 | 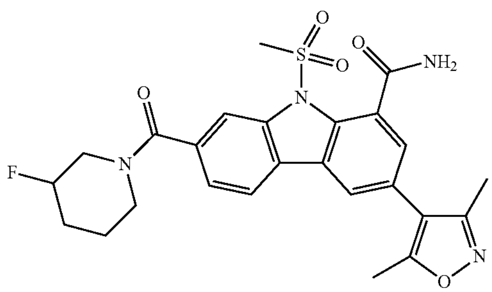 [SMILES: Cc1noc(C)c1-c1cc(C(N)=O)c2c(c1)c1ccc(C(=O)N3CCCC(F)C3)cc1n2S(C)(=O)=O] | 3-(3,5-dimethyl-4-isoxazolyl)-7-((3-fluoro-1-piperidinyl)carbonyl)-9-(methylsulfonyl)-9H-carbazole-1-carboxamide | 1.25[B] | 513.2 |
| 14 | 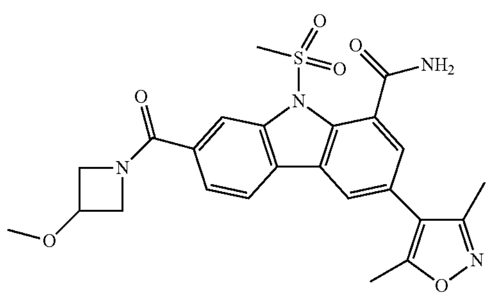 | 3-(3,5-dimethyl-4-isoxazolyl)-7-((3-methoxy-1-azetidinyl)carbonyl)-9-(methylsulfonyl)-9H-carbazole-1-carboxamide | 1.18[B] | 497.1 |
| 15 | 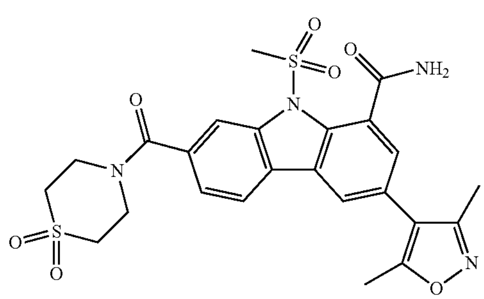 [SMILES: Cc1noc(C)c1-c1cc(C(N)=O)c2c(c1)c1ccc(C(=O)N3CCS(=O)(=O)CC3)cc1n2S(C)(=O)=O] | 3-(3,5-dimethyl-4-isoxazolyl)-7-((1,1-dioxido-4-thiomorpholinyl)carbonyl)-9-(methylsulfonyl)-9H-carbazole-1-carboxamide | 1.18[B] | 545.1 |
| 16 | 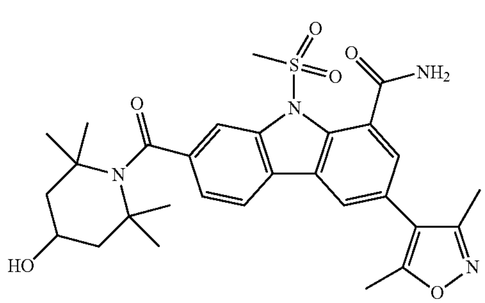 [SMILES: Cc1noc(C)c1-c1cc(C(N)=O)c2c(c1)c1ccc(C(=O)N3C(C)(C)CC(O)CC3(C)C)cc1n2S(C)(=O)=O] | 3-(3,5-dimethyl-4-isoxazolyl)-7-((4-hydroxy-2,2,6,6-tetramethyl-1-piperidinyl)carbonyl)-9-(methylsulfonyl)-9H-carbazole-1-carboxamide | 1.15[B] | 567.2 |

TABLE 1-continued

| # | Structure | Name | RT (min) | LC/MS (M + H)+ |
|---|---|---|---|---|
| 17 | 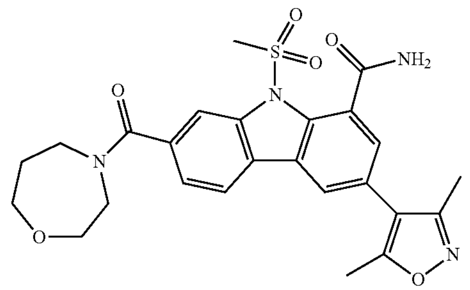 [SMILES: Cc1noc(C)c1-c1cc(C(N)=O)c2c(c1)c1ccc(C(=O)N3CCCOCC3)cc1n2S(C)(=O)=O] | 3-(3,5-dimethyl-4-isoxazolyl)-9-(methylsulfonyl)-7-(1,4-oxazepan-4-ylcarbonyl)-9H-carbazole-1-carboxamide | 1.11[A] | 511.2 |
| 18 | 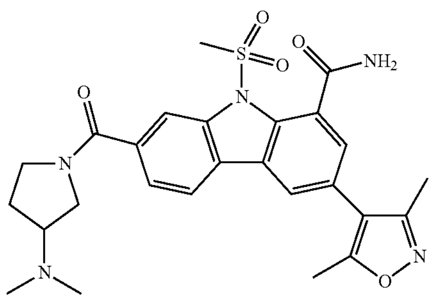 | 7-((3-(dimethylamino)-1-pyrrolidinyl)carbonyl)-3-(3,5-dimethyl-4-isoxazolyl)-9-(methylsulfonyl)-9H-carbazole-1-carboxamide | 0.97[A] | 524.2 |
| 19 | 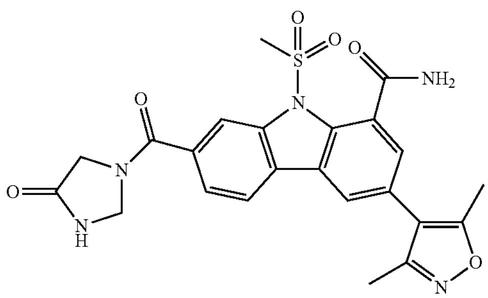 [SMILES: Cc1noc(C)c1-c1cc(C(N)=O)c2c(c1)c1ccc(C(=O)N3CNC(=O)C3)cc1n2S(C)(=O)=O] | 3-(3,5-dimethyl-4-isoxazolyl)-9-(methylsulfonyl)-7-((4-oxo-1-imidazolidinyl)carbonyl)-9H-carbazole-1-carboxamide | 1.19[A] | 496.1 |

HPLC Conditions: [A]: Column: Waters Acquity UPLC BEH C18, 2.1 x 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. [B]: Column: Waters Acquity UPLC BEH C18, 2.1 x 50 mm, 1.7-μm particles; Mobile Phase A: 5:95 acetonitrile:water with 0.05% TFA; Mobile Phase B: 95.5 acetonitrile:water with 0.05% TFA; Temperature: 50° C.; Gradient: 0-100% B over 3 minutes, then a 0.75-minute hold at 100% B; Flow: 1.11 mL/min

Example 20

7-((4-cyano-1-piperidinyl)carbonyl)-9-(cyclopropylsulfonyl)-3-(3,5-dimethyl-4-isoxazolyl)-9H-carbazole-1-carboxamide

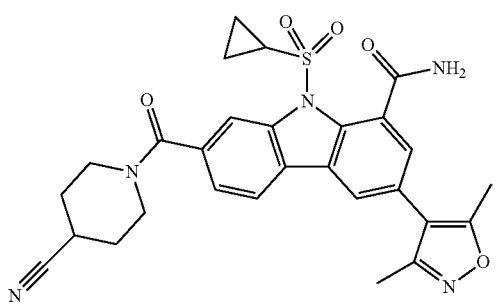 [SMILES: Cc1noc(C)c1-c1cc(C(N)=O)c2c(c1)c1ccc(C(=O)N3CCC(C#N)CC3)cc1n2S(=O)(=O)C1CC1]

To a suspension of 7-(4-cyanopiperidine-1-carbonyl)-3-(3,5-dimethylisoxazol-4-yl)-9H-carbazole-1-carboxamide (20 mg, 0.045 mmol) in THF (2 mL) at room temperature was added KOtBu (1M in THF, 0.059 mL, 0.059 mmol). The reaction mixture turns yellow and was stirred for 5 min followed by addition of cyclopropanesulfonyl chloride (19.11 mg, 0.136 mmol). The reaction mixture was stirred at room temperature for 10 min then concentrated. The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 0-100% B over 25 minutes, then a 5-minute hold at 100% B; Flow: 20 mL/min. Fractions containing the desired product were combined and dried via centrifugal evaporation. The yield of the product was 2.3 mg, and its estimated purity by LCMS analysis was 93%. Two analytical LC/MS injections were used to determine the final purity.

Injection 1 conditions: Retention Time: 1.20 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=546 [M+H+].

Injection 2 conditions: Retention Time: 1.20 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS(ES) m/z=546 [M+H$^+$].

The examples in Table 2 were synthesized by the same procedure given for Example 20.

TABLE 2

| # | Structure | Name | RT (min) | LC/MS (M + H)$^+$ |
|---|---|---|---|---|
| 21 | 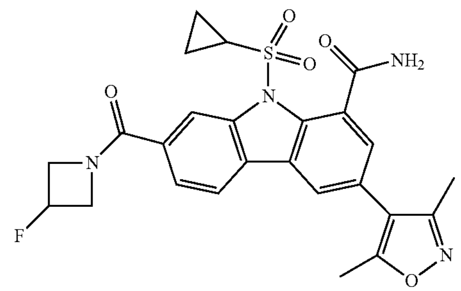 [SMILES: Cc1noc(C)c1-c1cc(C(N)=O)c2c(c1)c1ccc(C(=O)N3CC(F)C3)cc1n2S(=O)(=O)C1CC1] | 9-(cyclopropylsulfonyl)-3-(3,5-dimethyl-4-isoxazolyl)-7-((3-fluoro-1-azetidinyl)carbonyl)-9H-carbazole-1-carboxamide | 1.23$^A$ | 511.1 |
| 22 | 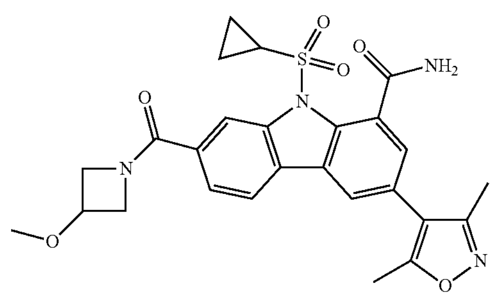 | 9-(cyclopropylsulfonyl)-3-(3,5-dimethyl-4-isoxazolyl)-7-((3-methoxy-1-azetidinyl)carbonyl)-9H-carbazole-1-carboxamide | 1.17$^A$ | 522.2 |
| 23 | 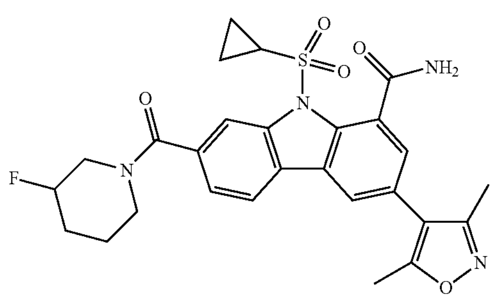 [SMILES: Cc1noc(C)c1-c1cc(C(N)=O)c2c(c1)c1ccc(C(=O)N3CCCC(F)C3)cc1n2S(=O)(=O)C1CC1] | 9-(cyclopropylsulfonyl)-3-(3,5-dimethyl-4-isoxazolyl)-7-((3-fluoro-1-piperidinyl)carbonyl)-9H-carbazole-1-carboxamide | 1.30$^B$ | 539.2 |
| 24 | 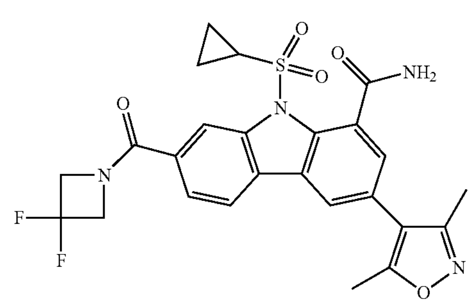 [SMILES: Cc1noc(C)c1-c1cc(C(N)=O)c2c(c1)c1ccc(C(=O)N3CC(F)(F)C3)cc1n2S(=O)(=O)C1CC1] | 9-(cyclopropylsulfonyl)-7-((3,3-difluoro-1-azetidinyl)carbonyl)-3-(3,5-dimethyl-4-isoxazolyl)-9H-carbazole-1-carboxamide | 1.34$^B$ | 529.1 |

TABLE 2-continued

| # | Structure | Name | RT (min) | LC/MS (M + H)+ |
|---|---|---|---|---|
| 25 | 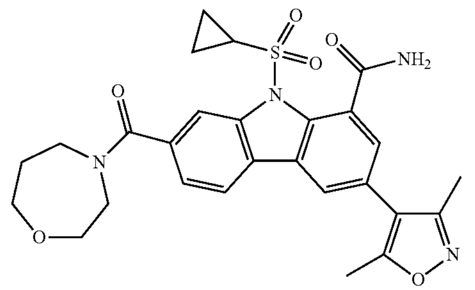 [SMILES: Cc1noc(C)c1-c1cc(C(N)=O)c2c(c1)c1ccc(C(=O)N3CCCOCC3)cc1n2S(=O)(=O)C1CC1] | 9-(cyclopropylsulfonyl)-3-(3,5-dimethyl-4-isoxazolyl)-7-(1,4-oxazepan-4-ylcarbonyl)-9H-carbazole-1-carboxamide | 1.15[B] | 537.2 |
| 26 | 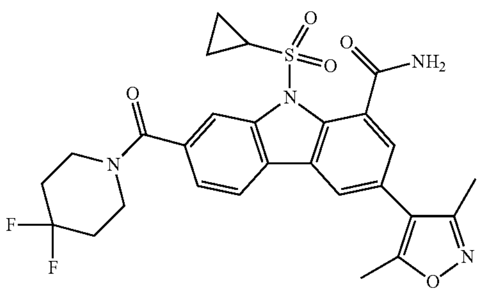 [SMILES: Cc1noc(C)c1-c1cc(C(N)=O)c2c(c1)c1ccc(C(=O)N3CCC(F)(F)CC3)cc1n2S(=O)(=O)C1CC1] | 9-(cyclopropylsulfonyl)-7-((4,4-difluoro-1-piperidinyl)carbonyl)-3-(3,5-dimethyl-4-isoxazolyl)-9H-carbazole-1-carboxamide | 1.43[B] | 557.2 |

HPLC Conditions: [A]: Column: Waters Acquity UPLC BEH C18, 2.1 x 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. [B]: Column: Waters Acquity UPLC BEH C18, 2.1 x 50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min Example 27 tert-butyl(8-carbamoyl-9-(cyclopropylmethyl)-6-(3,5-dimethyl-4-isoxazolyl)-9H-carbazol-2-yl)carbamate

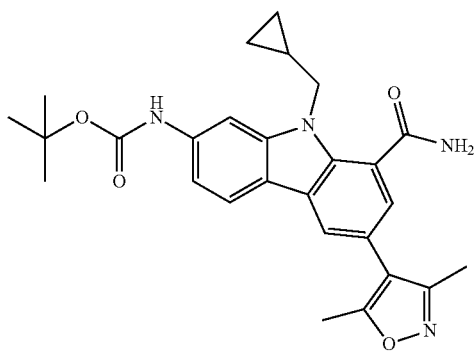

Step 27a: Cyclopropylmethyl 6-bromo-8-carbamoyl-9-(cyclopropylmethyl)-9H-carbazole-2-carboxylate To 6-bromo-8-carbamoyl-9H-carbazole-2-carboxylic acid (528 mg, 1.585 mmol) was added acetone (1.0 mL), potassium carbonate (876 mg, 6.34 mmol), 18C6 (41.9 mg, 0.158 mmol) and (bromomethyl)cyclopropane (2140 mg, 15.85 mmol). The reaction was allowed to heat to 50° C. overnight. The reaction mixture was concentrated and MeOH (1.0 mL), water (1.0 ml) and 50% NaOH (0.792 mL, 7.92 mmol) were added. The reaction was allowed to stir at room temperature for 8 hours, partially concentrated, diluted with 1N HCl (5.0 ml) and filtered. The solid was washed with water (100 ml) and dried through a stream of air overnight to give cyclopropylmethyl 6-bromo-8-carbamoyl-9-(cyclopropylmethyl)-9H-carbazole-2-carboxylate (408 mg, 62%). HPLC Ret. Time=0.84, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=416 [M+H]+.

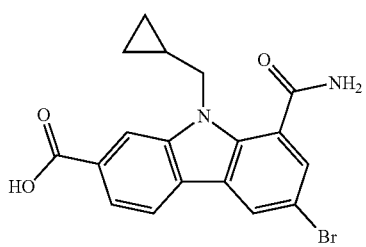

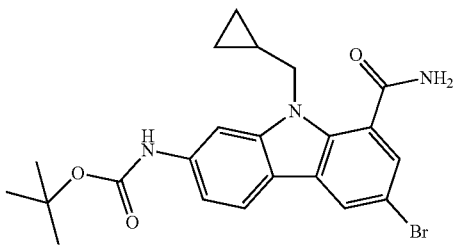 [SMILES: CC(C)(C)OC(=O)Nc1ccc2c3cc(Br)cc(C(N)=O)c3n(CC3CC3)c2c1]

Step 27b: tert-butyl 6-bromo-8-carbamoyl-9-(cyclopropylmethyl)-9H-carbazol-2-yl carbamate 6-bromo-8-carbamoyl-9-(cyclopropylmethyl)-9H-carbazole-2-carboxylic acid (3) (0.050 g, 0.129 mmol) was mixed with 4 A molecular sieves (0.100 g, 0.129 mmol) in dioxane (0.646 ml). To the mixture was added Et$_3$N (0.044 ml, 0.319 mmol) and diphenyl phosphorazidate (0.069 ml, 0.319 mmol). The mixture was stirred at 55° C. for 2 hours. tBuOH (0.123 ml, 1.291 mmol) was added to the mixture and stirred at 80° C. for 16 hours. The mixture was concentrated, diluted with 0.4 ml of DCM and purified on a 12G ISCO column using 0-100% ethyl acetate/heptane. Following concentration, collected tert-butyl 6-bromo-8-carbamoyl-9-(cyclopropylmethyl)-9H-carbazol-2-ylcarbamate as an off-white solid (11.8 mg, 20%). HPLC Ret. Time=0.97, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes, then a 0.75-minute hold at 100% B; Flow: 1.11 mL/min. MS (ES): m/z=459 [M+H]$^+$.

To tert-butyl(6-bromo-8-carbamoyl-9-(cyclopropylmethyl)-9H-carbazol-2-yl)carbamate (18.50 mg, 0.040 mmol), 3,5-dimethyl-4-(4,4,5,5-tetramethyl-1,3,2-dioxaborolan-2-yl)isoxazole (13.51 mg, 0.061 mmol) was added DMF (404 μl). Reaction was degassed and then PdCl$_2$(dppf)-CH$_2$Cl$_2$Adduct (1.648 mg, 2.018 μmol) and 3.0M aqueous tribasic potassium phosphate (40.4 μl, 0.121 mmol) solution were added. Reaction was degassed 3 times with nitrogen gas and heated at 80° C. for 2 hours. The solvent was removed in-vacuo and the residue was diluted with DCM (3.0 ml). Water was added and the layers were separated. The organic layer was collected, washed with 1.0 ml of brine, dried over Na$_2$SO$_4$, filtered and concentrated. The residue was dissolved in 0.5 ml of DCM and loaded onto a 4G ISCO column. Purification was done eluting with 0-75% ethyl acetate/Heptane over 12 minutes. Following concentration, collected tert-butyl(8-carbamoyl-9-(cyclopropylmethyl)-6-(3,5-dimethyl-4-isoxazolyl)-9H-carbazol-2-yl)carbamate as a whitish solid (16.7 mg, 88%). HPLC Ret. Time=1.01, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes, then a 0.75-minute hold at 100% B; Flow: 1.11 mL/min. MS (ES): m/z=475 [M+H]$^+$.

Example 28

7-amino-9-(cyclopropylmethyl)-3-(3,5-dimethyl-4-isoxazolyl)-9H-carbazole-1-carboxamide

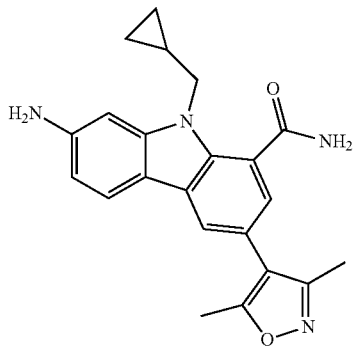 [SMILES: Cc1noc(C)c1-c1cc(C(N)=O)c2c(c1)c1ccc(N)cc1n2CC1CC1]

In a 2 dram vial was added tert-butyl(8-carbamoyl-9-(cyclopropylmethyl)-6-(3,5-dimethylisoxazol-4-yl)-9H-carbazol-2-yl)carbamate (0.146 g, 0.308 mmol), DCM (1 mL) and TFA (1 mL, 12.98 mmol). The reaction was stirred for 30 minutes at room temperature then concentrated and placed under vacuum to remove TFA. The residue was diluted with DCM (10.0 ml). Water was added and the layers were separated. The organic layer was collected, washed with 1.0 ml of brine, dried over Na$_2$SO$_4$, filtered and concentrated to give 7-amino-9-(cyclopropylmethyl)-3-(3,5-dimethyl-4-isoxazolyl)-9H-carbazole-1-carboxamide (105 mg, 91%). HPLC Ret. Time=0.63, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes, then a 0.75-minute hold at 100% B; Flow: 1.11 mL/min. MS (ES): m/z=375 [M+H]$^+$.

Example 29

7-acetamido-9-(cyclopropylmethyl)-3-(3,5-dimethyl-4-isoxazolyl)-9H-carbazole-1-carboxamide

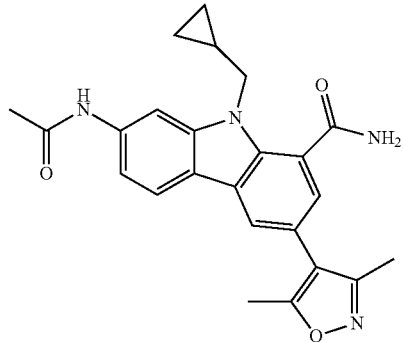 [SMILES: CC(=O)Nc1ccc2c3cc(-c4c(C)noc4C)cc(C(N)=O)c3n(CC3CC3)c2c1]

In a 2 dram vial was added 7-amino-9-(cyclopropylmethyl)-3-(3,5-dimethylisoxazol-4-yl)-9H-carbazole-1-carboxamide (0.020 g, 0.053 mmol), DCM (1 mL), pyridine (0.042 g, 0.534 mmol), N,N-dimethylpyridin-4-amine (0.326 mg, 2.67 μmol) and acetyl chloride (0.021 g, 0.267 mmol). The reaction was stirred at room temperature for 0.5 hours. The reaction was concentrated, diluted with DMSO, filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 7-acetamido-9-(cyclopropylmethyl)-3-(3,5-dimethyl-4-isoxazolyl)-9H-carbazole-1-carboxamide (2.5 mg, 11%). Two analytical LC/MS injections were used to determine the final purity.

Injection 1 conditions: HPLC Ret. Time=1.188, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.;

Gradient: 0-100% B over 3 minutes, then a 0.75-minute hold at 100% B; Flow: 1.11 mL/min. (HPLC Ret. Time$^{Method\ b}$). MS (ES): m/z=417 [M+H]$^+$.

Injection 2 conditions: HPLC Ret. Time=1.291, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=417 [M+H]$^+$. $^1$H NMR (500 MHz, METHANOL-d$_4$) δ 8.12 (d, J=1.5 Hz, 1H), 8.03-7.99 (m, 2H), 7.61 (s, 1H), 7.39 (d, J=1.5 Hz, 1H), 7.24 (dd, J=8.4, 2.0 Hz, 1H), 4.46 (d, J=6.4 Hz, 2H), 4.34 (s, 1H), 3.01 (s, 1H), 2.48-2.44 (m, 3H), 2.31 (s, 3H), 2.21 (s, 3H), 1.34-1.24 (m, 1H), 0.48-0.40 (m, 4H).

Example 30

9-(cyclopropylmethyl)-3-(3,5-dimethyl-4-isoxazolyl)-7-(di-1,3-thiazol-2-ylamino)-9H-carbazole-1-carboxamide

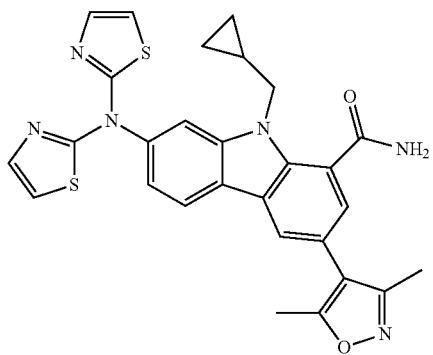 [SMILES: Cc1noc(C)c1-c1cc(C(N)=O)c2c(c1)c1ccc(N(c3nccs3)c3nccs3)cc1n2CC1CC1]

In a 5 mL screw top vial was added 7-amino-9-(cyclopropylmethyl)-3-(3,5-dimethylisoxazol-4-yl)-9H-carbazole-1-carboxamide (0.022 g, 0.059 mmol), cesium carbonate (0.057 g, 0.176 mmol), 2-bromothiazole (0.014 g, 0.088 mmol) and Chloro(2-dicyclohexylphosphino-2',4',6'-triisopropyl-1,1'-biphenyl)[2-(2'-amino-1,1'-biphenyl)]palladium(II) (4.38 mg, 5.88 μmol) in t-butanol (1 mL) to give a suspension. The reaction was pump/purged with nitrogen three times. It was then heated to 80° C. for 3 hours. The volatiles were removed under a stream of nitrogen and the residue was diluted with 1.0 ml of DMSO and filtered through a 5-micron filter disc. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 15-100% B over 15 minutes, then a 5-minute hold at 100% B; Flow: 20 mL/min. Fractions containing the desired product were combined and dried via centrifugal evaporation (0.8 mg, 2.3%). Two analytical LC/MS injections were used to determine the final purity.

Injection 1 conditions: HPLC Ret. Time=1.87, column: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=541 [M+H]$^+$.

Injection 2 conditions: HPLC Ret. Time=1.78, column: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=541 [M+H]$^+$.

Example 31

9-(cyclopropylmethyl)-3-(3,5-dimethyl-4-isoxazolyl)-7-((ethylcarbamoyl)amino)-9H-carbazole-1-carboxamide

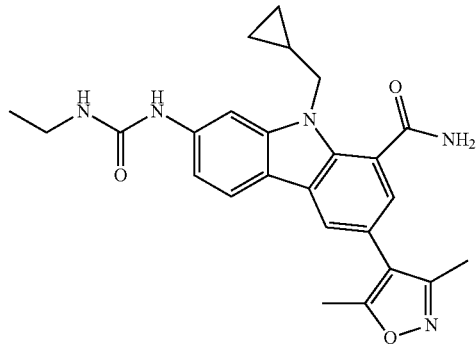 [SMILES: CCNC(=O)Nc1ccc2c3cc(-c4c(C)noc4C)cc(C(N)=O)c3n(CC3CC3)c2c1]

In a 2 dram vial was added 7-amino-9-(cyclopropylmethyl)-3-(3,5-dimethylisoxazol-4-yl)-9H-carbazole-1-carboxamide (0.030 g, 0.080 mmol), DCM (1 mL), pyridine (1.0 ml), catalytic DMAP and isocyanatoethane (0.028 g, 0.401 mmol). After 2 hours 15 minutes, the reaction mixture was concentrated, diluted with DMSO, and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-3-(3,5-dimethyl-4-isoxazolyl)-7-((ethylcarbamoyl)amino)-9H-carbazole-1-carboxamide (3.2 mg, 8.8%). Two analytical LC/MS injections were used to determine the final purity.

Injection 1 conditions: HPLC Ret. Time=1.318, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=446 [M+H]$^+$.

Injection 2 conditions: HPLC Ret. Time=1.351, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=446 [M+H]+. 1H NMR (500 MHz, METHANOL-d4) d 7.98-7.95 (m, 1H), 7.94 (s, 1H), 7.39-7.29 (m, 1H), 7.26-7.14 (m, 1H), 7.01 (dd, J=8.4, 2.0 Hz, 1H), 4.45 (d, J=6.4 Hz, 2H), 3.29 (q, J=7.4 Hz, 2H), 2.46 (s, 3H), 2.31 (s, 3H), 1.35-1.27 (m, 1H), 1.22-1.17 (m, 3H), 0.49-0.38 (m, 4H)

Example 32

Ethyl(8-carbamoyl-9-(cyclopropylmethyl)-6-(3,5-dimethyl-4-isoxazolyl)-9H-carbazol-2-yl)carbamate

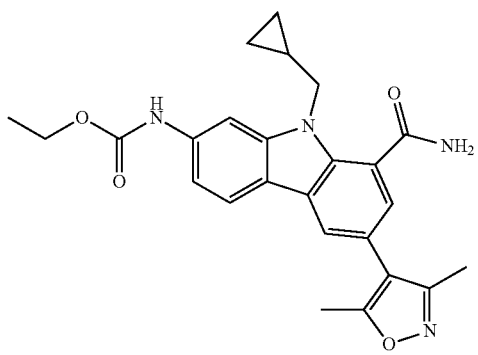 [SMILES: CCOC(=O)Nc1ccc2c3cc(-c4c(C)noc4C)cc(C(N)=O)c3n(CC3CC3)c2c1]

In a 2 dram vial was added 7-amino-9-(cyclopropylmethyl)-3-(3,5-dimethylisoxazol-4-yl)-9H-carbazole-1-carboxamide (0.025 g, 0.067 mmol), DCM (1 mL), pyridine (0.053 g, 0.668 mmol) and ethyl carbonochloridate (0.036 g, 0.334 mmol). The reaction was stirred at room temperature for 0.5 hrs. The reaction mixture was concentrated, diluted with DMSO, filtered through a 0.45 um nylon membrane syringe filter. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation to give ethyl(8-carbamoyl-9-(cyclopropylmethyl)-6-(3,5-dimethyl-4-isoxazolyl)-9H-carbazol-2-yl)carbamate (5.9 mg, 19%). Two analytical LC/MS injections were used to determine the final purity.

Injection 1 conditions: HPLC Ret. Time=1.588, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=447 [M+H]+.

Injection 2 conditions: HPLC Ret. Time=1.588, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=447 [M+H]+. 1H NMR (500 MHz, methanol-d4) d 8.01-7.96 (m, 1H), 7.95-7.90 (m, 1H), 7.62 (s, 1H), 7.38 (d, J=2.0 Hz, 1H), 7.16 (dd, J=8.4, 1.5 Hz, 1H), 4.46 (d, J=6.9 Hz, 2H), 4.35 (br. s., 1H), 4.25 (q, J=7.1 Hz, 2H), 2.46 (s, 3H), 2.31 (s, 3H), 1.36 (t, J=6.9 Hz, 3H), 1.33-1.26 (m, 1H), 0.49-0.39 (m, 4H).

Example 33

Methyl(8-carbamoyl-9-(cyclopropylmethyl)-6-(3,5-dimethyl-4-isoxazolyl)-9H-carbazol-2-yl)carbamate

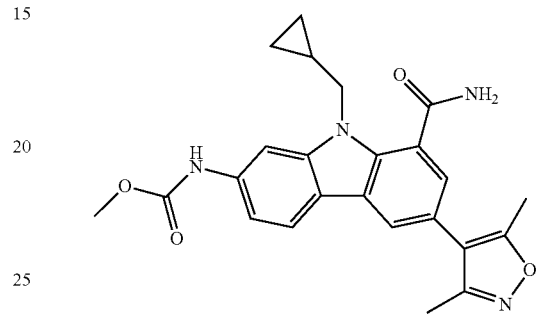

The above titled compound was prepared from methyl carbonochloridate according to the conditions described for the preparation of Example 32, ethyl(8-carbamoyl-9-(cyclopropylmethyl)-6-(3,5-dimethyl-4-isoxazolyl)-9H-carbazol-2-yl)carbamate. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 100%. Two analytical LC/MS injections were used to determine the final purity.

Injection 1 conditions: Retention Time: 1.457. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=453 [M+H+].

Injection 2 conditions: Retention Time: 1.456 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Example 34

7-bromo-9-(cyclopropylmethyl)-3-(3,5-dimethyl-4-isoxazolyl)-9H-carbazole-1-carboxamide

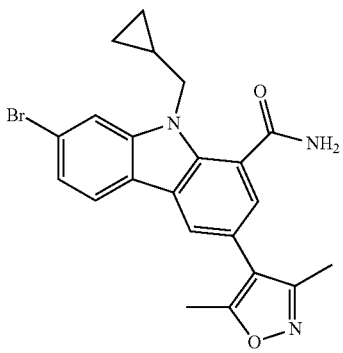 [SMILES: Cc1noc(C)c1-c1cc(C(N)=O)c2c(c1)c1ccc(Br)cc1n2CC1CC1]

and

Example 35

6,7-dibromo-9-(cyclopropylmethyl)-3-(3,5-dimethyl-4-isoxazolyl)-9H-carbazole-1-carboxamide

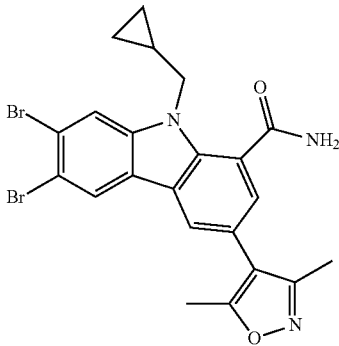 [SMILES: Cc1noc(C)c1-c1cc(C(N)=O)c2c(c1)c1cc(Br)c(Br)cc1n2CC1CC1]

In a 2 dram vial was added 7-amino-9-(cyclopropylmethyl)-3-(3,5-dimethyl-4-isoxazolyl)-9H-carbazole-1-carboxamide (0.035 g, 0.093 mmol), Acetonitrile (0.467 ml), copper(II) bromide (0.025 g, 0.112 mmol) and drop-wise, 2-methyl-2-nitrosopropane (0.012 g, 0.126 mmol). The reaction was stirred at room temperature for 8 hrs. The reaction was quenched with 1.0 ml of 10% sodium sulfite solution and concentrated. 10 mg of the crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 5-minute hold at 100% B; Flow: 20 mL/min. Fractions containing the desired product were combined and dried via centrifugal evaporation to give 7-bromo-9-(cyclopropylmethyl)-3-(3,5-dimethyl-4-isoxazolyl)-9H-carbazole-1-carboxamide (0.5 mg, 1.16%). Two analytical LC/MS injections were used to determine the final purity.

Injection 1 conditions: HPLC Ret. Time=1.93, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=438 [M+H]$^+$.

Injection 2 conditions: HPLC Ret. Time=1.941, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=438 [M+H]$^+$. $^1$H NMR (500 MHz, METHANOL-d$_4$) d 8.25 (d, J=2.0 Hz, 1H), 8.06 (d, J=2.0 Hz, 1H), 7.61-7.58 (m, 2H), 7.49-7.44 (m, 3H), 4.49 (d, J=6.9 Hz, 2H), 2.47 (s, 3H), 2.32 (s, 3H), 1.26 (br. s., 1H), 0.49-0.42 (m, 2H), 0.40-0.33 (m, 2H).

The second product, 6,7-dibromo-9-(cyclopropylmethyl)-3-(3,5-dimethyl-4-isoxazolyl)-9H-carbazole-1-carboxamide was purified via preparative HPLC using the following conditions: Phenomenex Luna column 5 u, 100 A°, 21.2×100 mm, 40-100% Solvent B, (Solvent A (90% water, 10% methanol, 0.1% TFA), Solvent B (10% water, 90% methanol, 0.1% TFA), 10 min gradient, 15 minute run, 25 mL/min). Following concentration of the solvent via rotoevaporation, 6,7-dibromo-9-(cyclopropylmethyl)-3-(3,5-dimethyl-4-isoxazolyl)-9H-carbazole-1-carboxamide was collected as a yellow solid (10.0 mg, 20%). An analytical LC/MS injection was used to determine the final purity. Injection conditions: HPLC Ret. Time=1.09, HPLC Ret. Time=1.09, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=516 [M+H]$^+$. $^1$H NMR (400 MHz, DMSO-d$_6$) δ 8.78 (s, 1H), 8.41 (d, J=1.8 Hz, 1H), 8.27 (s, 1H), 8.22 (s, 1H), 7.85 (s, 1H), 7.48 (d, J=1.8 Hz, 1H), 4.52 (d, J=7.0 Hz, 2H), 2.54-2.48 (m, 3H), 2.33 (s, 3H), 1.30-1.18 (m, 1H), 0.38-0.33 (m, 1H), 0.41-0.33 (m, 3H).

Example 36

9-(cyclopropylmethyl)-3-(3,5-dimethyl-4-isoxazolyl)-7-(4-pyridinyl)-9H-carbazole-1-carboxamide

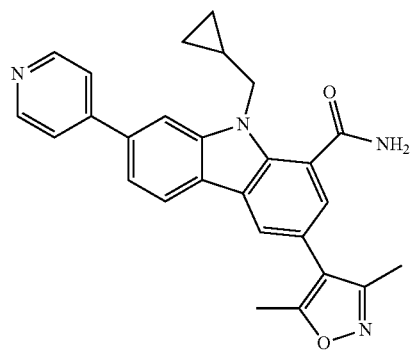 [SMILES: Cc1noc(C)c1-c1cc(C(N)=O)c2c(c1)c1ccc(-c3ccncc3)cc1n2CC1CC1]

To 7-bromo-9-(cyclopropylmethyl)-3-(3,5-dimethyl-4-isoxazolyl)-9H-carbazole-1-carboxamide (0.025 g, 0.057 mmol), 4-(4,4,5,5-tetramethyl-1,3,2-dioxaborolan-2-yl) pyridine (0.029 g, 0.143 mmol) was added THF (0.570 ml). The reaction was degassed and then [1,1'-Bis(di-tert-butyl-phosphino)ferrocene]dichloropalladium(II) (1.859 mg, 2.85 μmol) and 3.0M aqueous tribasic potassium phosphate (0.057 ml, 0.171 mmol) solution were added. The reaction was degassed and back-filled with nitrogen gas three times. The mixture was set to heat at 60° C. for 30 minutes. The reaction was concentrated, diluted with DMSO and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-3-(3,5-dimethyl-4-isoxazolyl)-7-(4-pyridinyl)-9H-carbazole-1-carboxamide (2.6 mg, 9.2%). Two analytical LC/MS injections were used to determine the final purity.

Injection 1 conditions: HPLC Ret. Time=1.514, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=437 [M+H]$^+$.

Injection 2 conditions: HPLC Ret. Time=1.419, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=437 [M+H]$^+$. $^1$H NMR (500 MHz, methanol-$d_4$) d 8.74-8.67 (m, 2H), 8.26 (d, J=1.5 Hz, 1H), 8.23 (d, J=6.4 Hz, 2H), 8.04 (dd, J=8.4, 2.0 Hz, 1H), 7.76 (d, J=8.9 Hz, 1H), 7.62 (s, 2H), 7.55 (d, J=1.5 Hz, 1H), 4.59 (d, J=6.9 Hz, 2H), 2.50 (s, 3H), 2.35 (s, 3H), 1.33 (br. s., 1H), 0.53-0.39 (m, 4H).

Example 37

9-(cyclopropylmethyl)-3-(3,5-dimethyl-4-isoxazolyl)-7-(methylamino)-9H-carbazole-1-carboxamide

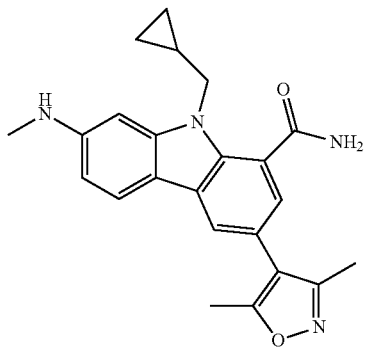

and

Example 38

9-(cyclopropylmethyl)-7-(dimethylamino)-3-(3,5-dimethyl-4-isoxazolyl)-9H-carbazole-1-carboxamide

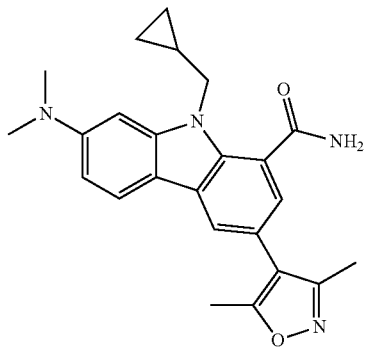

In a 2 dram vial was added 7-amino-9-(cyclopropylmethyl)-3-(3,5-dimethyl-4-isoxazolyl)-9H-carbazole-1-carboxamide (0.020 g, 0.053 mmol), THF (1.0 mL), Na$_2$CO$_3$ (0.023 g, 0.214 mmol) and iodomethane (0.015 g, 0.107 mmol). The reaction was stirred at 50° C. for 4 hours, and then it was stirred at room temperature overnight. The reaction was quenched with water (0.1 ml), concentrated, diluted with DMSO and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min.

Fractions containing each of the desired products were combined and dried via centrifugal evaporation to give final compounds:

Example 37, 9-(cyclopropylmethyl)-3-(3,5-dimethyl-4-isoxazolyl)-7-(methylamino)-9H-carbazole-1-carboxamide (1.6 mg, 7.7%). Two analytical LC/MS injections were used to determine the final purity.

Injection 1 conditions: HPLC Ret. Time=1.515, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=389 [M+H]$^+$.

Injection 2 conditions: HPLC Ret. Time=1.085, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=389 [M+H]$^+$. $^1$H NMR (500 MHz, METHANOL-$d_4$) d 7.97 (s, 1H), 7.90-7.79 (m, 2H), 7.60 (s, 1H), 7.26 (d, J=1.5 Hz, 1H), 6.70-6.59 (m, 2H), 4.42 (d, J=6.9 Hz, 2H), 4.32 (br. s., 1H), 2.93 (s, 3H), 2.45 (s, 3H), 2.30 (s, 3H), 1.35-1.19 (m, 1H), 0.50-0.35 (m, 4H).

Example 38, 9-(cyclopropylmethyl)-7-(dimethylamino)-3-(3,5-dimethyl-4-isoxazolyl)-9H-carbazole-1-carboxamide (4.1 mg, 18.7%). Two analytical LC/MS injections were used to determine the final purity.

Injection 1 conditions: HPLC Ret. Time=1.768, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=403 [M+H]$^+$.

Injection 2 conditions: HPLC Ret. Time=1.133, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=403 [M+H]$^+$. $^1$H NMR (500 MHz, METHANOL-d$_4$) δ 7.91 (d, J=8.4 Hz, 1H), 7.89 (d, J=2.0 Hz, 1H), 7.60 (s, 1H), 7.28 (d, J=2.0 Hz, 1H), 6.82 (dd, J=8.4, 2.0 Hz, 1H), 6.74 (d, J=2.0 Hz, 1H), 4.43 (d, J=6.4 Hz, 2H), 4.31 (s, 1H), 3.09 (s, 6H), 2.45 (s, 3H), 2.31 (s, 3H), 1.34-1.22 (m, 1H), 0.50-0.35 (m, 4H).

Example 39

7-(cyclopentylmethylamino)-9-(cyclopropylmethyl)-3-(3,5-dimethyl-4-isoxazolyl)-9H-carbazole-1-carboxamide

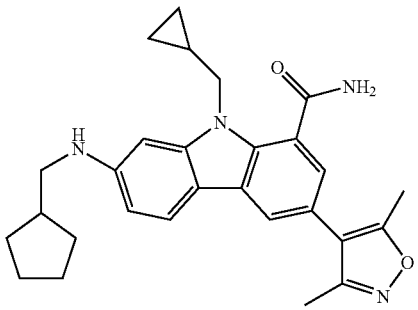 [SMILES: Cc1noc(C)c1-c1cc(C(N)=O)c2c(c1)c1ccc(NCC3CCCC3)cc1n2CC1CC1]

In a 2 dram vial was added 7-amino-9-(cyclopropylmethyl)-3-(3,5-dimethyl-4-isoxazolyl)-9H-carbazole-1-carboxamide (0.030 g, 0.080 mmol), DMF (1 mL), Na$_2$CO$_3$ (0.085 g, 0.801 mmol) and (iodomethyl)cyclopentane (0.034 g, 0.160 mmol). The reaction was heated at 80° C. overnight. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-100% B over 25 minutes, then a 5-minute hold at 100% B; Flow: 20 mL/min. Fractions containing the desired product were combined and dried via centrifugal evaporation. The yield of the compound was 1.0 mg, and its estimated purity by LCMS analysis was 99%. Two analytical LC/MS injections were used to determine the final purity.

Injection 1 conditions: Retention Time: 1.802 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=457 [M+H$^+$].

Injection 2 conditions: Retention Time: 1.563 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS(ES) m/z=457 [M+H$^+$].

Example 40

7-(acetyl(methyl)amino)-9-(cyclopropylmethyl)-3-(3,5-dimethyl-4-isoxazolyl)-9H-carbazole-1-carboxamide

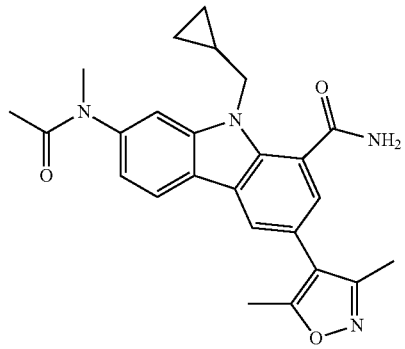 [SMILES: CC(=O)N(C)c1ccc2c3cc(-c4c(C)noc4C)cc(C(N)=O)c3n(CC3CC3)c2c1]

In a 2 dram vial was added 9-(cyclopropylmethyl)-3-(3,5-dimethyl-4-isoxazolyl)-7-(methylamino)-9H-carbazole-1-carboxamide (0.033 g, 0.085 mmol), DCM (1.0 mL), pyridine (0.336 g, 4.25 mmol) and acetyl chloride (0.033 g, 0.425 mmol). The reaction was stirred at room temperature for 0.5 hours. The reaction was quenched with water (0.1 ml), concentrated, diluted with DMSO and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 7-(acetyl(methyl)amino)-9-(cyclopropylmethyl)-3-(3,5-dimethyl-4-isoxazolyl)-9H-carbazole-1-carboxamide (9.5 mg, 25%). Two analytical LC/MS injections were used to determine the final purity.

Injection 1 conditions: HPLC Ret. Time=1.446, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=431 [M+H]$^+$.

Injection 2 conditions: HPLC Ret. Time=1.446, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=431 [M+H]+. 1H NMR (500 MHz, METHANOL-d4) d 8.20 (d, J=7.9 Hz, 1H), 8.12 (d, J=2.0 Hz, 1H), 7.60 (s, 1H), 7.50 (d, J=1.5 Hz, 1H), 7.44 (d, J=2.0 Hz, 1H), 7.14 (dd, J=8.2, 1.7 Hz, 1H), 4.53 (d, J=6.4 Hz, 2H), 4.32 (s, 1H), 3.38 (s, 3H), 2.47 (s, 3H), 2.32 (s, 3H), 1.93 (s, 3H), 1.31-1.22 (m, 1H), 0.51-0.44 (m, 2H), 0.38 (q, J=5.0 Hz, 2H).

Example 41

9-(cyclopropylmethyl)-3-(3,5-dimethyl-4-isoxazolyl)-7-(4-morpholinyl)-9H-carbazole-1-carboxamide

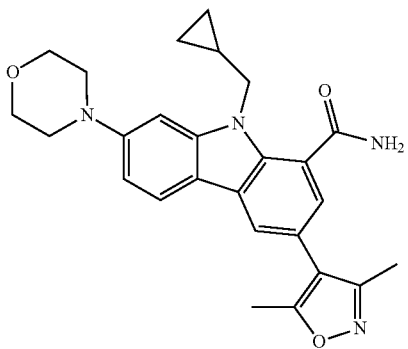 [SMILES: Cc1noc(C)c1-c1cc(C(N)=O)c2c(c1)c1ccc(N3CCOCC3)cc1n2CC1CC1]

In a 2 dram vial was added 7-amino-9-(cyclopropylmethyl)-3-(3,5-dimethyl-4-isoxazolyl)-9H-carbazole-1-carboxamide (0.012 g, 0.032 mmol), DMF (1.0 mL), Na2CO3 (0.014 g, 0.128 mmol) and 1-chloro-2-(2-chloroethoxy) ethane (4.58 mg, 0.032 mmol). The reaction was stirred at 110° C. for 72 hours. The reaction was concentrated, diluted with DMSO (2.0 ml) and was purified via preparative HPLC using the following conditions: Phenomenex Luna column 5 u, 100 A°, 21.2×100 mm, 30-90% Solvent B, (Solvent A (90% water, 10% methanol, 0.1% TFA), Solvent B (10% water, 90% methanol, 0.1% TFA), 10 min gradient, 15 minute run, 25 mL/min). Following concentration of the solvent via roto-evaporation, 9-(cyclopropylmethyl)-3-(3,5-dimethyl-4-isoxazolyl)-7-(4-morpholinyl)-9H-carbazole-1-carboxamide was collected as an off-white solid (1.2 mg, 8.2%). The final purity was determined by three LC/MS injection conditions: HPLC Ret. Time=0.8, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=444 [M+H]+. HPLC Ret. Time=11.599, column conditions: Xbridge 4.6 mm×50 mm, 3.5 μm particle size; flow rate 1 mL/min; gradient time 15 min; 100% Solvent A to 100% Solvent B and holding 100% Solvent B for 3 min; monitoring at 254 nm (Solvent A: 10% MeOH, 90% H2O, 0.1% TFA; Solvent B: 90% MeOH, 10% H2O, 0.1% TFA). HPLC Ret. Time=12.433, column conditions: Sunfire 4.6 mm×50 mm, 3.5 μm particle size; flow rate 1 mL/min; gradient time 15 min; 100% Solvent A to 100% Solvent B and holding 100% Solvent B for 3 min; monitoring at 220 nm (Solvent A: 10% MeOH, 90% H2O, 0.1% TFA; Solvent B: 90% MeOH, 10% H2O, 0.1% TFA). 1H NMR (400 MHz, METHANOL-d4) d 8.06 (d, J=1.8 Hz, 1H), 7.38 (d, J=1.8 Hz, 1H), 7.14 (d, J=1.5 Hz, 1H), 7.04 (dd, J=8.7, 1.9 Hz, 1H), 6.95 (d, J=2.2 Hz, 1H), 6.82 (d, J=2.2 Hz, 1H), 4.52 (d, J=6.6 Hz, 2H), 3.82-3.74 (m, 4H), 3.69 (dd, J=9.5, 4.8 Hz, 4H), 2.68 (s, 3H), 2.33 (s, 3H), 2.14-2.00 (m, 1H), 1.39-1.28 (m, 4H).

Example 42

9-(cyclopropylmethyl)-3-(3,5-dimethyl-4-isoxazolyl)-7-(2-oxo-1-piperidinyl)-9H-carbazole-1-carboxamide

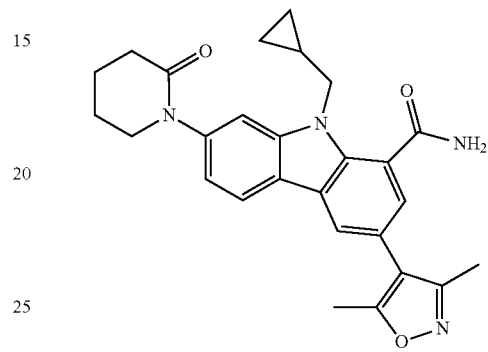

In a 2 dram vial was added 5-chloropentanoic acid (0.108 g, 0.791 mmol), DCM (1 mL), 1 drop of DMF and oxalyl dichloride (0.014 g, 0.107 mmol). The reaction was stirred at room temperature for 1 hour, then concentrated to dryness. To this was added DCM (1.0 mL), 7-amino-9-(cyclopropylmethyl)-3-(3,5-dimethyl-4-isoxazolyl)-9H-carbazole-1-carboxamide (0.020 g, 0.053 mmol) and pyridine (0.021 g, 0.267 mmol) The reaction was stirred at room temperature for 0.5 hours. The reaction was diluted with DCM (3.0 ml) and washed with water (2.0 ml). The layers were separated and the aqueous layer was back-extracted with DCM (3.0 ml). The combined organics were washed with brine (1.0 ml) and the layers separated. The organic was dried over Na2SO4, filtered and concentrated. The residue was transferred to a 2 dram vial and to this was added Acetone (1.0 mL), 18C6 (0.706 mg, 2.67 μmol) and potassium carbonate (2.95 mg, 0.021 mmol). The vial was capped and stirred at 50° C. for 3 hours. The reaction was cooled to room temperature, concentrated and diluted with DMSO and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-3-(3, 5-dimethyl-4-isoxazolyl)-7-(2-oxo-1-piperidinyl)-9H-carbazole-1-carboxamide (10.5 mg, 40%). Two analytical LC/MS injections were used to determine the final purity.

Injection 1 conditions: HPLC Ret. Time=1.505, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 50° C.;

Gradient: 0-100% B over 3 minutes, then a 0.75-minute hold at 100% B; Flow: 1.11 mL/min. MS (ES): m/z=457 [M+H]⁺.

Injection 2 conditions: HPLC Ret. Time=1.504, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=457 [M+H]⁺. ¹H NMR (500 MHz, METHANOL-$d_4$) d 8.16 (d, J=8.4 Hz, 1H), 8.09 (d, J=1.5 Hz, 1H), 7.64 (s, 1H), 7.46 (d, J=2.0 Hz, 1H), 7.45 (d, J=1.5 Hz, 1H), 7.17-7.13 (m, 1H), 4.50 (d, J=6.9 Hz, 2H), 4.38 (s, 2H), 3.81 (t, J=5.4 Hz, 2H), 2.61 (s, 2H), 2.47 (s, 3H), 2.32 (s, 3H), 2.10-2.00 (m, 2H), 1.34-1.22 (m, 1H), 0.49-0.37 (m, 4H).

Example 43

9-(cyclopropylmethyl)-3-(3,5-dimethyl-4-isoxazolyl)-7-(2-oxo-1,3-oxazinan-3-yl)-9H-carbazole-1-carboxamide

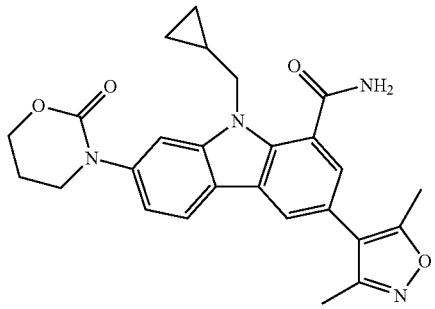 [SMILES: Cc1noc(C)c1-c1cc(C(N)=O)c2c(c1)c1ccc(N3CCCOC3=O)cc1n2CC1CC1]

The above titled compound was prepared from 3-chloropropyl carbonochloridate according to the conditions described for the preparation of 9-(cyclopropylmethyl)-3-(3,5-dimethyl-4-isoxazolyl)-7-(2-oxo-1-piperidinyl)-9H-carbazole-1-carboxamide. 9-(cyclopropylmethyl)-3-(3,5-dimethyl-4-isoxazolyl)-7-(2-oxo-1,3-oxazinan-3-yl)-9H-carbazole-1-carboxamide (8.9 mg, 40%) was obtained. HPLC Ret. Time=1.375 Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=459 [M+H]⁺.

Example 44

9-(cyclopropylmethyl)-3-(3,5-dimethyl-4-isoxazolyl)-7-(2-oxopyrrolidin-1-yl)-9H-carbazole-1-carboxamide

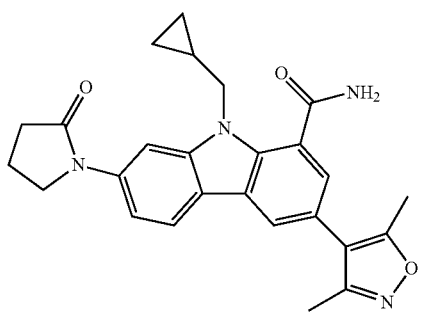 [SMILES: Cc1noc(C)c1-c1cc(C(N)=O)c2c(c1)c1ccc(N3CCCC3=O)cc1n2CC1CC1]

The above titled compound was prepared from 4-bromobutanoic acid according to the conditions described for the preparation of 9-(cyclopropylmethyl)-3-(3,5-dimethyl-4-isoxazolyl)-7-(2-oxo-1-piperidinyl)-9H-carbazole-1-carboxamide. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 5-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; gradient: 20-60% B over 25 minutes, then a 15-minute hold at 100% B; Flow: 20 mL/min. Fractions containing the desired product were combined and dried via centrifugal evaporation.

The yield of the product was 1.7 mg, and its estimated purity by LCMS analysis was 100%. Two analytical LC/MS injections were used to determine the final purity.

Injection 1 conditions: Retention Time: 1.456 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ES) m/z=445 [M+H⁺].

Injection 2 conditions: Retention Time: 1.453 min. Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS(ES) m/z=445 [M+H⁺].

Example 45

9-(cyclopropylmethyl)-3-(3,5-dimethyl-4-isoxazolyl)-7-(2-oxo-1,3-oxazolidin-3-yl)-9H-carbazole-1-carboxamide

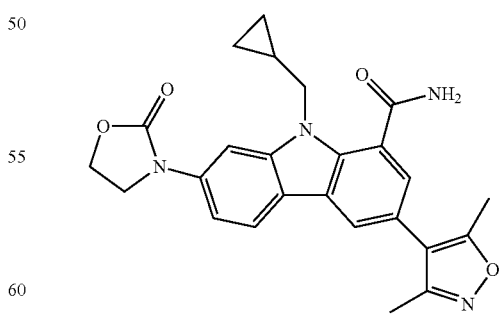

The above titled compound was prepared from 2-chloroethyl carbonochloridate according to the conditions described for the preparation of 9-(cyclopropylmethyl)-3-(3,5-dimethyl-4-isoxazolyl)-7-(2-oxo-1-piperidinyl)-9H-carbazole-1-carboxamide. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation.

The yield of the desired product was 7.6 mg, and its estimated purity by LCMS analysis was 99%. Two analytical LC/MS injections were used to determine the final purity.

Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Example 46

9-(cyclopropylmethyl)-3-(3,5-dimethyl-4-isoxazolyl)-7-(hydroxymethyl)-9H-carbazole-1-carboxamide

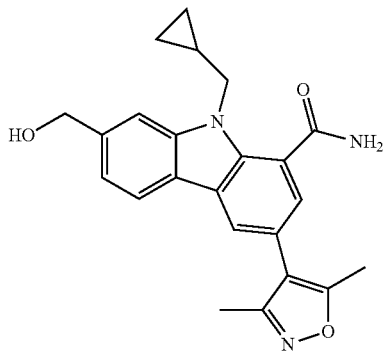 [SMILES: Cc1noc(C)c1-c1cc(C(N)=O)c2c(c1)c1ccc(CO)cc1n2CC1CC1]

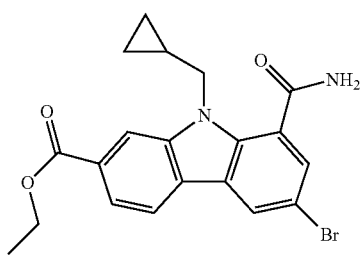 [SMILES: CCOC(=O)c1ccc2c3cc(Br)cc(C(N)=O)c3n(CC3CC3)c2c1]

Step 46a: Ethyl 6-bromo-8-carbamoyl-9-(cyclopropylmethyl)-9H-carbazole-2-carboxylate To a solution of ethyl 6-bromo-8-carbamoyl-9H-carbazole-2-carboxylate (2 g, 5.54 mmol) in acetone (20 mL) was added $K_2CO_3$ (1.531 g, 11.07 mmol), 18C6 (0.146 g, 0.554 mmol), and (bromomethyl)cyclopropane (3.74 g, 27.7 mmol). The reaction was heated to 70° C. overnight. The reaction was filtered through a celite pad and washed with acetone, then the filtrate was concentrated. The solid was triturated with $Et_2O$ to get ethyl 6-bromo-8-carbamoyl-9-(cyclopropylmethyl)-9H-carbazole-2-carboxylate (2 g, 4.82 mmol, 87% yield). HPLC Ret. Time=1.01, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 2 minute, then a 2-minute hold at 98% B; Flow: 0.8 mL/min. MS (ES): m/z=417 [M+H]$^+$.

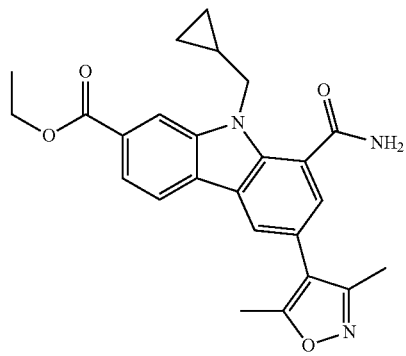 [SMILES: CCOC(=O)c1ccc2c3cc(-c4c(C)noc4C)cc(C(N)=O)c3n(CC3CC3)c2c1]

Step 46b: ethyl 8-carbamoyl-9-(cyclopropylmethyl)-6-(3,5-dimethylisoxazol-4-yl)-9H-carbazole-2-carboxylate To ethyl 6-bromo-8-carbamoyl-9-(cyclopropylmethyl)-9H-carbazole-2-carboxylate (0.600 g, 1.445 mmol), 3,5-dimethyl-4-(4,4,5,5-tetramethyl-1,3,2-dioxaborolan-2-yl)isoxazole (0.387 g, 1.734 mmol) was added THF (4.8 ml). The reaction was sealed with a Teflon lined cap and was degassed three times and back-filled with nitrogen gas. [1,1′-Bis(di-tert-butylphosphino)ferrocene]dichloropalladium(II) (0.047 g, 0.072 mmol) and 3.0M aqueous potassium phosphate solution (1.445 ml, 4.33 mmol) were added. The reaction was degassed three times and heated at 55° C. for 30 minutes. The reaction was concentrated, diluted with DCM (100 ml) and water (50 ml) and the added to a separatory funnel. The layers were separated and the organic was collected, dried over $Na_2SO_4$, filtered and concentrated to approximately 2.0 ml of volume. This was charged to a 24G ISCO column and purified using 0-75% ethyl acetate/heptane as the eluent. Following concentration, collected ethyl 8-carbamoyl-9-(cyclopropylmethyl)-6-(3,5-dimethylisoxazol-4-yl)-9H-carbazole-2-carboxylate (480 mg, 77%) as a whitish solid. HPLC Ret. Time=0.97, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=432 [M+H]$^+$.

Lithium aluminum hydride (1246 mg, 32.8 mmol) was added to a solution of ethyl 8-carbamoyl-9-(cyclopropylmethyl)-6-(3,5-dimethylisoxazol-4-yl)-9H-carbazole-2-carboxylate (624 mg, 10.95 mmol) in THF (10 mL) at 0° C. and stirred for 2 hours at room temperature. Additional lithium aluminum hydride (1246 mg, 32.8 mmol) was added and the reaction was stirred for 20 minutes. The reaction was carefully quenched with MeOH (3 ml) and the pH was adjusted to pH=2 with 1N HCl. The mixture was filtered through a Celite pad and washed with MeOH (20 ml). The filtrate was concentrated and the dark residue was partitioned between EtOAc (100 ml) and saturated aqueous NaHCO$_3$ (50 ml). The organic phase was washed with brine (10 ml), dried over Na$_2$SO$_4$ and concentrated. The residue was purified by silica gel chromatography (24G column), eluting with 0 to 10% MeOH in DCM to give 9-(cyclopropylmethyl)-3-(3,5-dimethyl-4-isoxazolyl)-7-(hydroxymethyl)-9H-carbazole-1-carboxamide (520 mg, 82%) as brown solid. The material was further purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-3-(3,5-dimethyl-4-isoxazolyl)-7-(hydroxymethyl)-9H-carbazole-1-carboxamide. Two analytical LC/MS injections were used to determine the final purity.

Injection 1 conditions: HPLC Ret. Time=1.353, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=390 [M+H]$^+$.

Injection 2 conditions: HPLC Ret. Time=1.365, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=390 [M+H]$^+$. $^1$H NMR (500 MHz, METHANOL-d$_4$) d 8.10-8.05 (m, 2H), 7.61 (s, 1H), 7.57 (s, 1H), 7.27 (d, J=7.9 Hz, 1H), 4.84 (s, 2H), 4.52 (d, J=6.4 Hz, 2H), 4.33 (s, 1H), 2.47 (s, 3H), 2.32 (s, 3H), 1.35-1.23 (m, 1H), 0.50-0.35 (m, 4H).

Example 47

9-(cyclopropylmethyl)-3-(3,5-dimethyl-4-isoxazolyl)-7-formyl-9H-carbazole-1-carboxamide

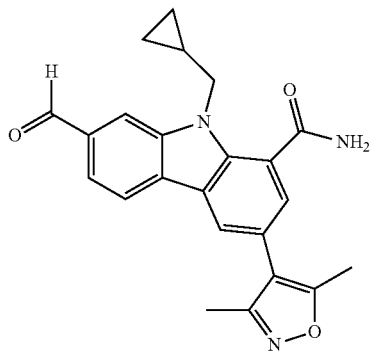 [SMILES: Cc1noc(C)c1-c1cc(C(N)=O)c2c(c1)c1ccc(C=O)cc1n2CC1CC1]

9-(cyclopropylmethyl)-3-(3,5-dimethyl-4-isoxazolyl)-7-(hydroxymethyl)-9H-carbazole-1-carboxamide (450 mg, 1.155 mmol) was dissolved in dichloromethane (3.0 mL) and THF (3 mL) was. Dess-Martin periodinane (6535 mg, 2.311 mmol) was added to the solution at room temperature. After 30 minutes at room temperature, the mixture was diluted with ethyl acetate (30 mL), washed with 1 M sodium sulfite solution (2×15 mL), brine (10 mL), dried (Na$_2$SO$_4$) and concentrated to give a tan solid. The crude material was purified by column chromatography (24G ISCO column) with solid loading. The compound was purified using 0-100% ethyl acetate/heptane as gradient/eluent. Following concentration, 9-(cyclopropylmethyl)-3-(3,5-dimethyl-4-isoxazolyl)-7-formyl-9H-carbazole-1-carboxamide (320 mg, 70%) was collected as an off-white solid. HPLC Ret. Time=0.90, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=388 [M+H]$^+$.

Example 48

9-(cyclopropylmethyl)-3-(3,5-dimethyl-4-isoxazolyl)-7-hydroxy-9H-carbazole-1-carboxamide

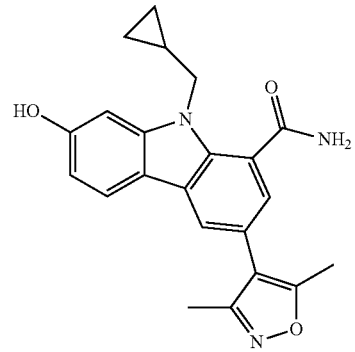 [SMILES: Cc1noc(C)c1-c1cc(C(N)=O)c2c(c1)c1ccc(O)cc1n2CC1CC1]

A 30% aqueous solution of hydrogen peroxide (0.016 mL, 0.155 mmol) and sulfuric acid (8.25 μl, 0.155 mmol), chilled in an ice bath, was added to a solution of 9-(cyclopropylmethyl)-3-(3,5-dimethyl-4-isoxazolyl)-7-formyl-9H-carbazole-1-carboxamide (12.00 mg, 0.031 mmol) in methanol (1.0 mL) at 0° C. After 1.5 hours, a chilled solution of 30% aqueous solution of hydrogen peroxide (0.100 mL) and sulfuric acid (0.050 mL) were added. The reaction was stirred at room temperature for 1 hour, then the mixture was stirred at room temperature for 6 hours. A 1.0N solution of NaOH (2.0 mL) was added. After stirring for 1 hour, the mixture was acidified to pH=4 with 1.0N HCl. DCM (3.0 ml) was added and the mixture was added to a separatory funnel. The layers were separated and the aqueous was back-extracted with DCM (3.0 ml). The organics were collected, dried over Na$_2$SO$_4$, filtered and concentrated. The residue was diluted with DMSO (1.0 ml) and was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient:

5-100% B over 15 minutes, then a 5-minute hold at 100% B; Flow: 20 mL/min. Fractions containing the desired product were combined and dried via centrifugal evaporation to give pure 9-(cyclopropylmethyl)-3-(3,5-dimethyl-4-isoxazolyl)-7-hydroxy-9H-carbazole-1-carboxamide (5.1 mg, 44%). Two analytical LC/MS injections were used to determine the final purity.

Injection 1 conditions: HPLC Ret. Time=1.279, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=376 [M+H]$^+$.

Injection 2 conditions: HPLC Ret. Time=1.280, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. (MS (ES): m/z=376 [M+H]$^+$. $^1$H NMR (500 MHz, METHANOL-d$_4$) δ 7.93 (d, J=1.5 Hz, 1H), 7.90 (d, J=8.4 Hz, 1H), 7.60 (s, 1H), 7.32 (d, J=1.5 Hz, 1H), 6.93 (d, J=2.0 Hz, 1H), 6.80 (dd, J=8.4, 2.0 Hz, 1H), 4.40 (d, J=6.4 Hz, 2H), 4.31 (s, 1H), 2.45 (s, 3H), 2.31 (s, 3H), 1.27 (br. s., 1H), 0.49-0.34 (m, 4H).

Example 49

9-(cyclopropylmethyl)-3-(3,5-dimethyl-4-isoxazolyl)-7-methoxy-9H-carbazole-1-carboxamide

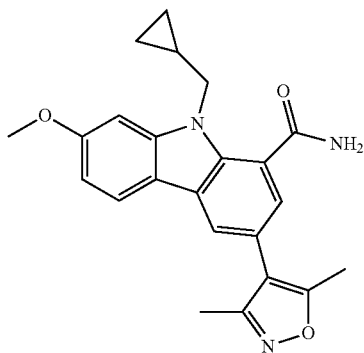

In a 2 dram vial was added 9-(cyclopropylmethyl)-3-(3,5-dimethyl-4-isoxazolyl)-7-hydroxy-9H-carbazole-1-carboxamide (0.025 g, 0.067 mmol), potassium carbonate (0.037 g, 0.266 mmol) acetone (1.0 mL), 18C6 (1.760 mg, 6.66 μmol) and iodomethane (0.095 g, 0.666 mmol). The reaction was capped and stirred at 75° C. for 16 hrs. The reaction was quenched with MeOH (0.1 ml) and concentrated. The residue was diluted with DMSO (1.0 ml) and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-3-(3,5-dimethyl-4-isoxazolyl)-7-methoxy-9H-carbazole-1-carboxamide (9.8 mg, 35%). Two analytical LC/MS injections were used to determine the final purity.

Injection 1 conditions: HPLC Ret. Time=1.503, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=390 [M+H]

Injection 2 conditions: HPLC Ret. Time=1.501, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=390 [M+H]

Example 50

8-carbamoyl-9-(cyclopropylmethyl)-6-(3,5-dimethyl-4-isoxazolyl)-9H-carbazol-2-yl morpholine-4-carboxylate

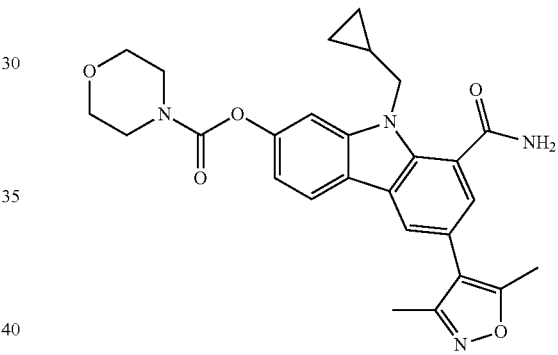

In a 2 dram vial was added 9-(cyclopropylmethyl)-3-(3,5-dimethyl-4-isoxazolyl)-7-hydroxy-9H-carbazole-1-carboxamide (0.025 g, 0.067 mmol), DCM (1.0 mL), pyridine (0.263 g, 3.33 mmol) and pyrrolidine-1-carbonyl chloride (0.044 g, 0.333 mmol). The reaction was stirred at room temperature for 0.5 hrs, then the reaction was heated to 80° C. for 30 minutes. The reaction was concentrated, diluted with DMSO (1.5 ml) and filtered through a 0.45 um nylon membrane syringe filter. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-6-(3,5-dimethyl-4-isoxazolyl)-9H-carbazol-2-ylmorpholine-4-carboxylate (8.8 mg, 25%). Two analytical LC/MS injections were used to determine the final purity.

Injection 1 conditions: HPLC Ret. Time=1.386, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:

water with 10 mM ammonium acetate; Temperature: 50° C.; Gradient: 0-100% B over 3 minutes, then a 0.75-minute hold at 100% B; Flow: 1.11 mL/min. MS (ES): m/z=489 [M+H]$^+$.

Injection 2 conditions: HPLC Ret. Time=1.384, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=489 [M+H]$^+$. $^1$H NMR (500 MHz, METHANOL-d$_4$) d 8.10 (d, J=8.4 Hz, 1H), 8.06 (d, J=2.0 Hz, 1H), 7.44 (d, J=2.0 Hz, 1H), 7.32 (d, J=2.0 Hz, 1H), 7.04 (dd, J=8.4, 2.0 Hz, 1H), 4.48 (d, J=6.4 Hz, 2H), 3.81 (br. s., 6H), 3.60 (br. s., 2H), 2.47 (s, 3H), 2.32 (s, 3H), 1.29 (s, 1H), 0.50-0.35 (m, 4H).

Example 51

9-(cyclopropylmethyl)-3-(3,5-dimethyl-4-isoxazolyl)-7-(4-morpholinyl methyl)-9H-carbazole-1-carboxamide

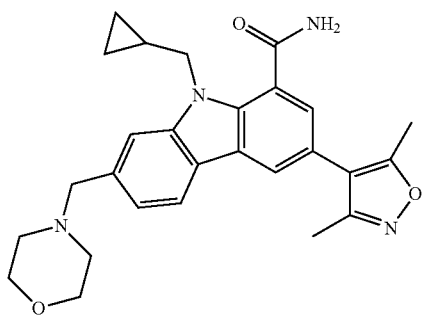 [SMILES: Cc1noc(C)c1-c1cc(C(N)=O)c2c(c1)c1ccc(CN3CCOCC3)cc1n2CC1CC1]

In a 2 dram vial was added 9-(cyclopropylmethyl)-3-(3,5-dimethyl-4-isoxazolyl)-7-formyl-9H-carbazole-1-carboxamide (0.015 g, 0.039 mmol), DMF (1.0 mL), TEA (8.09 μl, 0.058 mmol) and morpholine (3.37 mg, 0.039 mmol). The reaction was stirred at room temperature for 2 hours and sodium triacetoxyborohydride (8.21 mg, 0.039 mmol) and 1 drop of acetic acid were added. The reaction was stirred for 6 hours, then quenched with MeOH (0.1 ml) and concentrated. The residue was diluted with DMSO/MeOH and filtered through Celite and purified via preparative HPLC using the following conditions: Phenomenex Luna column 5 u, 100 A°, 21.2×100 mm, 30-90% Solvent B, (Solvent A (90% water, 10% methanol, 0.1% TFA), Solvent B (10% water, 90% methanol, 0.1% TFA), 10 min gradient, 15 minute run, 25 mL/min). Following concentration of the solvent via roto-evaporation, 9-(cyclopropylmethyl)-3-(3,5-dimethyl-4-isoxazolyl)-7-(4-morpholinylmethyl)-9H-carbazole-1-carboxamide was collected as a tan solid (1.1 mg, 4.7%). The final purity was determined by three LC/MS injection conditions: HPLC Ret. Time=0.65, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=459 [M+H]$^+$. HPLC Ret. Time=8.766, column conditions: Xbridge 4.6 mm×50 mm, 3.5 μm particle size; flow rate 1 mL/min; gradient time 15 min; 100% Solvent A to 100% Solvent B and holding 100% Solvent B for 3 min; monitoring at 254 nm (Solvent A: 10% MeOH, 90% H$_2$O, 0.1% TFA; Solvent B: 90% MeOH, 10% H$_2$O, 0.1% TFA). HPLC Ret. Time=8.883, column conditions: Sunfire 4.6 mm×50 mm, 3.5 μm particle size; flow rate 1 mL/min; gradient time 15 min; 100% Solvent A to 100% Solvent B and holding 100% Solvent B for 3 min; monitoring at 220 nm (Solvent A: 10% MeOH, 90% H$_2$O, 0.1% TFA; Solvent B: 90% MeOH, 10% H$_2$O, 0.1% TFA). $^1$H NMR (400 MHz, chloroform-d) d 8.19-8.13 (m, 1H), 8.11-8.07 (m, 1H), 7.82 (s, 1H), 7.79 (s, 1H), 7.55 (s, 1H), 7.51 (d, J=1.8 Hz, 2H), 4.57-4.50 (m, 2H), 4.44 (s, 2H), 4.01 (br. s., 4H), 2.86 (s, 2H), 2.68 (s, 2H), 2.48 (s, 3H), 2.36-2.32 (m, 3H), 1.34-1.20 (m, 1H), 0.54-0.38 (m, 4H).

Example 52

9-(cyclopropylmethyl)-3-(3,5-dimethyl-4-isoxazolyl)-7-(1-methyl-1-(4-morpholinyl)ethyl)-9H-carbazole-1-carboxamide

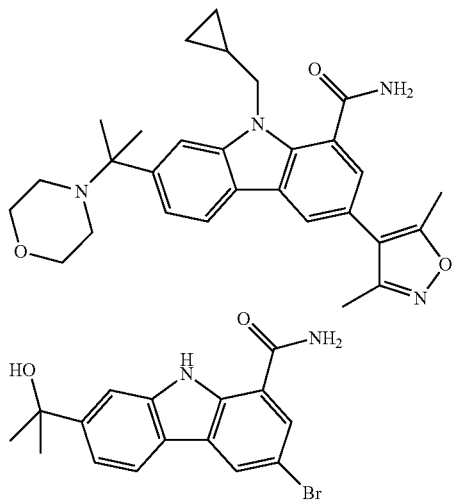

Step 52a: 3-bromo-7-(2-hydroxypropan-2-yl)-9H-carbazole-1-carboxamide

To a stirring solution of ethyl 6-bromo-8-carbamoyl-9H-carbazole-2-carboxylate (10.5 g, 24.71 mmol) in THF (1000 mL) at room temperature was added drop-wise methylmagnesium bromide (3.0 M solution in ether) (124 mL, 371 mmol), The reaction was stirred for 1 hour. The reaction was cooled to −78° C. in a dry ice/acetone bath and treated with acetone (50 mL, 681 mmol). The mixture was stirred for 5 minutes and warmed to 0° C., poured into a separatory funnel containing ethyl acetate and saturated. aqueous NH$_4$Cl solution. The organic layer was isolated and the aqueous layer was extracted with additional ethyl acetate. The organic extracts were combined and washed with water, saturated aqueous NaCl solution and dried (MgSO$_4$), filtered and concentrated in vacuo to give crude product as an oil. The crude material was purified on silica using 300 g Biotage cartridge eluting with 10% ethyl acetate/DCM to 70% ethyl acetate/DCM to give 3-bromo-7-(2-hydroxypropan-2-yl)-9H-carbazole-1-carboxamide, (3.7 g, 37%). MS (ES) 347/349 (M+1).

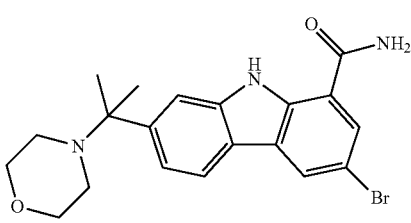 [SMILES: CC(C)(c1ccc2c(c1)[nH]c1c(C(N)=O)cc(Br)cc12)N1CCOCC1]

Step 52b: 3-bromo-7-(2-morpholinopropan-2-yl)-9H-carbazole-1-carboxamide 3-bromo-7-(2-hydroxypropan-2-yl)-9H-carbazole-1-carboxamide (195 mg, 0.533 mmol) was suspended in HCl (1.0M solution in diethyl ether) (2.0 ml, 2.00 mmol) and sonicated for 5 minutes to aid the dissolving of the starting material. The reaction was stirred at room temperature for 2 hours. Morpholine (3.0 ml, 34.4 mmol) was added to the reaction mixture under vigorous stirring and stirring was continued for 30 minutes at room temperature. The mixture was then poured into a separatory funnel and diluted with saturated aqueous $NaHCO_3$ solution and ethyl acetate. The layers were separated and the aqueous was back-extracted with ethyl acetate. The organics were collected, washed with brine, dried over $MgSO_4$, filtered and concentrated in vacuo. The crude material was purified by ISCO (12G column) using 0-100% ethyl acetate/heptane as the gradient/eluent. Following concentration, there was collected 3-bromo-7-(2-morpholinopropan-2-yl)-9H-carbazole-1-carboxamide (25 mg, 11%) as a tan/brown oil. HPLC Ret. Time=0.68, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=416 [M+H]$^+$.

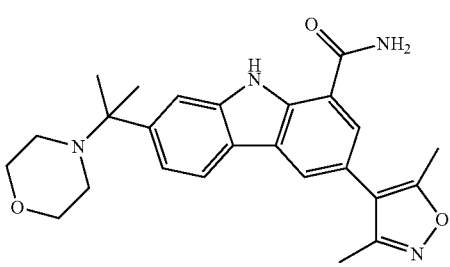 [SMILES: Cc1noc(C)c1-c1cc(C(N)=O)c2[nH]c3cc(C(C)(C)N4CCOCC4)ccc3c2c1]

Step 52c: 3-(3,5-dimethylisoxazol-4-yl)-7-(2-morpholinopropan-2-yl)-9H-carbazole-1-carboxamide To 3-bromo-7-(2-morpholinopropan-2-yl)-9H-carbazole-1-carboxamide (0.025 g, 0.060 mmol), (3,5-dimethylisoxazol-4-yl)boronic acid (10.16 mg, 0.072 mmol) was added THF (1.0 mL). The mixture was degassed three times and back-filled with nitrogen gas. [1,1'-Bis(di-tert-butylphosphino)ferrocene]dichloropalladium(II) (1.957 mg, 3.00 μmol) and 3.0M aqueous potassium phosphate solution (0.060 mL, 0.180 mmol) were added. The reaction mixture was degassed and additional three times and heated at 55° C. for 30 minutes. The reaction was concentrated, diluted with DCM (1.0 ml) and purified on a 4G ISCO column using 0-75% ethyl acetate/heptane as the gradient/eluent. Following concentration, collected 3-(3,5-dimethylisoxazol-4-yl)-7-(2-morpholinopropan-2-yl)-9H-carbazole-1-carboxamide as a whitish solid. HPLC Ret. Time=0.66, column conditions: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=433 [M+H]$^+$.

In a 2 dram vial, 3-(3,5-dimethylisoxazol-4-yl)-7-(2-morpholinopropan-2-yl)-9H-carbazole-1-carboxamide (25 mg, 0.060 mmol) was treated with (bromomethyl) cyclopropane (8.11 mg, 0.060 mmol) and potassium carbonate (8.30 mg, 0.060 mmol) in Acetone (1.0 mL). The reaction was heated to 50° C. overnight. The reaction mixture was filtered through a 0.45 um syringe filter, and concentrated. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min. Fractions containing the desired product were combined and dried via centrifugal evaporation to give 9-(cyclopropylmethyl)-3-(3,5-dimethyl-4-isoxazolyl)-7-(1-methyl-1-(4-morpholinyl)ethyl)-9H-carbazole-1-carboxamide (4.2 mg, 14%). Two analytical LC/MS injections were used to determine the final purity.

Injection 1 conditions: HPLC Ret. Time=1.808, column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS (ES): m/z=487 [M+H]$^+$.

Injection 2 conditions: HPLC Ret. Time=1.173, column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. MS (ES): m/z=487 [M+H]$^+$. $^1$H NMR (500 MHz, METHANOL-$d_4$) δ 8.07-8.04 (m, 1H), 8.04 (s, 1H), 7.74 (s, 2H), 7.51-7.47 (m, 1H), 7.42 (d, J=1.5 Hz, 2H), 4.52 (d, J=6.4 Hz, 2H), 3.75-3.70 (m, 4H), 2.60-2.54 (m, 4H), 2.46 (s, 3H), 2.31 (s, 3H), 1.50 (s, 6H), 1.31-1.23 (m, 1H), 0.49-0.36 (m, 4H).

Example 53

9-(cyclopropylmethyl)-3-(3,5-dimethyl-4-isoxazolyl)-7-(1-hydroxy-1-methylethyl)-9H-carbazole-1-carboxamide

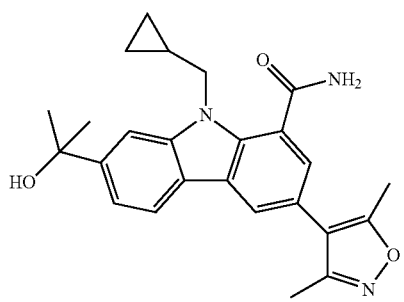 [SMILES: Cc1noc(C)c1-c1cc(C(N)=O)c2c(c1)c1ccc(C(C)(C)O)cc1n2CC1CC1]

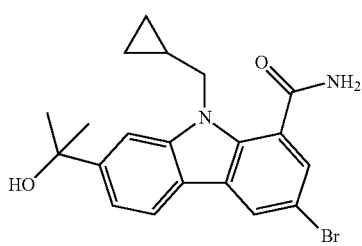 [SMILES: CC(C)(O)c1ccc2c3cc(Br)cc(C(N)=O)c3n(CC3CC3)c2c1]

Step 53a: 3-bromo-9-(cyclopropylmethyl)-7-(2-hydroxypropan-2-yl)-9H-carbazole-1-carboxamide A mixture of 3-bromo-7-(2-hydroxypropan-2-yl)-9H-carbazole-1-carboxamide (150 mg, 0.432 mmol), cyclopropylmethyl bromide (71.8 mL, 0.741 mmol) and $K_2CO_3$ (299 mg, 2.160 mmol) in acetone (2.0 mL) were heated at 75° C. for 20 hours. The mixture was filtered, rinsed with acetone and concentrated in vacuo. The crude product was dissolved in a small amount of DCM and charged to a silica gel 12 g ISCO column, which was eluted over a 10 min gradient with 0%-100% ethyl acetate/heptane to give 3-bromo-9-(cyclopropylmethyl)-7-(2-hydroxypropan-2-yl)-9H-carbazole-1-carboxamide (38) (100 mg, 58%). MS (ES) 401/403 (M+H$^+$).

To a vial was added 3-bromo-9-(cyclopropylmethyl)-7-(2-hydroxypropan-2-yl)-9H-carbazole-1-carboxamide (25 mg, 0.062 mmol), (3,5-dimethylisoxazol-4-yl)boronic acid (10.54 mg, 0.075 mmol) and PdCl$_2$(dppf)-CH$_2$Cl$_2$ adduct (2.54 mg, 3.11 µmol). The vial was fitted with a Teflon-lined septum cap, evacuated and back-filled with nitrogen gas. THF (1.0 mL) was added followed by 3.0M aqueous tripotassium phosphate (0.062 mL, 0.187 mmol) solution. The system was again evacuated and back-filled with nitrogen gas (sequence repeated two times). The vial was sealed and heated a 70° C. for 16 hours. The reaction was concentrated under a stream of nitrogen gas and re-suspended in DMF (2.0 mL), filtered through a plug of celite and purified on preparative HPLC using Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 20 mL/min. Fractions containing the desired product were combined and dried via centrifugal evaporation to give 9-(cyclopropylmethyl)-3-(3,5-dimethyl-4-isoxazolyl)-7-(1-hydroxy-1-methylethyl)-9H-carbazole-1-carboxamide (2 mg, 5%). MS (ES) 418 (M+H$^+$). $^1$H NMR (500 MHz, METHANOL-d$_4$/CDCl$_3$) δ 8.06 (dd, J=5.0, 3.0 Hz, 2H), 7.73 (d, J=1.0 Hz, 1H), 7.42 (d, J=2.0 Hz, 1H), 7.38 (dd, J=8.2, 1.2 Hz, 1H), 4.53 (d, J=6.4 Hz, 2H), 2.47 (s, 3H), 2.32 (s, 3H), 1.67 (s, 6H), 1.33-1.25 (m, 1H), 0.48-0.38 (m, 4H).

Example 54

3-(3,5-dimethyl-4-isoxazolyl)-7-(1-hydroxy-1-methylethyl)-9-(methysulfonyl)-9H-carbazole-1-carboxamide

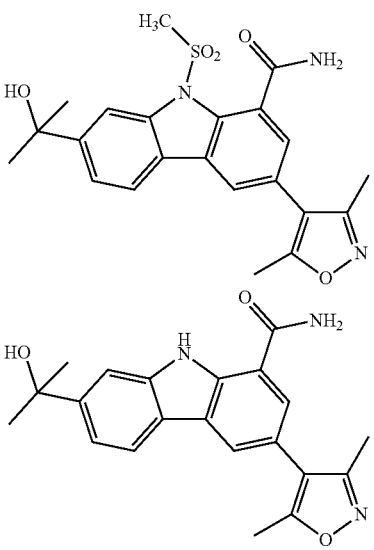

Step 54a: 3-(3,5-dimethylisoxazol-4-yl)-7-(2-hydroxypropan-2-yl)-9H-carbazole-1-carboxamide To a mixture of 3-bromo-7-(2-hydroxypropan-2-yl)-9H-carbazole-1-carboxamide (300 mg, 0.864 mmol), 3,5-dimethyl-4-(4,4,5,5-tetramethyl-1,3,2-dioxaborolan-2-yl)isoxazole (212 mg, 0.950 mmol), and PdCl$_2$(dppf)-CH$_2$Cl$_2$ adduct (35.3 mg, 0.043 mmol) in a screw cap vial was added THF (5 mL) followed by aq. solution of tripotassium phosphate (0.530 mL, 1.591 mmol). The vial was fitted with a Teflon lined septum cap. The system was evacuated under vacuum (via a needle from a nitrogen/vacuum manifold line) and backfilled with nitrogen gas. The procedure was repeated 2×. The nitrogen line was removed and the vial was heated for 3 h. The reaction was diluted with ethyl acetate (100 mL), poured into a separatory funnel and washed with water (2×25 mL) and sat. aq. NaCl solution (25 mL), dried (Na$_2$SO$_4$), filtered and concentrated in vacuo to give crude product. The crude product was dissolved in a small amount of DCM and charged to an ISCO silica gel 12 g ISCO column which was eluted over a 10 min gradient with 5%-100% dichloromethane/ethyl acetate to give 3-(3,5-dimethylisoxazol-4-yl)-7-(2-hydroxypropan-2-yl)-9H-carbazole-1-carboxamide (V) as a light yellow solid (270 mg, 86%). MS (ES), 364 (M+H$^+$).

To a solution of 3-(3,5-dimethylisoxazol-4-yl)-7-(2-hydroxypropan-2-yl)-9H-carbazole-1-carboxamide (50 mg, 0.138 mmol) in dry THF (2 mL), under a nitrogen atmosphere, was added potassium tert-butoxide (1 molar solution in THF) (0.275 mL, 0.275 mmol). The reaction was stirred for 10 min. at rt and then cooled in a ice bath and methanesulfonyl chloride (0.013 mL, 0.165 mmol) was added via syringe. The reaction was stirred for an additional 20 min, and quenched with ~100 µL of 1N aq. HCl solution. The reaction was diluted with ethyl acetate (10 mL) and water (10 mL), poured into a reparatory funnel, the layers partitioned and the EtOAc layer isolated. The aqueous layer was extracted with ethyl acetate (2×5 mL). The organic extracts were combined and washed sat aq. NaHCO$_2$ solution (1×5 mL), sat. aq. NaCl solution (1×5 mL), dried (Na$_2$SO$_4$) and filtered. The solvent was removed in vacuo to give crude product. The crude product was dissolved in a small amount of DCM and charged to an ISCO silica gel 4 g ISCO column which was eluted over a 10 min gradient with 5%-100% DCM/EtOAc to give 3-(3,5-dimethyl-4-isoxazolyl)-7-(1-hydroxy-1-methylethyl)-9-(methysulfonyl)-9H-carbazole-1-carboxamide as a solid (30 mg, 45%). MS (ES), (442, M+H$^+$). HPLC retention time, 1.34 min. Analytic column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

$^1$H NMR (400 MHz, CHLOROFORM-d) δ 8.17 (d, J=1.1 Hz, 1H), 7.96 (d, J=7.9 Hz, 1H), 7.93 (d, J=1.8 Hz, 1H), 7.57 (dd, J=8.1, 1.5 Hz, 1H), 7.50 (d, J=1.8 Hz, 1H), 3.63 (s, 3H), 2.46 (s, 3H), 2.32 (s, 3H), 1.72 (s, 6H).

Example 55

9-(cyclopropylsulfonyl)-3-(3,5-dimethyl-4-isoxazolyl)-7-(1-hydroxy-1-methylethyl)-9H-carbazole-1-carboxamide

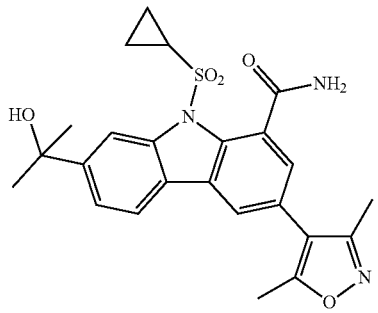 [SMILES: Cc1noc(C)c1-c1cc(C(N)=O)c2c(c1)c1ccc(C(C)(C)O)cc1n2S(=O)(=O)C1CC1]

The compound was prepared by reaction of 3-(3,5-dimethylisoxazol-4-yl)-7-(2-hydroxypropan-2-yl)-9H-carbazole-1-carboxamide but with cyclopropanesulfonyl chloride in the same manner as described for the preparation of Example 54 in 34% yield. MS (ES), 468 (M+H$^+$). HPLC retention time, 1.27 min. Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

$^1$H NMR (500 MHz, DMSO-d$_6$) δ 8.28 (d, J=1.8 Hz, 1H), 8.22-8.16 (m, 2H), 8.01 (s, 1H), 7.95 (s, 1H), 7.57 (s, 1H), 7.53 (d, J=7.9 Hz, 1H), 7.48 (d, J=1.8 Hz, 1H), 4.19 (q, J=4.9 Hz, 1H), 3.17 (d, J=4.9 Hz, 2H), 2.49 (s, 3H), 2.31 (s, 3H), 1.52 (s, 6H), 1.36 (d, J=4.3 Hz, 1H), 1.24-1.19 (m, 1H)

Example 56

9-(cyclopropylmethyl)-7-((cis-2,6-dimethyl-4-morpholinyl)carbonyl)-3-(3-methyl-4-isoxazolyl)-9H-carbazole-1-carboxamide

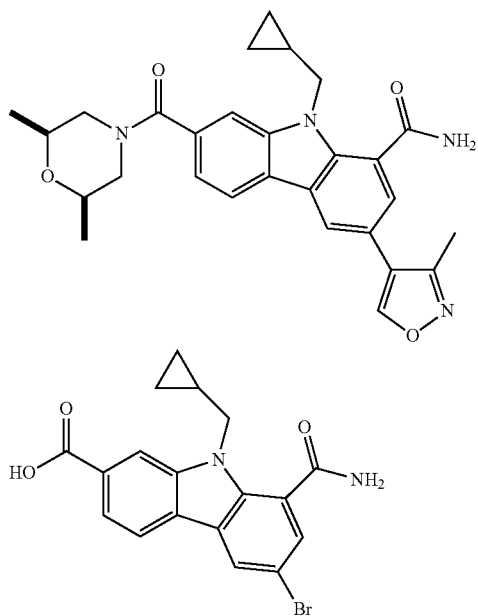

Step 56a: 6-bromo-8-carbamoyl-9-(cyclopropylmethyl)-9H-carbazole-2-carboxylic acid A solution of ethyl 6-bromo-8-carbamoyl-9-(cyclopropylmethyl)-9H-carbazole-2-carboxylate (2 g, 4.82 mmol) in THF (30 mL)/MeOH (10 mL) was treated with 3M aqueous NaOH (3.21 mL, 9.63 mmol). The reaction was heated at 55° C. for 2 h. The reaction was concentrated to ⅓ volume in vacuo. Water (25 mL) was added and acidified with aq. HCl to pH 2. The resulting solids were filtered, rinsed with water and dried to give 6-bromo-8-carbamoyl-9-(cyclopropylmethyl)-9H-carbazole-2-carboxylic acid (1.6 g, 86%). The crude product was used as is in the next reaction. MS(ES), 387 (M+H$^+$).

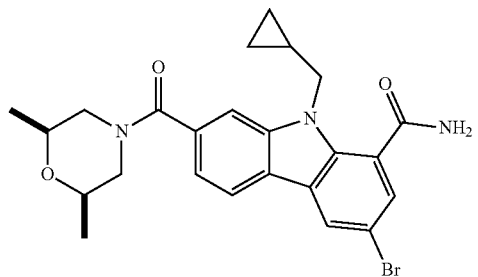 [SMILES: C[C@@H]1CN(C(=O)c2ccc3c4cc(Br)cc(C(N)=O)c4n(CC4CC4)c3c2)C[C@H](C)O1]

Step 56b: 3-bromo-9-(cyclopropylmethyl)-7-(cis-2,6-dimethylmorpholine-4-carbonyl)-9H-carbazole-1-carboxamide A solution of 6-bromo-8-carbamoyl-9-(cyclopropylmethyl)-9H-carbazole-2-carboxylic acid (1.4 g, 3.62 mmol)

and TBTU (1.277 g, 3.98 mmol) in DMF (15 mL) was treated with TEA (0.756 mL, 5.42 mmol) and cis-2,6-dimethylmorpholine (0.625 g, 5.42 mmol). The mixture was stirred for 2 h, diluted with ethyl acetate (150 mL), poured into a separatory funnel and washed with water (2×50 mL), 1N HCl aq. (50 mL) and sat. aq. NaCl solution (50 mL). The organic layer was dried ($Na_2SO_4$), filtered and concentrated in vacuo to give a solid. The crude product was dissolved in a small amount of DCM/MeOH and adsorbed to 10 g silica and purified on a 40 g ISCO column silica gel cartridge which was eluted with a 20 min gradient from 0%-5% MeOH/DCM to give 3-bromo-9-(cyclopropylmethyl)-7-(cis-2,6 dimethylmorpholine-4-carbonyl)-9H-carbazole-1-carboxamide (1.4 g, 80%). MS (ES) 485 ($M+H^+$).

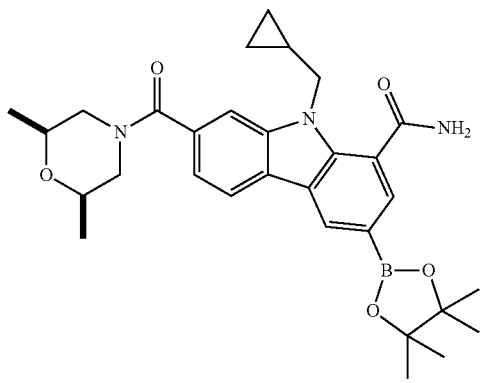

Step 56c: 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide To a mixture of 3-bromo-9-(cyclopropylmethyl)-7-(cis-2,6-dimethylmorpholine-4-carbonyl)-9H-carbazole-1-carboxamide (100 mg, 0.206 mmol), 4,4,4',4',5,5,5',5'-octamethyl-2,2'-bi(1,3,2-dioxaborolane) (62.9 mg, 0.248 mmol), potassium acetate (40.5 mg, 0.413 mmol) and $PdCl_2$(dppf)-$CH_2Cl_2$ adduct (8.43 mg, 10.32 µmol), in a screw cap vial, was added dioxane (2 mL). The vial was fitted with a Teflon lined septum cap and was then evacuated under vacuum (via a needle from a nitrogen/vacuum manifold line) and backfilled with nitrogen gas. The procedure was repeated three times. The needle was removed and the sealed vial was heated at 100° C. for 2 h. The reaction was diluted with DCM and filtered through a plug of celite and concentrated in vacuo. The crude product was dissolved in a small amount of DCM and charged to a 12 g ISCO silica gel column which was eluted over a 10 min gradient with 20%-100% DCM/EtOAc to give 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide, 80 mg, 72%). MS(ES) 532 ($M+H^+$).

To a mixture of 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide (25 mg, 0.047 mmol), $PdCl_2$(dppf)-$CH_2Cl_2$ adduct (1.921 mg, 2.352 µmol) 4-bromo-3-methylisoxazole (11.43 mg, 0.071 mmol) in a screw cap vial was added THF (0.5 mL) followed by 3M aqueous tripotassium phosphate (0.039 mL, 0.118 mmol). The vial was fitted with a Teflon lined septum cap. The system was evacuated under vacuum (via a needle from a nitrogen/vacuum manifold line) and backfilled with nitrogen gas. The procedure was repeated 2×. The nitrogen line was removed and the vial was heated at 75° C. for 4 h. The reaction was concentrated under a stream of nitrogen, resuspended in DMF (2 mL), filtered through a 0.45 micron nylon membrane and purified on preparative HPLC using a Waters XBridge C18, 19×150 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min to give 9-(cyclopropylmethyl)-7-((cis-2,6-dimethyl-4-morpholinyl)carbonyl)-3-(3-methyl-4-isoxazolyl)-9H-carbazole-1-carboxamide, 8.6 mg (38%). MS (ES) 487 ($M+H^+$). HPLC retention time 1.42 min.

Analytical column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min).

$^1$H NMR (500 MHz, METHANOL-$d_4$/$CD_3Cl$) δ 8.70 (s, 1H), 8.27 (d, J=2.0 Hz, 1H), 8.22 (d, J=7.9 Hz, 1H), 7.67 (d, J=1.5 Hz, 1H), 7.30 (d, J=7.9 Hz, 1H), 4.54 (d, J=6.4 Hz, 2H), 4.30 (br. s., 1H), 3.79-3.60 (m, 3H), 2.97-2.86 (m, 1H), 2.70-2.60 (m, 1H), 2.51 (s, 3H), 1.33-1.23 (m, 4H), 1.08 (br. s., 3H), 0.45 (d, J=8.4 Hz, 2H), 0.37 (d, J=4.0 Hz, 2H)

Example 57

9-(cyclopropylmethyl)-7-((cis-2,6-dimethyl-4-morpholinyl)carbonyl)-3-(5-methyl-4-isoxazolyl)-9H-carbazole-1-carboxamide

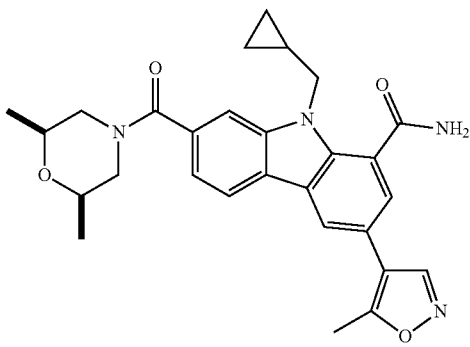 [SMILES: Cc1oncc1-c1cc(C(N)=O)c2c(c1)c1ccc(C(=O)N3C[C@@H](C)O[C@@H](C)C3)cc1n2CC1CC1]

The compound was prepared according to the method used to prepare Example 56. The reaction of 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide (25 mg, 0.047 mmol) with 4-iodo-5-methylisoxazole (14.75 mg, 0.071 mmol) gave 9-(cyclopropylmethyl)-7-((cis-2,6-dimethyl-4-morpholinyl)carbonyl)-3-(5-methyl-4-isoxazolyl)-9H-carbazole-1-carboxamide (14 mg, 62%). MS (ES) 487 ($M+H^+$). HPLC retention time, 1.44 min. Analytical column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min).

$^1$H NMR (rotamers) (500 MHz, methanol-$d_4$/CDCl$_3$) δ 8.58 (s, 1H), 8.28 (d, J=1.5 Hz, 1H), 8.23 (d, J=7.9 Hz, 1H), 7.68 (d, J=2.0 Hz, 1H), 7.31 (dd, J=7.9, 1.0 Hz, 1H), 4.60 (d, J=9.4 Hz, 1H), 4.55 (d, J=6.9 Hz, 2H), 4.30 (br. s., 1H), 3.67 (br. s., 2H), 2.98-2.90 (m, 1H), 2.69 (s, 3H), 2.66-2.61 (m, 1H), 1.35-1.24 (m, 4H), 1.10 (br. s., 3H), 0.46 (d, J=7.9 Hz, 2H), 0.38 (d, J=4.0 Hz, 2H).

Example 58

3-(3,5-dimethyl-4-isoxazolyl)-7-(4-morpholinylcarbonyl)-9H-carbazole-1-carbonitrile

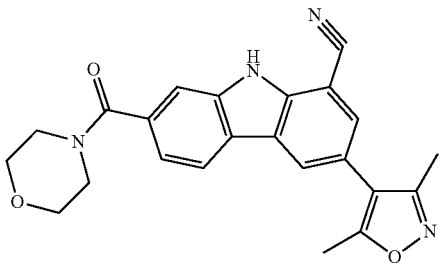 [SMILES: Cc1noc(C)c1-c1cc(C#N)c2[nH]c3cc(C(=O)N4CCOCC4)ccc3c2c1]

To 3-(3,5-dimethyl-4-isoxazolyl)-7-(morpholine-4-carbonyl)-9H-carbazole-1-carboxamide (65 mg, 0.155 mmol) was added DCM (1.0 mL) and Burgess reagent (130 mg, 0.544 mmol). The reaction was allowed to stir at room temperature. After 1 hour, the reaction was concentrated to dryness, and the crude product was divided into two equal parts. Half of the crude product was purified via preparative LC/MS using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation. The yield of 3-(3,5-dimethyl-4-isoxazolyl)-7-(4-morpholinylcarbonyl)-9H-carbazole-1-carbonitrile was 14.3 mg, and its estimated purity by LCMS analysis was 99%.

HPLC: RT=1.307 min; Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=401 [M+H$^+$].

Example 59

9-(cyclopropylmethyl)-3-(3,5-dimethyl-4-isoxazolyl)-7-(4-morpholinylcarbonyl)-9H-carbazole-1-carbonitrile

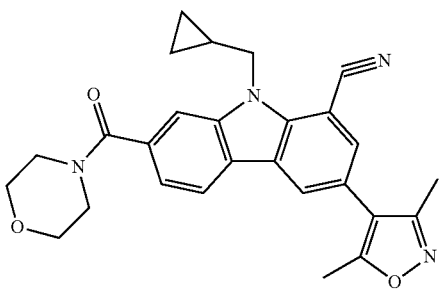 [SMILES: Cc1noc(C)c1-c1cc(C#N)c2c(c1)c1ccc(C(=O)N3CCOCC3)cc1n2CC1CC1]

To 3-(3,5-dimethyl-4-isoxazolyl)-7-(4-morpholinylcarbonyl)-9H-carbazole-1-carbonitrile (30 mg, 0.075 mmol) in acetone (1 mL) was added (bromomethyl) cyclopropane (101 mg, 0.749 mmol), and potassium carbonate (41.4 mg, 0.300 mmol). The reaction was then heated to 80° C. After 4 hours, the reaction was concentrated to dryness, diluted with DMF and filtered. The crude material was purified via preparative LCMS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 15-55% B over 25 minutes, then a 10-minute hold at 55% B; Flow: 20 mL/min. Fractions containing the desired product were combined and dried via centrifugal evaporation. The yield of 9-(cyclopropylmethyl)-3-(3,5-dimethyl-4-isoxazolyl)-7-(4-morpholinylcarbonyl)-9H-carbazole-1-carbonitrile was 7.7 mg, and its estimated purity by LCMS analysis was 99%.

HPLC: RT=1.537 min; Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=455 [M+H$^+$].

Example 60

9-acetyl-3-(3,5-dimethyl-4-isoxazolyl)-7-(cis-2,6-dimethylmorpholine-4-carbonyl)-9H-carbazole-1-carboxamide

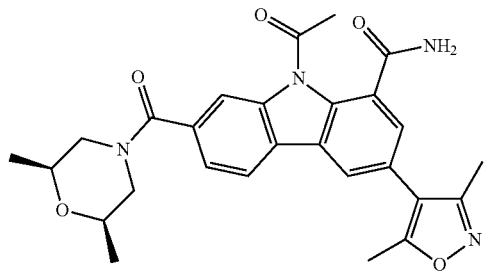

To a solution of 3-(3,5-dimethyl-4-isoxazolyl)-7-(cis-2,6-dimethylmorpholine-4-carbonyl)-9H-carbazole-1-carboxamide (32 mg, 0.072 mmol) in DMF (1.0 mL) was added sodium hydride (11.47 mg, 0.287 mmol). The reaction was allowed to stir at room temperature for 15 minutes, and then acetyl chloride (19.69 mg, 0.251 mmol) was added. The reaction was then stirred at room temperature for ½ hour. The reaction was quenched with water and diluted with DMF. The crude material was purified via preparative LCMS using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 15-55% B over 25 minutes, then a 10-minute hold at 55% B; Flow: 20 mL/min. Fractions containing the desired product were combined and dried via centrifugal evaporation. The yield of 9-(cyclopropylmethyl)-3-(3,5-dimethyl-4-isoxazolyl)-7-(4-morpholinylcarbonyl)-9H-carbazole-1-carbonitrile was 3.8 mg, and its estimated purity by LCMS analysis was 92%.

HPLC: RT=1.352 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=489 [M+H$^+$].

Example 61

3-(3,5-dimethyl-4-isoxazolyl)-7-(cis-2,6-dimethyl-morpholine-4-carbonyl)-N9-ethyl-9H-carbazole-1,9-dicarboxamide

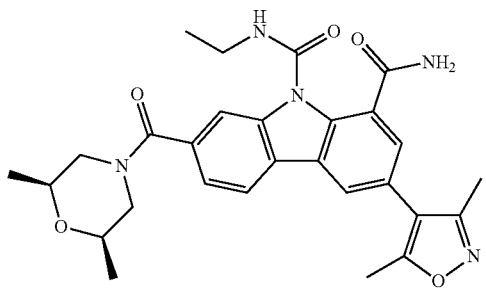

To 3-(3,5-dimethyl-4-isoxazolyl)-7-(cis-2,6-dimethyl-morpholine-4-carbonyl)-9H-carbazole-1-carboxamide (39 mg, 0.087 mmol) in DCM (1.0 mL) was added DMAP (0.534 mg, 4.37 μmol), pyridine (0.071 mL, 0.873 mmol) and isocyanatoethane (62.1 mg, 0.873 mmol). The reaction was allowed to stir at room temperature for 6 hours, and then heated to 80° C. overnight. An additional 300 ul of ethylisocyanate was added. After 24 hours, the reaction was concentrated to dryness, diluted with DMF and filtered.

The crude material was purified via preparative LC/MS using the following conditions: Column: Waters XBridge C18, 19×250 mm, 5-μm particles; Guard Column: Waters Xbridge C18, 19×10 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 15-55% B over 25 minutes, then a 10-minute hold at 55% B; Flow: 20 mL/min. Fractions containing the desired product were combined and dried via centrifugal evaporation. The yield of 3-(3,5-dimethyl-4-isoxazolyl)-7-(cis-2,6-dimethylmorpholine-4-carbonyl)-N9-ethyl-9H-carbazole-1,9-dicarboxamide was 2.8 mg, and its estimated purity by LCMS analysis was 98%.

HPLC: RT=1.448 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=518 [M+H$^+$].

Example 62

3-(3,5-dimethyl-4-isoxazolyl)-1-(5-methyl-1,3-oxazol-2-yl)-7-(4-morpholinylcarbonyl)-9H-carbazole

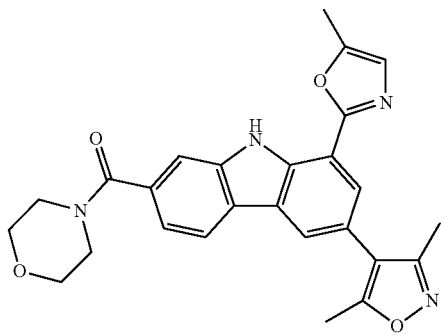 [SMILES: Cc1cnc(-c2cc(-c3c(C)noc3C)cc3c2[nH]c2cc(C(=O)N4CCOCC4)ccc23)o1]

To 3-(3,5-dimethyl-4-isoxazolyl)-7-(morpholine-4-carbonyl)-9H-carbazole-1-carboxamide (51 mg, 0.122 mmol) in DMF (1.0 mL) was added cesium carbonate (131 mg, 0.402 mmol) and 2,3-dibromoprop-1-ene (0.018 mL, 0.183 mmol). The reaction was then heated at 110° C. for 2 hours. The reaction was filtered and the crude material was purified via preparative LCMS using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 15-100% B over 25 minutes, then a 5-minute hold at 100% B; Flow: 20 mL/min. Fractions containing the desired product were combined and dried via centrifugal evaporation. The yield of 3-(3,5-dimethyl-4-isoxazolyl)-1-(5-methyl-1,3-oxazol-2-yl)-7-(4-morpholinylcarbonyl)-9H-carbazole was 1.9 mg, and its estimated purity by LCMS analysis was 100.

HPLC: RT=1.753 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=457 [M+H$^+$].

Example 63

3-(3,5-dimethyl-4-isoxazolyl)-7-(4-morpholinylcarbonothioyl)-9H-carbazole-1-carbothioamide

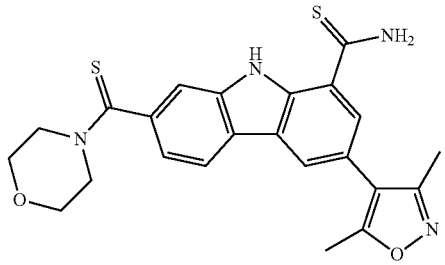

To 3-(3,5-dimethyl-4-isoxazolyl)-7-(morpholine-4-carbonyl)-9H-carbazole-1-carboxamide (53 mg, 0.127 mmol) in diglyme (1.0 mL) was added phosphorus pentasulfide (0.032 mL, 0.152 mmol) and sodium bicarbonate (74.5 mg, 0.887 mmol). The reaction was then heated to 100° C. After ¼ hour, the reaction was diluted with water and extracted with EtOAc. The combined organic extracts were dried and concentrated. Half of the crude material was purified via preparative LC/MS using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 15-100% B over 25 minutes, then a 5-minute hold at 100% B; Flow: 20 mL/min. Fractions containing the desired product were combined and dried via centrifugal evaporation. The yield of 3-(3,5-dimethyl-4-isoxazolyl)-7-(4-morpholinylcarbonothioyl)-9H-carbazole-1-carbothioamide was 3.0 mg, and its estimated purity by LCMS analysis was 98%.

HPLC: RT=1.388 min; Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=451 [M+H⁺].

Example 64

3-(3,5-dimethyl-4-isoxazolyl)-7-(4-morpholinylcarbonyl)-9H-carbazole-1-carbothioamide

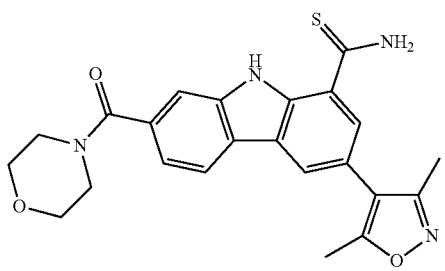 [SMILES: Cc1noc(C)c1-c1cc(C(N)=S)c2[nH]c3cc(C(=O)N4CCOCC4)ccc3c2c1]

To 3-(3,5-dimethyl-4-isoxazolyl)-7-(morpholine-4-carbonyl)-9H-carbazole-1-carboxamide (45 mg, 0.108 mmol) in diglyme (1.0 mL) was added phosphorus pentasulfide (6.86 µl, 0.032 mmol) and sodium bicarbonate (18.07 mg, 0.215 mmol). The reaction was then heated to 50° C. After 1 hour, the temperature was raised to 65° C. After another hour, the temperature was then raised to 80° C. After another hour, the temperature was raised again to 100° C. After 2 hours, an additional 10 mg of phosphorus pentasulfide was added and heating was continued. After an additional hour, the reaction was cooled to room temperature and concentrated. Half of the crude material was purified via preparative LCMS using the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 10-100% B over 25 minutes, then a 5 minute hold at 100% B; Flow: 20 mL/min. Fractions containing the desired product were combined and dried via centrifugal evaporation. The yield of 3-(3,5-dimethyl-4-isoxazolyl)-7-(4-morpholinylcarbonyl)-9H-carbazole-1-carbothioamide was 0.8 mg and its estimated purity by LCMS analysis was 98%.

HPLC: RT=1.44 min; Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=435 [M+H⁺].

Example 65

3-(3,5-dimethyl-4-isoxazolyl)-1-(4-methyl-1,3-thiazol-2-yl)-7-(4-morpholinylcarbonothioyl)-9H-carbazole

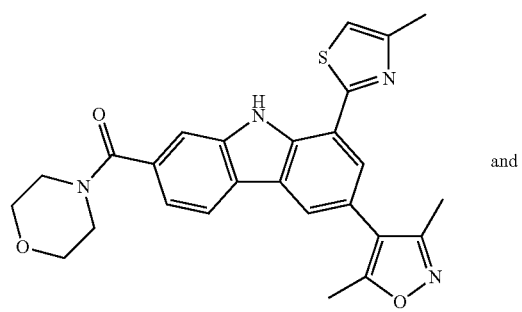 [SMILES: Cc1csc(-c2cc(-c3c(C)noc3C)cc3c2[nH]c2cc(C(=O)N4CCOCC4)ccc23)n1]

and

Example 66

3-(3,5-dimethyl-4-isoxazolyl)-1-(4-methyl-1,3-thiazol-2-yl)-7-(4-morpholinylcarbonyl)-9H-carbazole

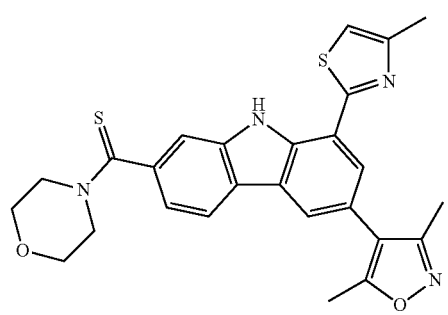 [SMILES: Cc1csc(-c2cc(-c3c(C)noc3C)cc3c2[nH]c2cc(C(=S)N4CCOCC4)ccc23)n1]

To a 1:2 mixture of 3-(3,5-dimethyl-4-isoxazolyl)-7-(4-morpholinylcarbonyl)-9H-carbazole-1-carbothioamide and 3-(3,5-dimethyl-4-isoxazolyl)-7-(4-morpholinylcarbonothioyl)-9H-carbazole-1-carbothioamide (32 mg, 0.071 mmol) in DMF (1 ml) (prepared in Example 63) was added 1-chloropropan-2-one (3.41 mg, 0.037 mmol). The reaction was then heated to 70° C. After 5 hours, an additional 50 µl of chloroacetone was added, and the reaction was heated for another 3 hours. After a total of 16 hours, the reaction was concentrated.

The crude material containing the two different products was purified via preparative LCMS using the following conditions: Column: Waters XBridge Shield RP18, 19×200 mm, 5-μm particles; Guard Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 25-100% B over 20 minutes, then a 5-minute hold at 100% B; Flow: 25 mL/min. Fractions containing the desired product were combined and dried via centrifugal evaporation. The yield of 3-(3,5-dimethyl-4-isoxazolyl)-1-(4-methyl-1,3-thiazol-2-yl)-7-(4-morpholinylcarbonothioyl)-9H-carbazole was 0.9 mg and its estimated purity by LCMS analysis was 92%.

HPLC: RT=1.920 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=473 [M+H⁺].

The yield of 3-(3,5-dimethyl-4-isoxazolyl)-1-(4-methyl-1,3-thiazol-2-yl)-7-(4-morpholinylcarbonyl)-9H-carbazole was 1.4 mg, and its estimated purity by LCMS analysis was 98%.

HPLC: RT=1.841 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=489 [M+H⁺].

Example 67

3-(3,5-dimethyl-4-isoxazolyl)-9-ethyl-7-(4-morpholinylcarbonyl)-9H-carbazole-1-carbothioamide

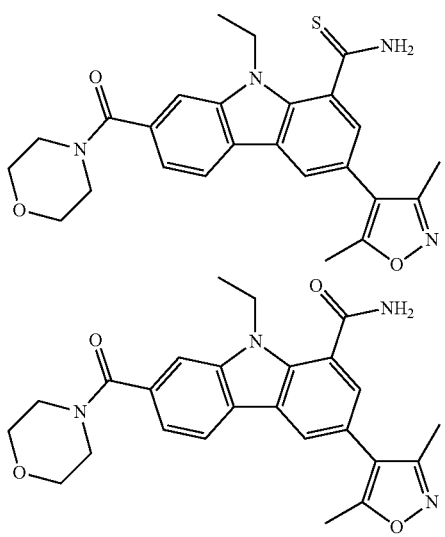

Step 67a: 3-(3,5-dimethylisoxazol-4-yl)-9-ethyl-7-(morpholine-4-carbonyl)-9H-carbazole-1-carboxamide To 3-(3,5-dimethylisoxazol-4-yl)-7-(morpholine-4-carbonyl)-9H-carbazole-1-carboxamide (41 mg, 0.098 mmol) in acetone (1 mL) was added iodoethane (153 mg, 0.980 mmol), and potassium carbonate (54.2 mg, 0.392 mmol). The reaction was heated to 70° C. for 24 h, then filtered and concentrated to give 40 mg (91%) of crude product, which was used without further purification.

HPLC RT: 0.74 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. LCMS: (ES) m/z 447.08 (M+H).

To 3-(3,5-dimethylisoxazol-4-yl)-9-ethyl-7-(morpholine-4-carbonyl)-9H-carbazole-1-carboxamide (20 mg, 0.045 mmol) in diglyme (1.0 mL) was added phosphorus pentasulfide (0.011 mL, 0.054 mmol) and sodium bicarbonate (26.3 mg, 0.314 mmol). The reaction was then heated to 100° C. After 7 hours, LCMS showed complete conversion to product. The mixture was diluted with DMF and purified via preparative LCMS using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10 mM ammonium acetate; Gradient: 10-100% B over 25 minutes, then a 5 minute hold at 100% B; Flow: 20 mL/min. Fractions containing the desired product were combined and dried via centrifugal evaporation. The yield of 3-(3,5-dimethyl-4-isoxazolyl)-9-ethyl-7-(4-morpholinylcarbonyl)-9H-carbazole-1-carbothioamide was 4.0 mg, and its estimated purity by LCMS analysis was 100%. HPLC: RT=1.841 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=489 [M+H⁺].

Example 68

9-(cyclopropylmethyl)-3-(3,5-dimethyl-4-isoxazolyl)-7-(4-morpholinylcarbonyl)-9H-carbazole-1-carbothioamide

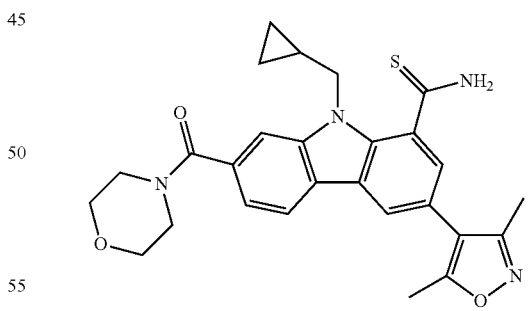

To 9-(cyclopropylmethyl)-3-(3,5-dimethyl-4-isoxazolyl)-7-(morpholine-4-carbonyl)-9H-carbazole-1-carboxamide (50 mg, 0.106 mmol) in diglyme (1.0 mL) was added phosphorus pentasulfide (6.75 μl, 0.032 mmol) and sodium bicarbonate (17.78 mg, 0.212 mmol). The reaction was then heated to 65° C. After 2 hours, the mixture was diluted with DMF the crude material was purified via preparative LCMS using the following conditions: Column: Waters XBridge C18, 19×250 mm, 5-μm particles; Guard Column: Waters XBridge C18, 19×10 mm, 5-μm particles; Mobile Phase A:

5:95 acetonitrile:water with 10 mM ammonium acetate; Mobile Phase B: 95:5 acetonitrile:water with 10 mM ammonium acetate; Gradient: 15-100% B over 25 minutes, then a 5 minute hold at 100% B; Flow: 20 mL/min. Fractions containing the desired product were combined and dried via centrifugal evaporation. The yield of 9-(cyclopropylmethyl)-3-(3,5-dimethyl-4-isoxazolyl)-7-(4-morpholinylcarbonyl)-9H-carbazole-1-carbothioamide was 9.3 mg, and its estimated purity by LCMS analysis was 98%.

HPLC: RT=1.382 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=489 [M+H$^+$].

Example 69

3-(3,5-dimethyl-4-isoxazolyl)-7-(4-morpholinylcarbonyl)-1-(1H-1,2,4-triazol-3-yl)-9H-carbazole

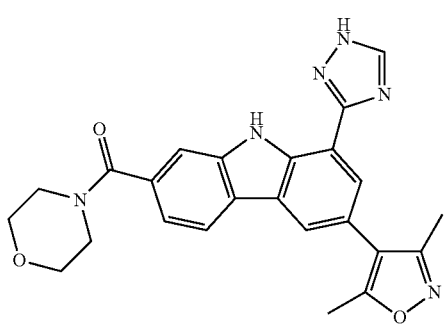 [SMILES: Cc1noc(C)c1-c1cc(-c2nc[nH]n2)c2[nH]c3cc(C(=O)N4CCOCC4)ccc3c2c1]

To 3-(3,5-dimethyl-4-isoxazolyl)-7-(morpholine-4-carbonyl)-9H-carbazole-1-carboxamide (60 mg, 0.143 mmol) was added dimethylformamide dimethylacetal (1.0 mL). The reaction was then heated to 110° C. for ½ hour. Next, the mixture was concentrated to dryness. The residue was then dissolved in AcOH (0.5 ml), then hydrazine hydrate (7.73 μl, 0.158 mmol) and more AcOH (0.5 ml) were added. Next, the reaction was allowed to stir at 90° C. for 1 hour. The reaction was cooled to room temperature, concentrated, diluted with DMF and the crude material was purified via preparative LCMS using the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10 mM ammonium acetate; Gradient: 5-40% B over 25 minutes, then a 15 minute hold at 40% B; Flow: 20 mL/min. Fractions containing the desired product were combined and dried via centrifugal evaporation. The yield of 3-(3,5-dimethyl-4-isoxazolyl)-7-(4-morpholinylcarbonyl)-1-(1H-1,2,4-triazol-3-yl)-9H-carbazole was 10.9 mg, and its estimated purity by LCMS analysis was 99%. HPLC: RT=1.200 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=443 [M+H$^+$].

Example 70

9-(cyclopropylmethyl)-3-(3,5-dimethyl-4-isoxazolyl)-7-(4-morpholinylcarbonyl)-1-(1H-1,2,4-triazol-3-yl)-9H-carbazole

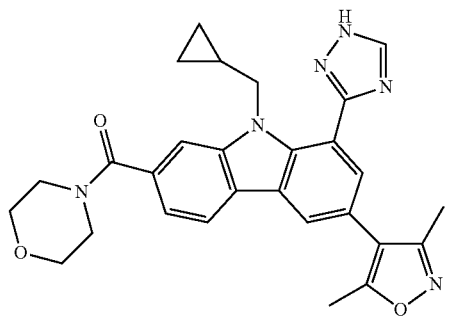 [SMILES: Cc1noc(C)c1-c1cc(-c2nc[nH]n2)c2c(c1)c1ccc(C(=O)N3CCOCC3)cc1n2CC1CC1]

To 9-(cyclopropylmethyl)-3-(3,5-dimethyl-4-isoxazolyl)-7-(morpholine-4-carbonyl)-9H-carbazole-1-carboxamide (40 mg, 0.085 mmol) was added dimethylformamide dimethylacetal (1.0 mL). The reaction was then heated to 110° C. for ½ hour. Next, the mixture was concentrated to dryness. The residue was then dissolved in AcOH (0.5 ml) and hydrazine hydrate (4.57 μl, 0.093 mmol) in AcOH (0.5 ml) was added. Next, the reaction was stirred at 90° C. for 1 hour. The reaction was cooled to room temperature, concentrated, diluted with DMF and submitted for purification.

The crude material was purified via preparative LCMS using the following conditions: Column: Waters XBridge Shield RP18, 19×200 mm, 5-μm particles; Guard Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 5-45% B over 25 minutes, then a 5 minute hold at 45% B; Flow: 25 mL/min. Fractions containing the desired product were combined and dried via centrifugal evaporation. The yield of 9-(cyclopropylmethyl)-3-(3,5-dimethyl-4-isoxazolyl)-7-(4-morpholinylcarbonyl)-1-(1H-1,2,4-triazol-3-yl)-9H-carbazole was 7.1 mg, and its estimated purity by LCMS analysis was 95%.

HPLC: RT=1.236 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI) m/z=497 [M+H$^+$].

Example 71

9-(cyclopropylmethyl)-3-(3,5-dimethyl-4-isoxazolyl)-7-(1,1-dioxido-2-isothiazolidinyl)-9H-carbazole-1-carboxamide

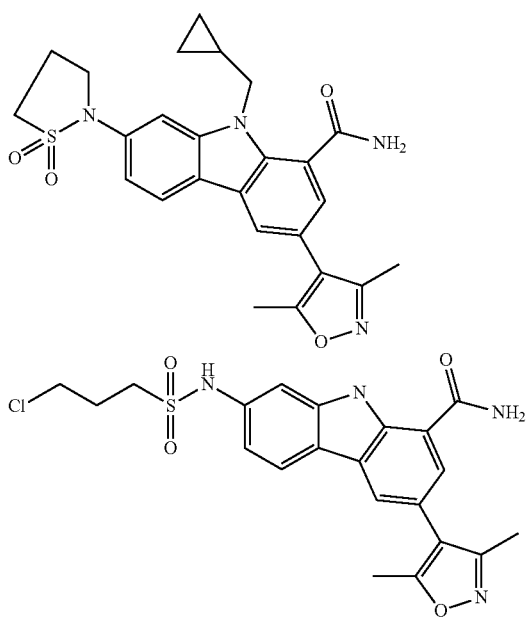

Step 71a: 7-(3-chloropropylsulfonamido)-3-(3,5-dimethylisoxazol-4-yl)-9H-carbazole-1-carboxamide To a solution of 7-amino-3-(3,5-dimethylisoxazol-4-yl)-9H-carbazole-1-carboxamide (50 mg, 0.156 mmol) in DCM (1 mL) was added TEA (0.044 mL, 0.312 mmol) followed by the addition of 3-chloropropane-1-sulfonyl chloride (0.028 mL, 0.234 mmol). The reaction was stirred for 30 minutes and concentrated in vacuo to give crude 7-(3-chloropropylsulfonamido)-3-(3,5-dimethylisoxazol-4-yl)-9H-carbazole-1-carboxamide, MS (ESI) 485 (M+H$^+$).

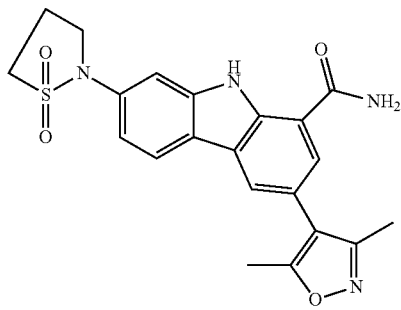

Step 71b: 3-(3,5-dimethylisoxazol-4-yl)-7-(1,1-dioxidoisothiazolidin-2-yl)-9H-carbazole-1-carboxamide The crude 7-(3-chloropropylsulfonamido)-3-(3,5-dimethylisoxazol-4-yl)-9H-carbazole-1-carboxamide was dissolved in DMF (0.5 mL) and cesium carbonate (102 mg, 0.312 mmol) was added. The mixture was heated at 75° C. for 2 hours, cooled to room temperature, diluted with ethyl acetate (15 mL) and poured into a separatory funnel. The ethyl acetate layer was washed with aq. 10% LiCl solution (2×5 mL), sat. aq. NaCl solution (1×5 mL), dried (Na$_2$SO$_4$), filtered and concentrated in vacuo to give crude 3-(3,5-dimethylisoxazol-4-yl)-7-(1,1-dioxidoisothiazolidin-2-yl)-9H-carbazole-1-carboxamide (40 mg, crude). MS (ESI) 425 (M+H$^+$). HPLC retention time, 1.49 min. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

To a solution of crude 3-(3,5-dimethylisoxazol-4-yl)-7-(1,1-dioxidoisothiazolidin-2-yl)-9H-carbazole-1-carboxamide (25 mg, 0.059 mmol) in acetone (1 mL) was added K$_2$CO$_3$ (40.7 mg, 0.294 mmol), 18-crown-6 (5 mg), and (bromomethyl)cyclopropane (0.029 mL, 0.294 mmol). The vial was sealed and heated at 75° C. for 4 hours. The acetone was evaporated under a stream of nitrogen gas. Next, the residue was re-suspended in DMF (2 mL) and filtered through a 0.45 micron nylon membrane syringe filter. The crude material was purified by preparative HPLC using a Waters XBridge C18, 19×250 mm, 5-μm particle column; Mobile Phase A: 5:95 acetonitrile:water with 10 mM ammonium acetate; Mobile Phase B: 95:5 acetonitrile:water with 10 mM ammonium acetate; Gradient: 0-100% B over 25 minutes, then a 5-minute hold at 100% B; Flow: 20 mL/min to give 9-(cyclopropylmethyl)-3-(3,5-dimethyl-4-isoxazolyl)-7-(1,1-dioxido-2-isothiazolidinyl)-9H-carbazole-1-carboxamide (5.6 mg, 0.012 mmol, 19.87% yield). MS(ESI) 479 (M+H$^+$).

$^1$H NMR (500 MHz, DMSO-d$_6$) δ 8.28-8.23 (m, 3H), 7.82 (s, 1H), 7.40 (s, 1H), 7.36 (d, J=1.3 Hz, 1H), 7.21 (d, J=8.8 Hz, 1H), 4.47 (d, J=7.1 Hz, 2H), 3.91 (t, J=6.4 Hz, 2H), 3.58 (t, J=7.4 Hz, 2H), 2.50-2.44 (m, 5H), 2.32 (s, 3H), 1.25 (br. s., 1H), 0.43-0.37 (m, 4H).

Example 72

3-(3,5-dimethylisoxazol-4-yl)-6-methoxy-9-(methylsulfonyl)-9H-carbazole-1-carboxamide

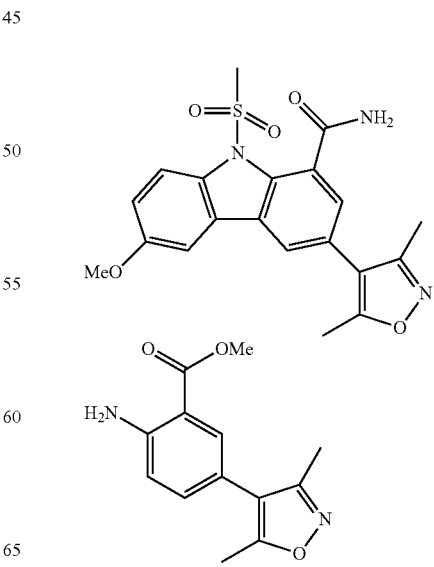

Step 72a: Methyl 2-amino-5-(3,5-dimethylisoxazol-4-yl)benzoate

Methyl 2-amino-5-bromobenzoate (1.065 g, 4.63 mmol) was dissolved in THF (23.15 ml) in a pressure vial. (3,5-dimethylisoxazol-4-yl)boronic acid (0.718 g, 5.09 mmol) and tripotassium phosphate (3M in H$_2$O) (4.63 ml, 13.89 mmol) were added, then the solution was degassed with bubbling nitrogen. PdCl$_2$(dppf) (0.169 g, 0.232 mmol) was added, then the pressure vial was sealed and heated to 70° C. After 3 hours, the reaction was cooled, diluted with water, and extracted twice with EtOAc. The organic layers were dried with sodium sulfate and concentrated. The residue was purified via ISCO (40 g column; Hex/EtOAc; 0 to 60% gradient) to give methyl 2-amino-5-(3,5-dimethylisoxazol-4-yl)benzoate (0.742 g, 3.01 mmol, 65.1% yield).

HPLC RT=0.84 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=247 [M+H]$^+$.

$^1$H NMR (400 MHz, CHLOROFORM-d) δ 7.75 (d, J=2.2 Hz, 1H), 7.16 (dd, J=8.5, 2.1 Hz, 1H), 6.74 (d, J=8.6 Hz, 1H), 5.82 (br. s., 2H), 3.90 (s, 3H), 2.38 (s, 3H), 2.25 (s, 3H)

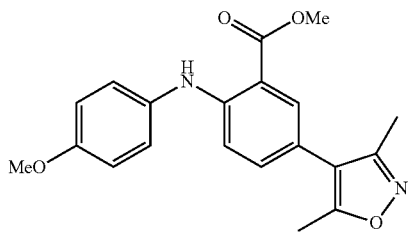 [SMILES: COC(=O)c1cc(-c2c(C)noc2C)ccc1Nc1ccc(OC)cc1]

Step 72b: methyl 5-(3,5-dimethylisoxazol-4-yl)-2-((4-methoxyphenyl)amino)benzoate A solution of 1-bromo-4-methoxybenzene (1.812 g, 9.68 mmol), methyl 2-amino-5-(3,5-dimethylisoxazol-4-yl)benzoate (1.704 g, 6.92 mmol) and Cs$_2$CO$_3$ (4.508 g, 13.84 mmol) (Cesium carbonate was suspended) in toluene (46 mL) was degassed with bubbling nitrogen. Chloro(2-dicyclohexylphosphino-2',4',6'-triisopropyl-1,1'-biphenyl)[2-(2'-amino-1,1'-biphenyl)]palladium(II) (0.136 g, 0.173 mmol) was added, then the reaction was heated to 100° C. overnight. The reaction was cooled to room temperature, then diluted with water and EtOAc. The organic layer was washed with brine, dried with sodium sulfate, and concentrated. The residue was purified via ISCO (80 g column; Hex/EtOAc; 0 to 60% gradient). 1.935 g of the product was obtained, 79%. HPLC RT=1.10 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=353 [M+H]$^+$.

$^1$H NMR (400 MHz, CHLOROFORM-d) δ 9.34 (s, 1H), 7.84 (d, J=2.0 Hz, 1H), 7.24-7.17 (m, 2H), 7.14 (dd, J=8.7, 2.1 Hz, 1H), 7.03 (d, J=8.8 Hz, 1H), 6.96-6.88 (m, 2H), 3.93 (s, 3H), 3.84 (s, 3H), 2.39 (s, 3H), 2.26 (s, 3H)

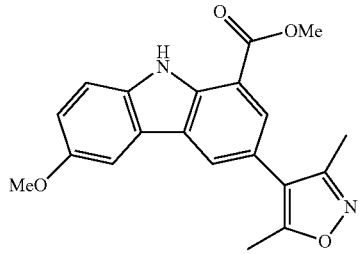 [SMILES: COC(=O)c1cc(-c2c(C)noc2C)cc2c1[nH]c1ccc(OC)cc12]

Step 72c: Methyl 3-(3,5-dimethylisoxazol-4-yl)-6-methoxy-9H-carbazole-1-carboxylate Methyl 5-(3,5-dimethylisoxazol-4-yl)-2-((4-methoxyphenyl)amino)benzoate (1.936 g, 5.50 mmol), palladium(II) acetate (0.124 g, 0.550 mmol), and potassium carbonate (0.076 g, 0.550 mmol) were dissolved in pivalic acid (16 mL). The reaction was heated to 110° C. in a vial open to air overnight. The reaction was cooled and quenched into stirring saturated aqueous. NaHCO$_3$. The solution was extracted twice with EtOAc. The organic layers were dried with sodium sulfate and concentrated. The residue was purified via ISCO (80 g column; Hex/EtOAc; 0 to 60% gradient). 1.054 g product, 55%.

HPLC RT=1.02 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=351 [M+H]$^+$.

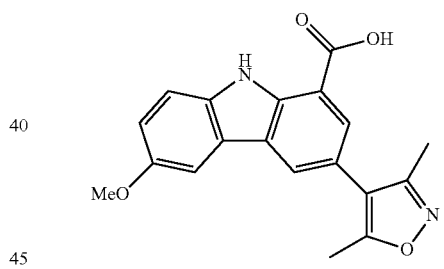

Step 72d: 3-(3,5-dimethylisoxazol-4-yl)-6-methoxy-9H-carbazole-1-carboxylic acid To a solution of methyl 3-(3,5-dimethylisoxazol-4-yl)-6-methoxy-9H-carbazole-1-carboxylate (0.050 g, 0.143 mmol) in THF (0.571 ml) and water (0.143 ml) was added lithium hydroxide hydrate (0.030 g, 0.714 mmol). After 1 h, 0.070 mL H$_2$O and 0.280 mL THF were added. The reaction was stirred at room temperature for two days. The reaction was quenched with 1 M HCl and extracted twice with EtOAc. The organic layers were concentrated to give 3-(3, 5-dimethylisoxazol-4-yl)-6-methoxy-9H-carbazole-1-carboxylic acid (0.051 g, 0.152 mmol, 106% yield), which was used with further purification.

HPLC RT=0.89 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=337 [M+H]$^+$.

111

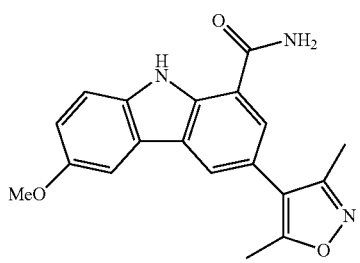 [SMILES: COc1ccc2[nH]c3c(C(N)=O)cc(-c4c(C)noc4C)cc3c2c1]

Step 72e: 3-(3,5-dimethylisoxazol-4-yl)-6-methoxy-9H-carbazole-1-carboxamide 3-(3,5-dimethylisoxazol-4-yl)-6-methoxy-9H-carbazole-1-carboxylic acid (0.051 g, 0.152 mmol) was dissolved in THF (1.25 mL) and DCM (0.250 mL). EDC (0.058 g, 0.303 mmol), HOBt (0.046 g, 0.303 mmol), and ammonium hydroxide (0.035 mL, 0.910 mmol) were added. The reaction was stirred overnight at room temperature, then concentrated. The residue was sonicated with water. The solid was filtered off, washed with water, and dried to give 3-(3,5-dimethylisoxazol-4-yl)-6-methoxy-9H-carbazole-1-carboxamide (0.040 g, 0.119 mmol, 79% yield). HPLC RT=0.86 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=336 [M+H]$^+$.

To a solution of 3-(3,5-dimethylisoxazol-4-yl)-6-methoxy-9H-carbazole-1-carboxamide (0.020 g, 0.060 mmol) in THF (0.596 ml) was added potassium tert-butoxide (1.0 M in THF) (0.078 ml, 0.078 mmol). After 5 minutes, methanesulfonyl chloride (0.014 ml, 0.179 mmol) was added. After 30 minutes, the reaction was quenched with MeOH and evaporated.

The material was purified by prep HPLC. (Column: YMC ODS C18 5 u 30×100 mm. Solvent A: 10% MeOH, 90% H2O, 0.1% TFA. Solvent B: 90% MeOH, 10% H2O, 0.1% TFA. Gradient 0 to 100% B over 30 minutes, 7 minute hold time) to give 3-(3,5-dimethylisoxazol-4-yl)-6-methoxy-9-(methylsulfonyl)-9H-carbazole-1-carboxamide (0.011 g, 0.026 mmol, 43.0% yield).

HPLC RT=0.81 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=414 [M+H]$^+$.

$^1$H NMR (400 MHz, METHANOL-d$_4$) δ 8.18 (d, J=2.0 Hz, 1H), 7.90 (d, J=9.0 Hz, 1H), 7.71 (d, J=2.6 Hz, 1H), 7.56 (d, J=1.8 Hz, 1H), 7.16 (dd, J=9.0, 2.6 Hz, 1H), 3.93 (s, 3H), 3.41 (s, 3H), 2.49 (s, 3H), 2.33 (s, 3H)

112

Example 73

3-(3,5-dimethyl-4-isoxazolyl)-5-((cis-2,6-dimethyl-4-morpholinyl)carbonyl)-9-(methylsulfonyl)-7-(trifluoromethyl)-9H-carbazole-1-carboxamide

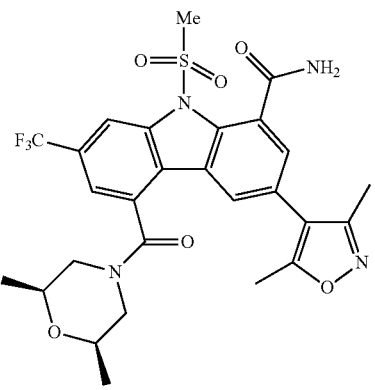

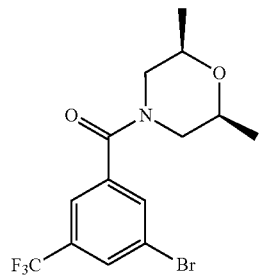

Step 73a: (3-bromo-5-(trifluoromethyl)phenyl)(cis-2,6-dimethylmorpholino) methanone To a solution of 3-bromo-5-(trifluoromethyl)benzoic acid (0.250 g, 0.929 mmol) in DCM (4.7 ml) at 0° C. was added oxalyl chloride (0.102 ml, 1.162 mmol) and 1 drop of DMF. After 2 hours, cis-2,6-dimethylmorpholine (0.268 g, 2.323 mmol) in DCM (0.4 mL) was added. After 2.5 hours, the reaction was warmed to room temperature. After 2.5 hours, cis-2,6-dimethylmorpholine (0.268 g, 2.323 mmol) was added and the reaction was stirred overnight at room temperature. The reaction was washed twice with 1M HCl and once with water/brine. The organic layer was dried with sodium sulfate and concentrated. The material was dissolved in DCM, washed twice with 1 M HCl, dried with sodium sulfate and concentrated to give (3-bromo-5-(trifluoromethyl)phenyl)(cis-2,6-dimethylmorpholino)methanone (0.265 g, 0.724 mmol, 78% yield).

HPLC RT=0.99 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=366 [M+H]$^+$.

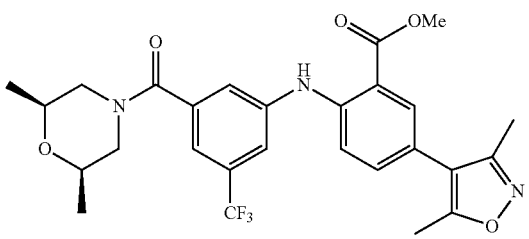 [SMILES: COC(=O)c1cc(-c2c(C)noc2C)ccc1Nc1cc(C(=O)N2C[C@@H](C)O[C@@H](C)C2)cc(C(F)(F)F)c1]

Step 73b: Methyl 5-(3,5-dimethylisoxazol-4-yl)-2-((3-(cis-2,6-dimethylmorpholine-4-carbonyl)-5-(trifluoromethyl)phenyl)amino)benzoate A solution of (3-bromo-5-(trifluoromethyl)phenyl)(cis-2,6-dimethylmorpholino) methanone (0.265 g, 0.724 mmol), methyl 2-amino-5-(3,5-dimethylisoxazol-4-yl)benzoate (0.137 g, 0.557 mmol), and $Cs_2CO_3$ (0.363 g, 1.113 mmol) was degassed with bubbling nitrogen. Chloro(2-dicyclohexylphosphino-2',4',6'-triisopropyl-1,1'-biphenyl)[2-(2'-amino-1,1'-biphenyl)]palladium(II) (0.022 g, 0.028 mmol) was added, then the reaction was heated to 100° C. overnight. The reaction was cooled, then diluted with water and extracted twice with EtOAc. The organic layers were dried with sodium sulfate and evaporated. The residue was purified via ISCO (24 g column; Hex/EtOAc; 0 to 75% gradient) to give methyl 5-(3,5-dimethylisoxazol-4-yl)-2-((3-(cis-2,6-dimethylmorpholine-4-carbonyl)-5-(trifluoromethyl)phenyl)amino)benzoate (0.280 g, 0.527 mmol, 95% yield).

HPLC RT=1.09 min Column: Waters Acquity UPLC BEH C18, 2.1×50 mm, 1.7-µm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=532 [M+H]+.

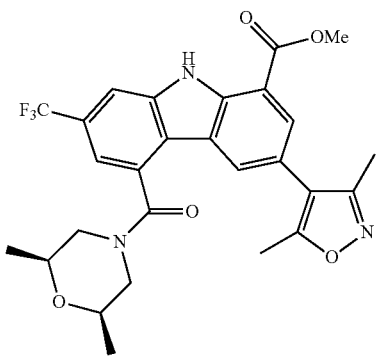

Step 73c: methyl 3-(3,5-dimethylisoxazol-4-yl)-5-(cis-2,6-dimethylmorpholine-4-carbonyl)-7-(trifluoromethyl)-9H-carbazole-1-carboxylate Methyl 5-(3,5-dimethylisoxazol-4-yl)-2-((3-(cis-2,6-dimethylmorpholine-4-carbonyl)-5-(trifluoromethyl)phenyl)amino)benzoate (0.280 g, 0.527 mmol) was dissolved in pivalic acid (1.756 ml). Palladium(II) acetate (0.012 g, 0.053 mmol) and potassium carbonate (7.28 mg, 0.053 mmol) were added, then the reaction was heated to 110° C. overnight in a vial that was partially open to air. The reaction was cooled to room temperature, diluted with MeOH, and filtered through a membrane filter. The filtrate was concentrated. The residue was purified via ISCO (40 g column; Hex/EtOAc; 0 to 65% gradient). Mixed fractions were collected. The residue was purified via ISCO (40 g column; Hex/EtOAc; 0 to 75% gradient) to give methyl 3-(3,5-dimethylisoxazol-4-yl)-5-(cis-2,6-dimethylmorpholine-4-carbonyl)-7-(trifluoromethyl)-9H-carbazole-1-carboxylate (0.106 g, 0.200 mmol, 38.0% yield).

HPLC RT=1.04 min Column: Waters Acquity UPLC BEH C18, 2.1×50 mm, 1.7-µm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=530 [M+H]+.

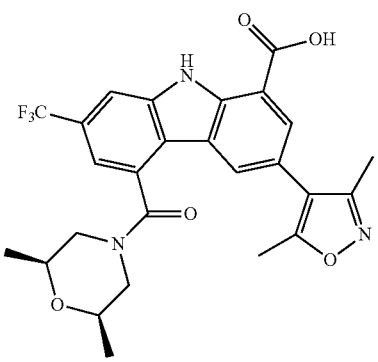

Step 73d: 3-(3,5-dimethylisoxazol-4-yl)-5-(cis-2,6-dimethylmorpholine-4-carbonyl)-7-(trifluoromethyl)-9H-carbazole-1-carboxylic acid To a solution of methyl 3-(3,5-dimethylisoxazol-4-yl)-5-(cis-2,6-dimethylmorpholine-4-carbonyl)-7-(trifluoromethyl)-9H-carbazole-1-carboxylate (0.096 g, 0.181 mmol) in THF (1.450 ml) and water (0.363 ml) was added lithium hydroxide hydrate (0.061 g, 1.450 mmol). The reaction was stirred overnight at room temperature. The reaction was quenched with 1 M HCl and extracted twice with EtOAc. The organic layer was concentrated to give 3-(3,5-dimethylisoxazol-4-yl)-5-(cis-2,6-dimethylmorpholine-4-carbonyl)-7-(trifluoromethyl)-9H-carbazole-1-carboxylic acid (0.058 g, 0.113 mmol, 62.1% yield), which was taken on without further purification. HPLC RT=0.94 min Column: Waters Acquity UPLC BEH C18, 2.1×50 mm, 1.7-µm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=516 [M+H]+.

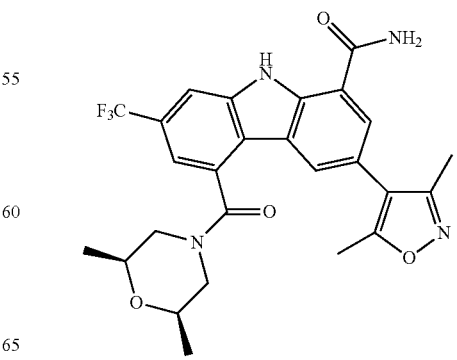

Step 73e: 3-(3,5-dimethylisoxazol-4-yl)-5-(cis-2,6-dimethylmorpholine-4-carbonyl)-7-(trifluoromethyl)-9H-carbazole-1-carboxamide To a solution of 3-(3,5-dimethylisoxazol-4-yl)-5-(cis-2,6-dimethylmorpholine-4-carbonyl)-7-(trifluoromethyl)-9H-carbazole-1-carboxylic acid (0.058 g, 0.113 mmol) in THF (0.938 ml) and DCM (0.188 ml) was added EDC (0.043 g, 0.225 mmol), HOBt (0.034 g, 0.225 mmol), and ammonium hydroxide (0.026 ml, 0.675 mmol). After 4.5 hours, EDC (0.043 g, 0.225 mmol) and HOBt (0.034 g, 0.225 mmol) were added. After 1.5 hours, the reaction was concentrated, then water was added and the slurry was sonicated to give the product (80 mg, 138%), which was taken on without further purification.

HPLC RT=0.92 min Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=515 [M+H]+.

To a solution of 3-(3,5-dimethylisoxazol-4-yl)-5-(cis-2,6-dimethylmorpholine-4-carbonyl)-7-(trifluoromethyl)-9H-carbazole-1-carboxamide (0.040 g, 0.078 mmol) in THF (0.777 ml) was added potassium tert-butoxide (1.0M in THF) (0.117 ml, 0.117 mmol). After 5 minutes, methanesulfonyl chloride (0.015 ml, 0.194 mmol) was added. After 40 minutes, the reaction was quenched with MeOH and concentrated. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of the product was 10.8 mg, and its estimated purity by LCMS analysis was 100%.

HPLC RT=1.73 min; Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=593 [M+H]+.

$^1$H NMR (500 MHz, DMSO-d$_6$) δ 8.39 (s, 1H), 8.33 (br. s., 1H), 7.95 (d, J=7.7 Hz, 1H), 7.79 (d, J=14.5 Hz, 1H), 7.74-7.64 (m, 2H), 4.61-4.55 (m, 1H), 4.10 (s, 3H), 2.89 (s, 3H), 2.73 (s, 3H), 2.69-2.57 (m, 1H), 2.48 (s, 2H), 2.29 (d, J=5.7 Hz, 2H), 1.19 (t, J=6.9 Hz, 3H), 0.88 (d, J=5.7 Hz, 3H)

Example 74

9-(cyclopropylsulfonyl)-3-(3,5-dimethyl-4-isoxazolyl)-5-((cis-2,6-dimethyl-4-morpholinyl)carbonyl)-7-(trifluoromethyl)-9H-carbazole-1-carboxamide

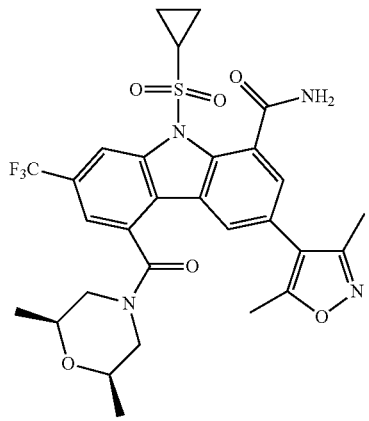

Example 74 was synthesized from Compound 73e and cyclopropanesulfonyl chloride using the same procedure given for Example 73.

HPLC RT=1.82 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=619 [M+H]+.

$^1$H NMR (500 MHz, DMSO-d$_6$) δ 8.33 (br. s., 1H), 8.09 (br. s., 1H), 7.96 (d, J=15.8 Hz, 1H), 7.83 (d, J=15.1 Hz, 1H), 7.74 (d, J=4.7 Hz, 1H), 7.68 (br. s., 1H), 4.63-4.52 (m, 1H), 4.09 (br. s., 1H), 2.89 (s, 1H), 2.73 (s, 3H), 2.69-2.56 (m, 3H), 2.48 (br. s., 2H), 2.29 (d, J=6.1 Hz, 2H), 1.43 (br. s., 2H), 1.33 (d, J=7.4 Hz, 2H), 1.20 (t, J=7.1 Hz, 3H), 0.88 (d, J=6.1 Hz, 3H)

Example 75

9-(cyclopropylsulfonyl)-3-(3,5-dimethyl-4-isoxazolyl)-5-((cis-2,6-dimethyl-4-morpholinyl)carbonyl)-7-(trifluoromethoxy)-9H-carbazole-1-carboxamide

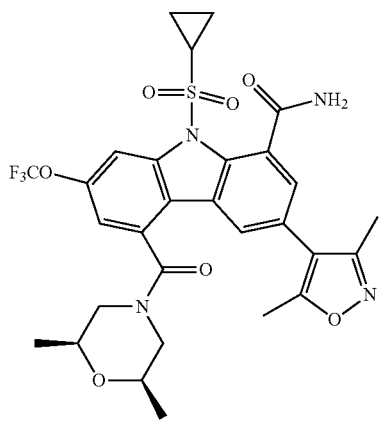

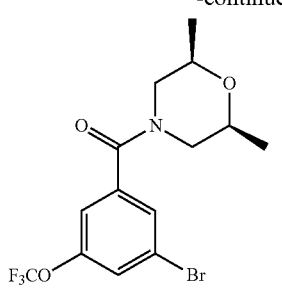

Step 75a: (3-bromo-5-(trifluoromethoxy)phenyl) (cis-2,6-dimethylmorpholino) methanone The above compound was synthesized from 3-bromo-5-(trifluoromethoxy)benzoic acid using the same procedure described for Compound 73a.

HPLC RT=1.02 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=382 [M+H]+.

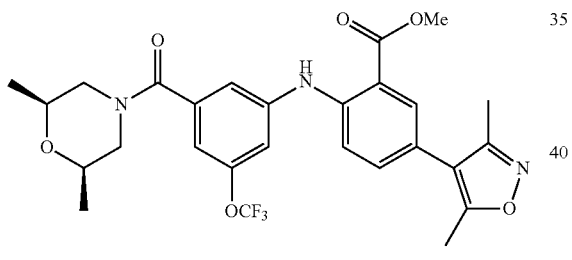

Step 75b: Methyl 5-(3,5-dimethylisoxazol-4-yl)-2-((3-(cis-2,6-dimethylmorpholine-4-carbonyl)-5-(trifluoromethoxy)phenyl)amino)benzoate Methyl 5-(3,5-dimethylisoxazol-4-yl)-2-((3-(cis-2,6-dimethylmorpholine-4-carbonyl)-5-(trifluoromethoxy)phenyl)amino)benzoate was synthesized from Compound 72a and Compound 75a using the same procedure described for Compound 73b.

HPLC RT=1.11 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=548 [M+H]+.

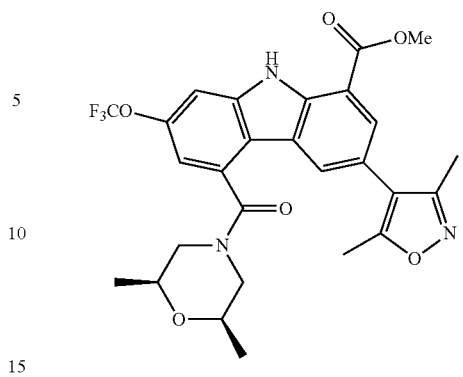

Step 75c: Methyl 3-(3,5-dimethylisoxazol-4-yl)-5-(cis-2,6-dimethylmorpholine-4-carbonyl)-7-(trifluoromethoxy)-9H-carbazole-1-carboxylate Methyl 3-(3,5-dimethylisoxazol-4-yl)-5-(cis-2,6-dimethylmorpholine-4-carbonyl)-7-(trifluoromethoxy)-9H-carbazole-1-carboxylate was synthesized from Compound 75b using the same procedure described for Compound 73c.

HPLC RT=1.06 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=546[M+H]+.

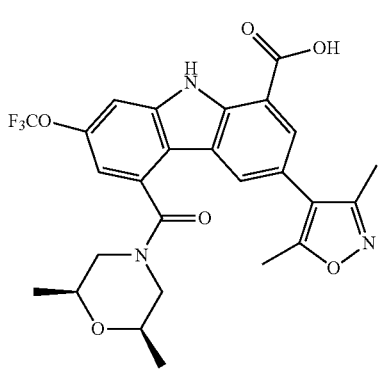

Step 75d: 3-(3,5-dimethylisoxazol-4-yl)-5-(cis-2,6-dimethylmorpholine-4-carbonyl)-7-(trifluoromethoxy)-9H-carbazole-1-carboxylic acid 3-(3,5-dimethylisoxazol-4-yl)-5-(cis-2,6-dimethylmorpholine-4-carbonyl)-7-(trifluoromethoxy)-9H-carbazole-1-carboxylic acid was synthesized from Compound 75c using the same procedure described for Compound 73d.

HPLC RT=0.95 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=532[M+H]+.

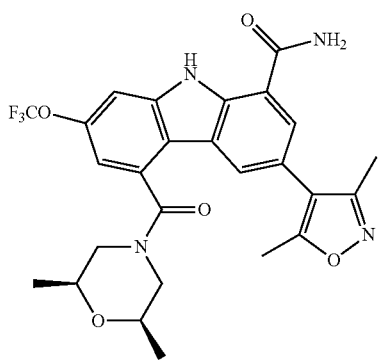

Step 75e: 3-(3,5-dimethylisoxazol-4-yl)-5-(cis-2,6-dimethylmorpholine-4-carbonyl)-7-(trifluoromethoxy)-9H-carbazole-1-carboxamide 3-(3,5-dimethylisoxazol-4-yl)-5-(cis-2,6-dimethylmorpholine-4-carbonyl)-7-(trifluoromethoxy)-9H-carbazole-1-carboxamide was synthesized from Compound 75d using the same procedure described for Compound 73e.

HPLC RT=0.94 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=531[M+H]$^+$.

Compound 75 was synthesized from Compound 75e and cyclopropanesulfanyl chloride using the same procedure described for Compound 73.

HPLC RT=1.87 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=635 [M+H]$^+$.

$^1$H NMR (500 MHz, DMSO-d$_6$) δ 8.31 (s, 1H), 7.93 (d, J=15.5 Hz, 1H), 7.81 (br. s., 1H), 7.70 (s, 1H), 7.62 (br. s., 1H), 7.56-7.48 (m, 1H), 4.57 (dd, J=19.5, 13.1 Hz, 1H), 4.05 (d, J=7.7 Hz, 1H), 3.77-3.63 (m, 1H), 2.88 (s, 3H), 2.72 (s, 3H), 2.47 (s, 2H), 2.29 (d, J=6.7 Hz, 2H), 1.45 (br. s., 2H), 1.30 (d, J=8.1 Hz, 2H), 1.19 (t, J=7.1 Hz, 3H), 0.89 (d, J=6.1 Hz, 3H).

Example 76

3-(3,5-dimethyl-4-isoxazolyl)-5-((cis-2,6-dimethyl-4-morpholinyl)carbonyl)-9-(methylsulfonyl)-7-(trifluoromethoxy)-9H-carbazole-1-carboxamide

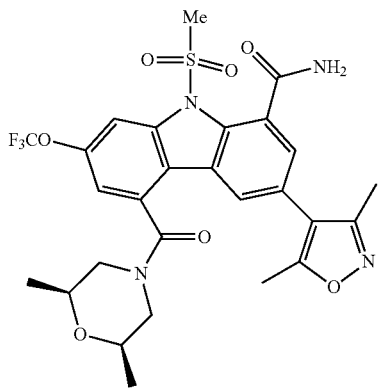

Example 76 was synthesized from Compound 75e using the same procedure described for Example 73.

HPLC RT=1.78 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=609 [M+H]$^+$.

Example 77

9-(cyclopropylsulfonyl)-3-(3,5-dimethyl-4-isoxazolyl)-6-(methylsulfonyl)-9H-carbazole-1-carboxamide

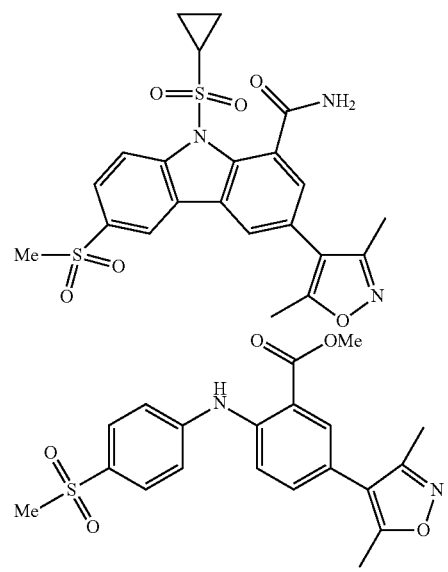

Step 77a: Methyl 5-(3,5-dimethylisoxazol-4-yl)-2-((4-(methylsulfonyl)phenyl)amino)benzoate Methyl 5-(3,5-dimethylisoxazol-4-yl)-2-((4-(methylsulfonyl)phenyl)amino)benzoate was synthesized from Compound 72a and 1-bromo-4-(methylsulfonyl)benzene using the same procedure described for Compound 72b.

HPLC RT=0.92 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=401 [M+H]$^+$.

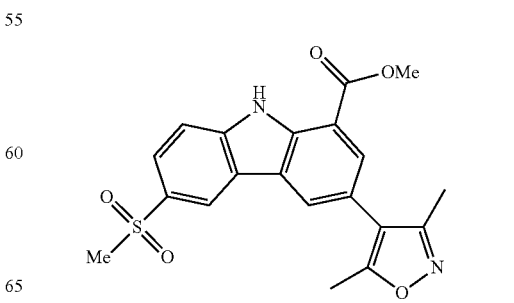

Step 77b: Methyl 3-(3,5-dimethylisoxazol-4-yl)-6-(methylsulfonyl)-9H-carbazole-1-carboxylate Methyl 3-(3,5-dimethylisoxazol-4-yl)-6-(methylsulfonyl)-9H-carbazole-1-carboxylate was synthesized from Compound 77a using the same procedure described for Compound 72c.

HPLC RT=0.88 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=399 [M+H]$^+$.

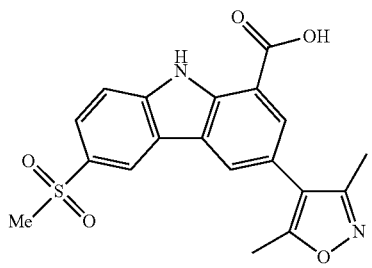

Step 77c: 3-(3,5-dimethylisoxazol-4-yl)-6-(methylsulfonyl)-9H-carbazole-1-carboxylic acid 3-(3,5-dimethylisoxazol-4-yl)-6-(methylsulfonyl)-9H-carbazole-1-carboxylic acid was synthesized from Compound 77b using the same procedure described for Compound 72d.

HPLC RT=0.76 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=385 [M+H]$^+$.

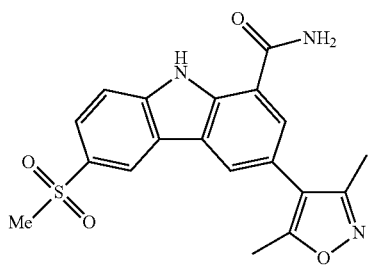 [SMILES: Cc1noc(C)c1-c1cc(C(=O)O)c2[nH]c3ccc(S(C)(=O)=O)cc3c2c1]

Step 77d: 3-(3,5-dimethylisoxazol-4-yl)-6-(methylsulfonyl)-9H-carbazole-1-carboxamide 3-(3,5-dimethylisoxazol-4-yl)-6-(methylsulfonyl)-9H-carbazole-1-carboxamide was synthesized from Compound 77c using the same procedure described for Compound 72e.

HPLC RT=0.73 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=384 [M+H]$^+$.

The final product was synthesized from Compound 77d and cyclopropanesulfanyl chloride using the same procedure described for Example 72.

HPLC RT=1.15 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=488[M+H]$^+$.

$^1$H NMR (500 MHz, DMSO-d$_6$) δ 8.63 (d, J=8.4 Hz, 1H), 8.51 (s, 1H), 8.32-8.24 (m, 2H), 8.05 (d, J=7.1 Hz, 1H), 7.71 (s, 1H), 7.64 (s, 1H), 4.03 (br. s., 1H), 3.35 (s, 3H), 2.50 (br. s., 3H), 2.33 (s, 3H), 1.40 (br. s., 2H), 1.30 (d, J=5.7 Hz, 2H)

Example 78

9-(cyclopropylmethyl)-3-(3,5-dimethyl-4-isoxazolyl)-6-(methylsulfonyl)-9H-carbazole-1-carboxamide

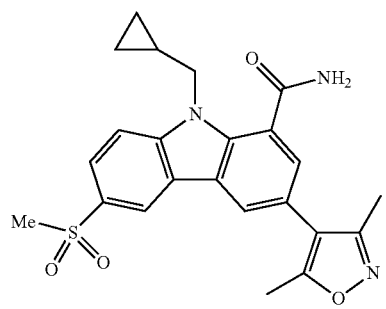 [SMILES: Cc1noc(C)c1-c1cc(C(N)=O)c2c(c1)c1cc(S(C)(=O)=O)ccc1n2CC1CC1]

To a solution of Compound 77d (0.011 g, 0.029 mmol) in acetone (0.287 ml) was added 18C6 (0.758 mg, 2.87 μmol), potassium carbonate (0.016 g, 0.115 mmol), and (bromomethyl)cyclopropane (0.056 ml, 0.574 mmol). The solution was heated to 65° C. overnight. Reaction was cooled, then the solvent was decanted and the solid washed with acetone. The solvent was concentrated and the resulting solid was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 5-minute hold at 100% B; Flow: 20 mL/min. Fractions containing the desired product were combined and dried via centrifugal evaporation. The yield of the product was 6.1 mg.

HPLC RT=1.24 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=438[M+H]$^+$.

$^1$H NMR (500 MHz, DMSO-d$_6$) δ 8.95 (s, 1H), 8.52 (s, 1H), 8.34 (s, 1H), 8.00 (d, J=1.2 Hz, 1H), 7.97-7.93 (m, 1H), 7.91 (s, 1H), 7.50 (d, J=1.8 Hz, 1H), 4.58 (d, J=6.7 Hz, 2H), 3.27 (s, 3H), 2.50-2.49 (s, 3H), 2.33 (s, 3H), 1.31-1.20 (m, 1H), 0.43-0.34 (m, 4H)

Example 79

9-(cyclopropylsulfonyl)-3-(3,5-dimethyl-4-isoxazolyl)-7-(methylsulfonyl)-9H-carbazole-1-carboxamide

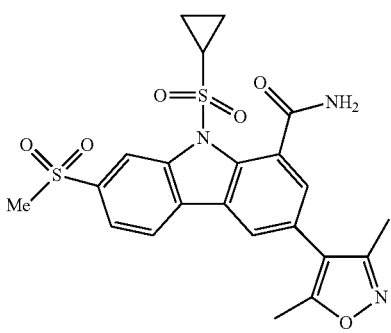

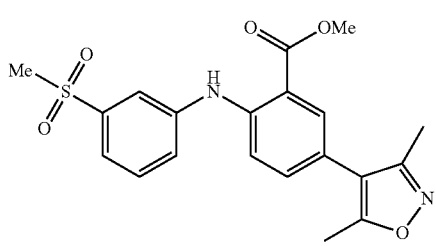

Step 79a: Methyl 5-(3,5-dimethylisoxazol-4-yl)-2-((3-(methylsulfonyl) phenyl)amino)benzoate Methyl 5-(3,5-dimethylisoxazol-4-yl)-2-((3-(methylsulfonyl) phenyl)amino)benzoate was synthesized from Compound 72a and 1-bromo-3-(methylsulfonyl)benzene using the same procedure described for Compound 72b. HPLC RT=0.94 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=401 [M+H]$^+$.

Step 79b: Methyl 3-(3,5-dimethylisoxazol-4-yl)-7-(methylsulfonyl)-9H-carbazole-1-carboxylate

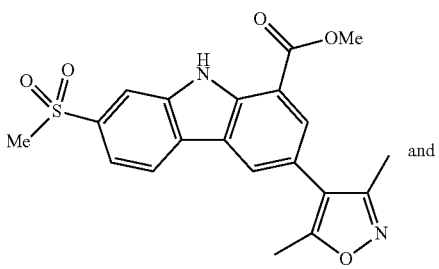 [SMILES: COC(=O)c1cc(-c2c(C)noc2C)cc2c1[nH]c1cc(S(C)(=O)=O)ccc12]

and

Step 79c: Methyl 3-(3,5-dimethylisoxazol-4-yl)-5-(methylsulfonyl)-9H-carbazole-1-carboxylate

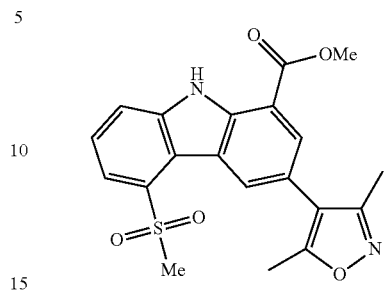

Compounds 79b and 79c were synthesized from Compound 79a using the same procedure described for Compound 72c.

Compound 79b: $^1$H NMR (400 MHz, CHLOROFORM-d) δ 10.34 (s, 1H), 8.28 (d, J=8.1 Hz, 1H), 8.22 (dd, J=9.1, 1.2 Hz, 2H), 8.08 (d, J=1.5 Hz, 1H), 7.87 (dd, J=8.1, 1.5 Hz, 1H), 4.09 (s, 3H), 3.17 (s, 3H), 2.46 (s, 3H), 2.32 (s, 3H)

Compound 79c: $^1$H NMR (400 MHz, CHLOROFORM-d) δ 10.55 (br. s., 1H), 9.03 (d, J=1.3 Hz, 1H), 8.11 (d, J=1.5 Hz, 1H), 8.04 (dd, J=7.7, 0.9 Hz, 1H), 7.89 (dd, J=8.1, 0.9 Hz, 1H), 7.75-7.61 (m, 1H), 4.08 (s, 3H), 3.24 (s, 3H), 2.52 (s, 3H), 2.39 (s, 3H)

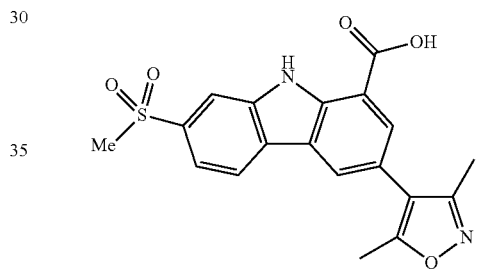

Compound 79d: 3-(3,5-dimethylisoxazol-4-yl)-7-(methylsulfonyl)-9H-carbazole-1-carboxylic acid 3-(3,5-dimethylisoxazol-4-yl)-7-(methylsulfonyl)-9H-carbazole-1-carboxylic acid was synthesized from Compound 79b using the same procedure described for Compound 72d.

HPLC RT=0.79 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=385 [M+H]$^+$.

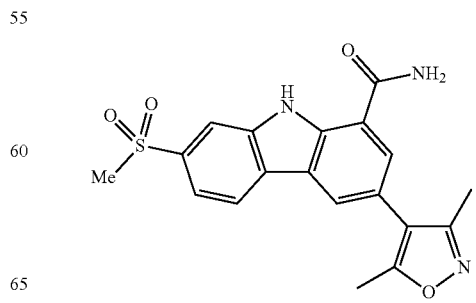

Step 79e: 3-(3,5-dimethylisoxazol-4-yl)-7-(methylsulfonyl)-9H-carbazole-1-carboxamide 3-(3,5-dimethylisoxazol-4-yl)-7-(methylsulfonyl)-9H-carbazole-1-carboxamide was synthesized from Compound 79d using the same procedure described for Compound 72e.

HPLC RT=0.75 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=384 [M+H]$^+$.

9-(cyclopropylsulfonyl)-3-(3,5-dimethyl-4-isoxazolyl)-7-(methylsulfonyl)-9H-carbazole-1-carboxamide was synthesized from Compound 79e using the same procedure described for Example 72.

HPLC RT=1.31 min: Column: Waters Acquity UPLC BEH C18, 2.1×50 mm, 1.7-μm particles; Mobile Phase A: 5:95 acetonitrile:water with 10 mM ammonium acetate;

Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=488[M+H]$^+$.

$^1$H NMR (500 MHz, DMSO-d$_6$) δ 8.63 (d, J=7.9 Hz, 1H), 8.51 (d, J=1.8 Hz, 1H), 8.33-8.25 (m, 2H), 8.05 (d, J=7.9 Hz, 1H), 7.71 (s, 1H), 7.64 (d, J=1.8 Hz, 1H), 4.03 (br. s., 1H), 3.34 (br. s., 3H), 2.49-2.49 (m, 3H), 2.33 (s, 3H), 1.40 (d, J=4.9 Hz, 2H), 1.33-1.24 (m, 2H).

Example 80

9-(cyclopropylmethyl)-3-(3,5-dimethylisoxazol-4-yl)-7-(methylsulfonyl)-9H-carbazole-1-carboxamide

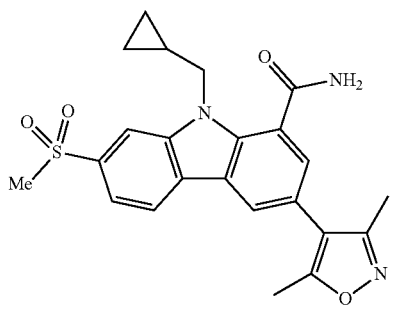 [SMILES: Cc1noc(C)c1-c1cc(C(N)=O)c2c(c1)c1ccc(S(C)(=O)=O)cc1n2CC1CC1]

9-(cyclopropylmethyl)-3-(3,5-dimethylisoxazol-4-yl)-7-(methylsulfonyl)-9H-carbazole-1-carboxamide was synthesized from Compound 79e using the same procedure described for Example 78.

HPLC RT=1.29 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=438[M+H]$^+$.

$^1$H NMR (500 MHz, DMSO-d$_6$) δ 8.33 (d, J=8.1 Hz, 1H), 8.24 (d, J=1.3 Hz, 1H), 8.11 (s, 1H), 8.05 (s, 1H), 7.75-7.64 (m, 1H), 7.56 (d, J=8.1 Hz, 1H), 7.31 (d, J=1.3 Hz, 1H), 4.39 (d, J=7.1 Hz, 2H), 2.66 (s, 3H), 2.27 (s, 3H), 2.10 (s, 3H), 1.10-0.94 (m, 1H), 0.22-0.10 (m, 4H).

Example 81

9-(cyclopropylmethyl)-3-(3,5-dimethyl-4-isoxazolyl)-5-(methylsulfonyl)-9H-carbazole-1-carboxamide

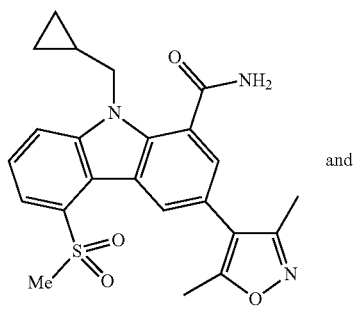 [SMILES: Cc1noc(C)c1-c1cc(C(N)=O)c2c(c1)c1c(S(C)(=O)=O)cccc1n2CC1CC1]

and

Example 82

N,9-bis(cyclopropylmethyl)-3-(3,5-dimethyl-4-isoxazolyl)-5-(methylsulfonyl)-9H-carbazole-1-carboxamide

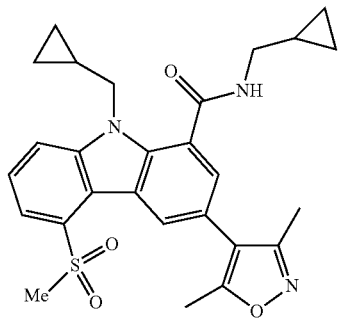

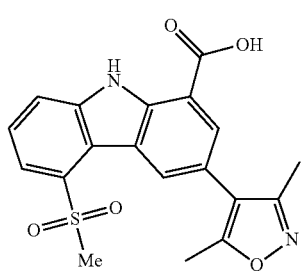

Step 81a: 3-(3,5-dimethylisoxazol-4-yl)-5-(methylsulfonyl)-9H-carbazole-1-carboxylic acid 3-(3,5-dimethylisoxazol-4-yl)-5-(methylsulfonyl)-9H-carbazole-1-carboxylic acid was synthesized from Compound 79c using the same procedure described for Compound 72d.

HPLC RT=0.79 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=385 [M+H]+.

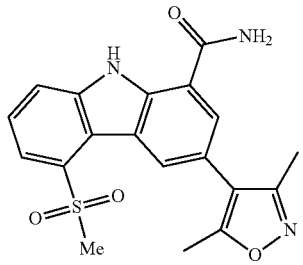 [SMILES: Cc1noc(C)c1-c1cc(C(N)=O)c2[nH]c3cccc(S(C)(=O)=O)c3c2c1]

Step 81b: 3-(3,5-dimethylisoxazol-4-yl)-5-(methylsulfonyl)-9H-carbazole-1-carboxamide 3-(3,5-dimethylisoxazol-4-yl)-5-(methylsulfonyl)-9H-carbazole-1-carboxamide was synthesized from Compound 81a using the same procedure described for Compound 72e.

HPLC RT=0.76 min: Column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 2-98% B over 1 minute, then a 0.5-minute hold at 98% B; Flow: 0.8 mL/min. MS(ESI): m/z=384 [M+H]+.

Compounds 81 and 82 were prepared from Compound 81b by the same procedure described for Compound 78.

Compound 81

HPLC RT=1.32 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=438[M+H]+.

$^1$H NMR (500 MHz, DMSO-d$_6$) δ 8.82 (s, 1H), 8.36 (s, 1H), 8.23 (d, J=8.4 Hz, 1H), 7.95 (s, 1H), 7.89 (d, J=7.4 Hz, 1H), 7.76 (t, J=7.9 Hz, 1H), 7.57 (s, 1H), 4.64 (d, J=7.1 Hz, 2H), 2.51 (d, J=11.1 Hz, 6H), 2.34 (s, 3H), 1.27 (d, J=5.7 Hz, 1H), 0.39 (t, J=8.1 Hz, 4H)

Compound 82

HPLC RT=1.72 min: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min. MS(ESI): m/z=492[M+H]+.

$^1$H NMR (500 MHz, DMSO-d$_6$) δ 9.05 (t, J=5.6 Hz, 1H), 8.82 (s, 1H), 8.23 (d, J=8.4 Hz, 1H), 7.89 (d, J=7.4 Hz, 1H), 7.76 (t, J=8.1 Hz, 1H), 7.51 (s, 1H), 4.60 (d, J=6.7 Hz, 2H), 3.43-3.12 (m, 2H), 2.54-2.48 (m, 6H), 2.34 (s, 3H), 1.31-1.18 (m, 1H), 1.11 (br. s., 1H), 0.54-0.46 (m, 2H), 0.42-0.25 (m, 6H)

Example 83

9-(cyclopropylmethyl)-7-((cis-2,6-dimethyl-4-morpholinyl)carbonyl)-3-(3,5-dimethyl-1H-pyrazol-4-yl)-9H-carbazole-1-carboxamide

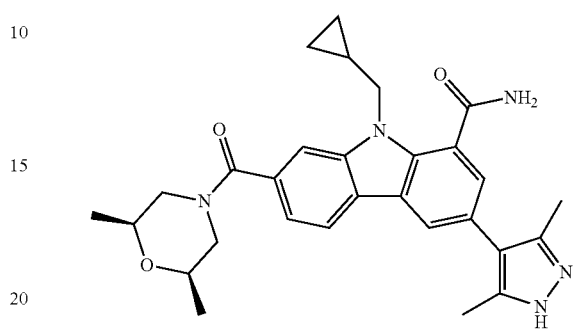

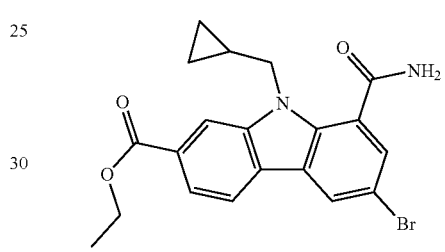

Step 83a: Ethyl 6-bromo-8-carbamoyl-9-(cyclopropylmethyl)-9H-carbazole-2-carboxylate To a solution of ethyl 6-bromo-8-carbamoyl-9H-carbazole-2-carboxylate (1 g, 2.77 mmol) in acetone (10 mL) at room temperature, K$_2$CO$_3$ (0.765 g, 5.54 mmol) and 18-Crown-6 (0.073 g, 0.277 mmol) was added followed by (bromomethyl)cyclopropane (1.869 g, 13.84 mmol). After stirring at 70° C. for 36 h, an additional 380 mg of (bromomethyl)cyclopropane was added and stirring was continued for another 5 h at the same temperature. Completion of the reaction was confirmed by TLC and LC-MS. Reaction mixture was filtered through Celite and solvent was evaporated to get the crude product (2 g). It was mixed with crude product of another identical batch and total 4 g of crude was further triturated with diethyl ether to get ethyl 6-bromo-8-carbamoyl-9-(cyclopropylmethyl)-9H-carbazole-2-carboxylate (2 g, 86%) as a pale yellow solid.

LCMS: HPLC: RT=0.99 min (ACN/H$_2$O with TFA, Acquity BEH C18 1.7 μm (50×2.1) mm, gradient=3 min, wavelength=220 nm); MS (ES): m/z=417 [M+H]+.

1H NMR: 400 MHz (DMSO-d6): δ 8.65 (d, J=2.00 Hz, 1H), 8.37-8.41 (m, 2H), 8.28 (s, 1H), 7.86-7.92 (m, 2H), 7.66 (d, J=2.00 Hz, 1H), 4.56 (d, J=7.20 Hz, 2H), 4.38-4.43 (m, 2H), 1.37-1.41 (m, 3H), 1.17-1.20 (m, 1H), 0.35-0.39 (m, 4H).

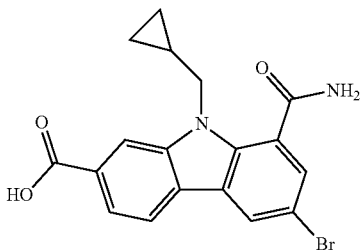 [SMILES: NC(=O)c1cc(Br)cc2c3ccc(C(=O)O)cc3n(CC3CC3)c12]

Step 83b: 6-bromo-8-carbamoyl-9-(cyclopropylmethyl)-9H-carbazole-2-carboxylic acid To a mixture of ethyl 6-bromo-8-carbamoyl-9-(cyclopropylmethyl)-9H-carbazole-2-carboxylate (800 mg, 1.926 mmol) in MeOH (8 mL) and Water (4 mL) was added NaOH (539 mg, 13.48 mmol) and stirred at room temperature for 24 h. Reaction was monitored and completion was confirmed by TLC and LC-MS. Methanol was removed under reduced pressure the residue was acidified using 1.5N aq. HCl. The precipitated solid was filtered and washed with water, dried under vacuo to get 6-bromo-8-carbamoyl-9-(cyclopropylmethyl)-9H-carbazole-2-carboxylic acid (400 mg, 53.6%) as a pale brown solid.

LCMS: HPLC: RT=0.84 min (ACN/H$_2$O with TFA, Acquity BEH C18 1.7 μm (50×2.1) mm, gradient=3 min, wavelength=220 nm); MS (ES): m/z=387 [M+H]$^+$. 1H NMR: 400 MHz (DMSO-d6): δ 13.0 (s, 1H) 8.63 (d, J=2.00 Hz, 1H), 8.35-8.37 (m, 2H), 8.26 (s, 1H), 7.83-7.91 (m, 2H), 7.64-7.65 (m, 1H), 4.54 (d, J=6.80 Hz, 2H), 1.18-1.23 (m, 1H), 0.33-0.37 (m, 4H).

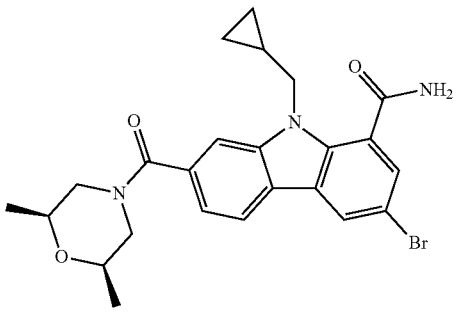 [SMILES: C[C@@H]1CN(C(=O)c2ccc3c4cc(Br)cc(C(N)=O)c4n(CC4CC4)c3c2)C[C@H](C)O1]

Step 83c: 3-bromo-9-(cyclopropylmethyl)-7-(cis-2,6-dimethylmorpholine-4-carbonyl)-9H-carbazole-1-carboxamide To a solution of 6-bromo-8-carbamoyl-9-(cyclopropylmethyl)-9H-carbazole-2-carboxylic acid (450 mg, 1.162 mmol) and cis-2,6-dimethylmorpholine (201 mg, 1.743 mmol) in DMF (4.5 mL) at 0° C. was added 2,4,6-tripropyl-1,3,5,2,4,6-trioxatriphosphprinane-2,4,6-trioxide (50% in EtOAc) (1.48 g, 2.324 mmol) and triethylamine (0.486 mL, 3.49 mmol) and stirred at room temperature for 10 h. Additional 1.48 g of 2,4,6-tripropyl-1,3,5,2,4,6-trioxatriphosphprinane-2,4,6-trioxide (50% in EtOAc) was added and stirring was continued for another 3 h. Reaction was monitored and completion was confirmed by TLC and LC-MS. The reaction mixture was quenched with water (5 mL) and extracted with EtOAc (3×10 mL), organic layer was washed with brine (2×10 mL), dried over anhydrous Na$_2$SO$_4$ and concentrated to get 500 mg of crude product. This crude was mixed with 800 mg of crude product from other batches and purified together by Teledyne ISCO (24 g Redisep silica column) using ethyl acetate as eluent. Fractions containing the product were concentrated to get 550 mg (40%) 3-bromo-9-(cyclopropylmethyl)-7-(cis-2,6-dimethylmorpholine-4-carbonyl)-9H-carbazole-1-carboxamide as a pale yellow solid.

LCMS: HPLC: RT=0.92 min (ACN/H$_2$O with TFA, Acquity BEH C18 1.7 μm (50×2.1) mm, gradient=3 min, wavelength=220 nm); MS (ES): m/z=484.1 [M+H]$^+$.

1H NMR: 400 MHz (DMSO-d6): δ 8.60 (d, J=2.00 Hz, 1H), 8.32-8.34 (m, 2H), 7.89 (s, 1H), 7.76 (s, 1H), 7.61 (d, J=2.00 Hz, 1H), 7.27 (dd, J=1.20, 7.80 Hz, 1H), 4.51 (d, J=7.20 Hz, 2H), 3.62 (s, 2H), 1.09-1.19 (m, 9H), 0.34-0.36 (m, 4H).

To a stirred mixture of K$_2$CO$_3$ (28.5 mg, 0.206 mmol) in Water (1.5 mL) was added 3-bromo-9-(cyclopropylmethyl)-7-(cis-2,6-dimethylmorpholine-4-carbonyl)-9H-carbazole-1-carboxamide (20 mg, 0.041 mmol) in dioxane (2 mL) followed by 3,5-dimethyl-4-(4,4,5,5-tetramethyl-1,3,2-dioxaborolan-2-yl)-1H-pyrazole (11.00 mg, 0.050 mmol). Mixture was degassed with nitrogen and PdCl$_2$(dppf).CH$_2$Cl$_2$ (3.37 mg, 4.13 μmol) added and then heated at 95° C. for 1 hr. Completion of reaction was confirmed by TLC and LC-MS. Reaction mixture was diluted with 5 ml of water and extracted with EtOAc (3×20 mL). Ethyl acetate layer was dried over anhydrous Na$_2$SO$_4$ and solvent was evaporated under reduced pressure to get 60 mg of crude product. Crude product was purified by preparative HPLC to get 9-(cyclopropylmethyl)-3-(3,5-dimethyl-1H-pyrazol-4-yl)-7-(cis-2,6-dimethylmorpholine-4-carbonyl)-9H-carbazole-1-carboxamide (7 mg, 32.9% yield) as a colorless solid.

Preparative HPLC conditions: Column: Xselect C-18 (150 mm×19 mm ID, 5 micron),

Mobile phase A=Buffer: 10 m M NH$_4$OAC in water pH 4.5 with acetic acid, Mobile phase B=Acetonitrile, Flow: 16 ml/min, grad-10-50% mobile phase-B in mobile phase-A in 10 min.

LCMS: HPLC: RT=2.17 min (ACN/H$_2$O with HCOONH$_4$, Ascentis Express C8 2.7 μm (5×2.1) mm, gradient=4 min, wavelength=220 nm); MS (ES): m/z=500 [M+H]$^+$. HPLC RT=6.0 min SUNFIRE C18 (4.6×150) mm, 3.5 micron, mobile Phase A: 0.05% TFA in water: acetonitrile (95:5), mobile Phase B: acetonitrile:0.05% TFA in water (95:5). flow: 1 ml\min, wavelength=220 nm & 254 nm); HPLC RT=6.0 min Sunfire C18 (4.6×150) mm, 3.5 micron, mobile Phase A: 0.05% TFA in water: acetonitrile (95:5), mobile Phase B: acetonitrile:0.05% TFA in water (95:5). flow: 1 ml\min, wavelength=220 nm & 254 nm).

1H NMR: 400 MHz (CD$_3$OD): δ 8.25 (d, J=8.00 Hz, 1H), 8.21 (d, J=4.00 Hz, 1H), 7.69 (s, 1H), 7.52 (d, J=1.60 Hz, 1H), 7.30 (s, 1H), 7.28 (d, J=4.00 Hz, 1H), 4.54 (d, J=28.00 Hz, 3H), 3.67-3.68 (m, 3H), 2.10-0.00 (m, 1H), 2.60-0.00 (m, 1H), 2.36 (s, 6H), 1.10-1.40 (m, 7H), 0.42-0.44 (m, 4H). NH2 protons got exchanged with deuterium in CD$_3$OD.

Example 84

9-(cyclopropylmethyl)-7-((cis-2,6-dimethyl-4-morpholinyl)carbonyl)-3-(1,4-dimethyl-1H-1,2,3-triazol-5-yl)-9H-carbazole-1-carboxamide

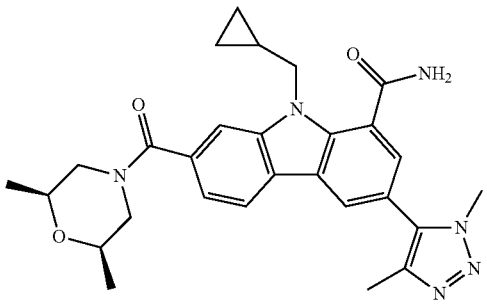

Step 84a: 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide

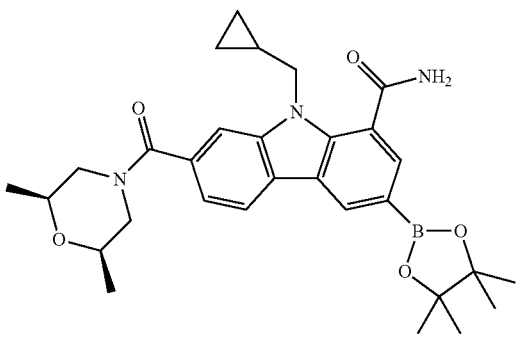

To a solution of 3-bromo-9-(cyclopropylmethyl)-7-(cis-2,6-dimethylmorpholine-4-carbonyl)-9H-carbazole-1-carboxamide (150 mg, 0.310 mmol), bis(pinacolato)diboron (141 mg, 0.557 mmol) in DMSO (2 mL), potassium acetate (137 mg, 1.394 mmol) was added. The mixture was degassed with argon for 5 min and $PdCl_2(dppf)$-$CH_2Cl_2$ (10.20 mg, 0.014 mmol) was added. The mixture was stirred at 80° C. for 4 h. Completion of the reaction was confirmed by TLC and LC-MS. The reaction mixture was brought to room temperature, treated with water (5 mL) and extracted with ethyl acetate (2×5 mL). Ethyl acetate layer was washed with brine, dried over anhydrous $Na_2SO_4$ and concentrated to get the crude product. The crude product was purified by Teledyne ISCO (12 g Redisep silica column) using 60%-80% ethyl acetate/hexane as eluent. Fractions containing product were concentrated to get 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide (70 mg, 42.5% yield) as a pale yellow solid.

LCMS: HPLC: RT=1.879 min (ACN/$H_2O$ with $HCOONH_4$, Ascentis Express C18 (50×2.1 mm; 2.7 u), gradient=4 min, wavelength=220 nm); MS (ES): m/z=532.2 $[M+H]^+$. $^1$H NMR: 400 MHz (CDCl$_3$): δ 8.71 (d, J=1.60 Hz, 1H), 8.18 (d, J=10.40 Hz, 1H), 8.09 (d, J=1.60 Hz, 1H), 7.56 (s, 1H), 7.30-7.33 (m, 1H), 6.20 (s, 1H), 5.85 (s, 1H), 4.55 (d, J=8.80 Hz, 2H), 3.66 (br m, 4H), 1.50 (s, 12H), 1.10-1.18 (m, 9H), 0.33-0.45 (m, 4H).

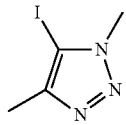

Step 84b: 1,4-dimethyl-1H-1,2,3-triazole 1,4-dimethyl-1H-1,2,3-triazole was synthesized following procedure described in patent WO2008/98104A1. To a stirred solution of 1,4-dimethyl-1H-1,2,3-triazole (50 mg, 0.515 mmol) in THF (1 mL) at −78° C., nBuLi (0.386 mL, 0.618 mmol) was added and stirred 1 hr at −78° C. A solution of Iodine (144 mg, 0.566 mmol) in 0.2 ml of THF was added and stirred at −78° C. for 1 hr. Reaction mixture was slowly warmed to RT over 3 h. It was quenched with 5 ml of saturated aqueous $NH_4Cl$ and was extracted with diethyl ether (2×10 mL), dried over anhydrous $Na_2SO_4$. Diethyl ether was evaporated to get 5-iodo-1,4-dimethyl-1H-1,2,3-triazole (75 mg, 65%) as an yellow solid.

$^1$H NMR: 400 MHz, CDCl$_3$: δ 4.00 (s, 3H), 2.32 (s, 3H).

A mixture of 9-(cyclopropylmethyl)-7-(cis-2,6-dimethylmorpholine-4-carbonyl)-3-(4,4,5,5-tetramethyl-1,3,2-dioxaborolan-2-yl)-9H-carbazole-1-carboxamide (20 mg, 0.038 mmol), 5-iodo-1,4-dimethyl-1H-1,2,3-triazole (12.59 mg, 0.056 mmol) and $K_2CO_3$ (15.60 mg, 0.113 mmol) in dioxane (1 mL) and water (0.3 mL), was degassed with argon for 5 min and $PdCl_2(dppf)$, $CH_2Cl_2$ (2.75 mg, 3.76 μmol) was added. The mixture was heated to 95° C. for 4 h. Completion of reaction was confirmed by TLC and LC-MS. Reaction mixture was allowed to warm to RT and diluted with ethyl acetate (5 mL), washed with brine (2×5 mL), dried over anhydrous $Na_2SO_4$ and concentrated to get the crude product.

The crude product was purified by preparative HPLC and lyophilized to get 9-(cyclopropylmethyl)-7-((cis-2,6-dimethyl-4-morpholinyl)carbonyl)-3-(1,4-dimethyl-1H-1,2,3-triazol-5-yl)-9H-carbazole-1-carboxamide (2.15 mg, 11%) as a colorless solid. Preparative HPLC conditions: Column: Symmetry C18 (19×250) mm×5μ; solvent A: 10 mM NH4OAc, pH 4.5; solvent B: ACN; Flow: 15.0 mL/min; Gradient: Time (min) % B—0/10, 10/50, 15/100

LCMS: RT=2.088 min (ACN/$H_2O$ with 10 mM Ammonium hydrogen carbonate, X-bridge BEH C18 2.5 mm (2.1×50) mm, gradient=3 min, wavelength=254 nm); MS (ES):m/z=501.5 $[M+H^+]$.

HPLC: 95/5 to 5/95 $H_2O$/$CH_3CN$/0.05% TFA, flow=1 mL/min, gradient=15 min, Sunfire C$_{18}$ 3.5 um, 4.6×150 mm: RT=7.483 min; Xbridge Phenyl 3.5 um, 4.6×150 mm: RT=6.669 min.

$^1$H NMR: 400 MHz (CD$_3$OD): δ 8.38 (d, J=2.00 Hz, 1H), 8.32 (d, J=8.00 Hz, 1H), 7.75 (s, 1H), 7.61 (d, J=2.00 Hz, 1H), 7.33 (dd, J=1.20, 8.00 Hz, 1H), 4.60 (d, J=6.80 Hz, 2H), 4.04 (s, 3H), 3.64 (s, 3H), 2.94 (s, 1H), 2.66 (s, 1H), 2.35 (s, 3H), 1.05-1.34 (m, 8H), 0.41-0.47 (m, 4H).

Example 85

9-(cyclopropylmethyl)-3-(3,5-dimethyl-4-isoxazolyl)-7-((cis-2,6-dimethyl-4-morpholinyl)carbonyl)-1-(1H-1,2,4-triazol-3-yl)-9H-carbazole

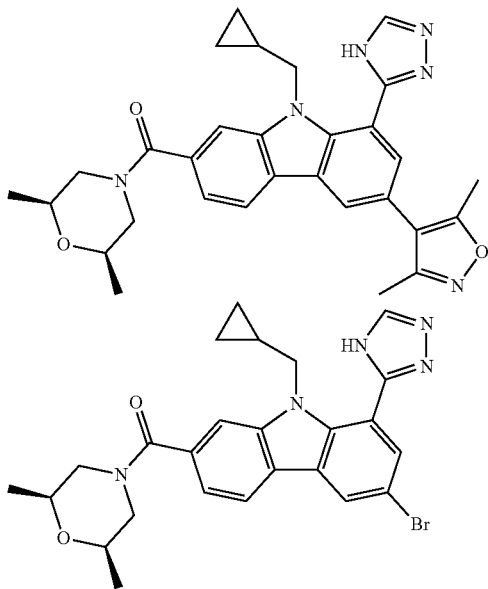

Step 85a: (6-bromo-9-(cyclopropylmethyl)-8-(4H-1,2,4-triazol-3-yl)-9H-carbazol-2-yl)(cis-2,6-dimethylmorpholino)methanone 3-bromo-9-(cyclopropylmethyl)-7-(cis-2,6-dimethylmorpholine-4-carbonyl)-9H-carbazole-1-carboxamide (50 mg, 0.103 mmol) and 1,1-dimethoxy-N,N-dimethylmethanamine (2.2 mL, 0.103 mmol) were mixed and stirred at 80° C. for 3 h. The solvent was evaporated and acetic acid (1 ml, 17.47 mmol) hydrazine (HCl salt) (3.24 µl, 0.103 mmol) were added and allowed stir at 90° C. for 2 h. The solvent was evaporated under reduced pressure and the crude material was purified by ISCO (24 g silica, 50-70% Ethyl acetate:Hexane) to get (6-bromo-9-(cyclopropylmethyl)-8-(4H-1,2,4-triazol-3-yl)-9H-carbazol-2-yl)(cis-2,6-dimethylmorpholino)methanone (50 mg).

LCMS: HPLC: RT=0.94 min (ACN/H$_2$O with NH$_4$OAc, Acquity BEH C18 1.7 µm (50×2.1) mm, gradient=3 min, wavelength=220 nm); MS (ES): m/z=508.0 [M+H]$^+$.

$^1$H NMR: 400 MHz (DMSO-d6): δ 8.64-8.65 (m, 2H), 8.36 (d, J=8.00 Hz, 1H), 7.74 (s, 1H), 7.68-7684.00 (m, 1H), 7.27-7.29 (m, 1H), 4.37 (d, J=6.80 Hz, 3H), 3.61 (s, 4H), 2.85 (s, 1H), 0.97-1.24 (m, 6H), 0.61-0.65 (m, 1H), 0.14 (d, J=1.20 Hz, 2H), 0.12 (d, J=1.60 Hz, 2H).

(6-bromo-9-(cyclopropylmethyl)-8-(4H-1,2,4-triazol-3-yl)-9H-carbazol-2-yl)(cis-2,6-dimethylmorpholino)methanone (15 mg, 0.030 mmol), 3,5-dimethyl-4-(4,4,5,5-tetramethyl-1,3,2-dioxaborolan-2-yl)isoxazole (7.24 mg, 0.032 mmol), and K$_2$CO$_3$ (12.23 mg, 0.089 mmol) was taken in dioxane (1 mL) and Water (0.2 mL). The mixture was degassed with argon for 10 min and then PdCl$_2$(dppf).CH$_2$Cl$_2$ (2.159 mg, 2.95 µmol) was added. The mixture was heated at 90° C. for 1 h. Completion of the reaction was confirmed by TLC and LC-MS. The reaction mixture was cooled to room temperature and treated with water (5 mL), extracted with ethyl acetate (3×5 mL), washed with brine (5 mL), dried over anhydrous Na$_2$SO$_4$ and evaporated under reduced pressure to get crude product.

Crude product was purified by Teledyne ISCO (12 g silica column, 50-90% ethyl acetate hexane) to get 7 mg of 9-(cyclopropylmethyl)-3-(3,5-dimethyl-4-isoxazolyl)-7-((cis-2,6-dimethyl-4-morpholinyl)carbonyl)-1-(1H-1,2,4-triazol-3-yl)-9H-carbazole as a colorless solid.

LCMS: HPLC: RT=1.996 min (ACN/H$_2$O with HCOONH$_4$, Ascentis Express C18 (50×2.1 mm-2.7 µm, gradient=4 min, wavelength=254 nm); MS (ES): m/z=525.0 [M+H]$^+$.

HPLC RT=8.460 min XBridge Phenyl (4.6×150) mm, 3.5 micron, Mobile Phase A: 0.05% TFA in water:acetonitrile (95:5), Mobile Phase B: Acetonitrile:0.05% TFA in water (95:5), FLOW: 1 ml\min, wavelength=220 nm&254 nm);

HPLC RT=9.096 min SUNFIRE C18 (4.6×150) mm, 3.5 micron, mobile Phase A: 0.05% TFA in water:acetonitrile (95:5), mobile Phase B: acetonitrile: 0.05% TFA in water (95:5) flow: 1 ml\min, wavelength=220 nm & 254 nm).

$^1$H NMR: 400 MHz (CD$_3$OD): δ 8.77 (s, 1H), 8.31-8.35 (m, 3H), 7.68 (s, 1H), 7.54 (s, 1H), 7.33-7.35 (m, 1H), 4.59 (s, 1H), 4.31-4.32 (m, 2H), 3.65-3.69 (m, 3H), 2.94-0.00 (m, 1H), 2.65-2.66 (m, 1H), 2.50 (s, 3H), 2.35 (s, 3H), 1.36-0.00 (m, 1H), 1.22-1.31 (m, 3H), 1.07-1.19 (m, 3H), 0.93-0.94 (m, 2H), 0.91-0.92 (m, 2H).

Example 86

9-(cyclopropylmethyl)-3-(3,5-dimethyl-3-isoxazolyl)-7-(cis-2,6-dimethylmorpholine-4-carbonyl)-4-fluoro-9H-carbazole-1-carboxamide

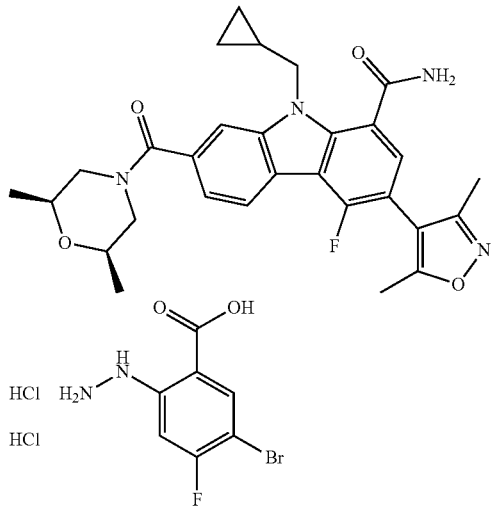

Step 86a: 5-bromo-4-fluoro-2-hydrazinylbenzoic acid dihydrochloride

A solution of sodium nitrite (1.548 g, 22.43 mmol) in H$_2$O, (8 mL) was added dropwise to a cooled (−14° C., ice-salt bath), cream-colored suspension of 2-amino-5-bromo-4-fluorobenzoic acid (5 g, 21.37 mmol) in conc. HCl (28 mL), at such rate that the temperature did not exceed 0° C. (over 12 min). The light brown-colored solution was stirred at 0° C. for 6 min, and was then added in portions to a cooled (−20° C., isopropanol/dry ice) and rapidly stirred solution of Tin (II) chloride (12.15 g, 64.1 mmol) in conc. HCl (8 mL), at such a rate that the temperature stayed between −20° C. and −5° C. (over 30 min). In between additions, the flask containing the diazonium intermediate was kept in a ice/salt bath. After completion of the addition, the reaction mixture was stirred for 45 minutes at −10° C. The resulting cream-colored suspension was warmed up to room temperature and stirred at room temperature for 1 hour. The solid was collected by filtration, washed with water and ether and dried to give a light brown solid 5-bromo-4-fluoro-2-hydrazinylbenzoic acid dihydrochloride (3.2 g, 9.94 mmol, 46.5% yield). HPLC: RT=1.69 min (H$_2$O/MeOH with TFA, Sunfire C18 3.5 mm, 2.1×30 mm, gradient=4 min, wavelength=220 nm); MS (ES):m/z=249.06 [M+1]$^+$.

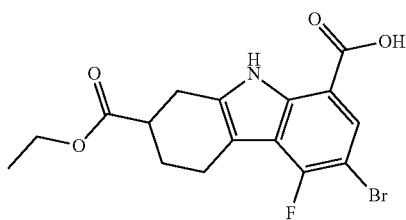 [SMILES: CCOC(=O)C1CCc2c([nH]c3c(C(=O)O)cc(Br)c(F)c23)C1]

Step 86b: 6-bromo-2-(ethoxycarbonyl)-5-fluoro-2,3,4,9-tetrahydro-1H-carbazole-8-carboxylic acid To 5-bromo-4-fluoro-2-hydrazinylbenzoic acid dihydrochloride (2 g, 6.21 mmol) in AcOH (12 mL) was added ethyl 3-oxocyclohexanecarboxylate (1.216 g, 7.14 mmol). The reaction solution was heated at reflux for 3 hours. The reaction solution was cooled to room temperature and concentrated to dryness. The solution was dissolved in ethyl acetate, and the resulting precipitate was filtered to give 6-bromo-2-(ethoxycarbonyl)-5-fluoro-2,3,4,9-tetrahydro-1H-carbazole-8-carboxylic acid (1.15 g, 2.98 mmol, 47.9% yield)

HPLC: RT=3.938 min (H$_2$O/MeOH with TFA, Sunfire C18 3.5 mm, 2.1×30 mm, gradient=4 min, wavelength=220 nm); MS (ES):m/z=386.06 [M+1]$^+$.

$^1$H NMR (400 MHz, METHANOL-d$_4$) δ 7.86 (d, J=6.6 Hz, 1H), 4.85 (m, 2H), 4.21 (dd, J=7.0, 1.3 Hz, 2H), 3.13-2.78 (m, 5H), 2.38-2.14 (m, 1H), 2.10-1.83 (m, 1H), 1.30 (t, J=7.0 Hz, 3H)

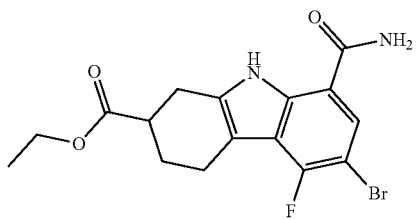 [SMILES: CCOC(=O)C1CCc2c([nH]c3c(C(N)=O)cc(Br)c(F)c23)C1]

Step 86c: Ethyl 6-bromo-8-carbamoyl-5-fluoro-2,3,4,9-tetrahydro-1H-carbazole-2-carboxylate To 6-bromo-2-(ethoxycarbonyl)-5-fluoro-2,3,4,4a,9,9a-hexahydro-1H-carbazole-8-carboxylic acid (1.1 g, 2.85 mmol) in THF (100 mL) and DCM (20.00 mL) was added EDC (2.184 g, 11.39 mmol) and HOBt (1.745 g, 11.39 mmol). The reaction solution was stirred at 25° C. for 15 minutes and then added ammonium hydroxide (0.665 mL, 17.09 mmol). The mixture turned into a thick yellow suspension. The solution was kept stirring at 25° C. After 2 hours, the reaction was concentrated to minimal volume. To this was added water and ethyl acetate. The organic layer was separated and the water layer was extracted 2× with ethyl acetate. The combined organic phases were washed with saturated NaCl, dried over Na$_2$SO$_4$, filtered and concentrated. The yellow residue was triturated in ether and a white solid was filtered off and combined with the initial filtered solid (the entire batch was rinsed with ether) to give the total product ethyl 6-bromo-8-carbamoyl-5-fluoro-2,3,4,9-tetrahydro-1H-carbazole-2-carboxylate (1 g, 2.60 mmol, 91% yield)

HPLC: RT=3.56 min (H$_2$O/MeOH with TFA, Sunfire C18 3.5 mm, 2.1×30 mm, gradient=4 min, wavelength=220 nm); MS (ES):m/z=385 [M+1]$^+$;

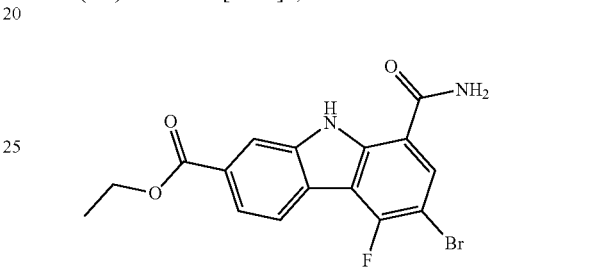

Step 86d: Ethyl 6-bromo-8-carbamoyl-5-fluoro-9H-carbazole-2-carboxylate

In a 40 ml reaction vial was added THF (100 ml), DDQ (1.503 g, 6.49 mmol) and ethyl 6-bromo-8-carbamoyl-5-fluoro-2,3,4,4a,9,9a-hexahydro-1H-carbazole-2-carboxylate (1 g, 2.60 mmol). The reaction was refluxed for 90 minutes. The reaction was concentrated to dryness and then diluted with diluted saturated sodium bicarbonate solution. A white solid began precipitating upon stirring. The solid was filtered off, washed with water and then diethyl ether. The crude product mixture was purified via ISCO (0%-100% of EtOAC/DCM in 15 minutes, 40 g column) to give the product ethyl 6-bromo-8-carbamoyl-5-fluoro-9H-carbazole-2-carboxylate (0.60 g, 1.582 mmol, 61.0% yield).

HPLC: RT=3.76 min (H$_2$O/MeOH with TFA, Sunfire C18 3.5 mm, 2.1×30 mm, gradient=4 min, wavelength=220 nm); MS (ES):m/z=381.03 [M+1]$^+$;

$^1$H NMR (400 MHz, METHANOL-d$_4$) δ 8.45-8.34 (m, 1H), 8.27-8.13 (m, 2H), 8.07-7.89 (m, 1H), 7.85-7.53 (m, 1H), 4.51-4.38 (m, 2H), 1.59-1.42 (m, 4H), 1.09-0.86 (m, 3H).

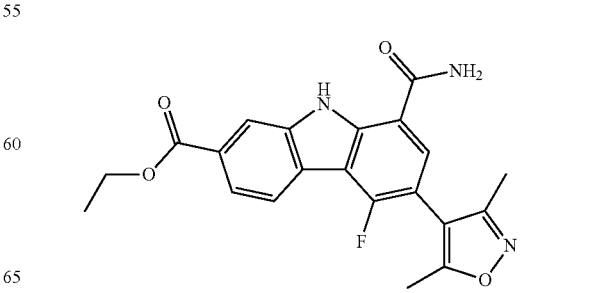

Step 86e: ethyl 8-carbamoyl-6-(3,5-dimethylisoxazol-4-yl)-5-fluoro-9H-carbazole-2-carboxylate In a 100 mL RBF was added ethyl 6-bromo-8-carbamoyl-5-fluoro-9H-carbazole-2-carboxylate (0.45 g, 1.187 mmol), 3,5-dimethyl-4-(4,4,5,5-tetramethyl-1,3,2-dioxaborolan-2-yl)isoxazole (0.397 g, 1.780 mmol) and THF (10 ml). The reaction was degassed (purged with nitrogen and vacuum) and then [1,1'-bis(diphenylphosphino) ferrocene]dichloropalladium(II) (0.043 g, 0.059 mmol) and aqueous tripotassium phosphate (1.187 ml, 3.56 mmol) were added. The reaction was degassed and heated at 80° C. After 16 hours, the reaction was cooled, 10% LiCl in water was added and the resulting precipitate was collected. The crude product mixture was purified via ISCO (0%-100% of EtOAC/DCM in 15 minutes, 40 g column) to give product ethyl 8-carbamoyl-6-(3,5-dimethylisoxazol-4-yl)-5-fluoro-9H-carbazole-2-carboxylate (0.4 g, 1.012 mmol, 85% yield).

HPLC: RT=3.56 min ($H_2O$/MeOH with TFA, Sunfire C18 3.5 mm, 2.1×30 mm, gradient=4 min, wavelength=220 nm); MS (ES):m/z=396.18 [M+1]+.

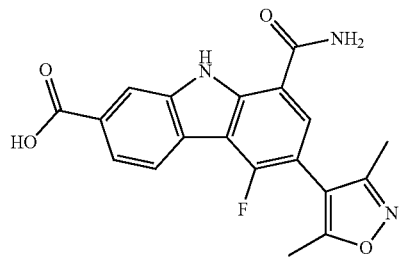 [SMILES: Cc1noc(C)c1-c1cc(C(N)=O)c2[nH]c3cc(C(=O)O)ccc3c2c1F]

Step 86f: 8-carbamoyl-6-(3,5-dimethylisoxazol-4-yl)-5-fluoro-9H-carbazole-2-carboxylic acid To ethyl 8-carbamoyl-6-(3,5-dimethylisoxazol-4-yl)-5-fluoro-9H-carbazole-2-carboxylate (0.4 g, 1.012 mmol) in THF (15 mL) and MeOH (3.00 mL) was added sodium hydroxide (1M in water, 1.012 mL, 10.12 mmol). The reaction solution was stirred at RT for 16 hours. After 16 hours, the reaction was concentrated in vacuo, the residue was redissolved in 1M HCl, the precipitate was filtered to give 8-carbamoyl-6-(3,5-dimethylisoxazol-4-yl)-5-fluoro-9H-carbazole-2-carboxylic acid (300 mg, 0.817 mmol, 81% yield)

HPLC: RT=3.04 min ($H_2O$/MeOH with TFA, Sunfire C18 3.5 mm, 2.1×30 mm, gradient=4 min, wavelength=220 nm); MS (ES):m/z=368.10 [M+1]+;

$^1$H NMR (400 MHz, METHANOL-$d_4$) δ 8.44-8.27 (m, 1H), 8.27-8.16 (m, 1H), 8.01-7.84 (m, 2H), 2.46 (s, 3H), 2.32 (s, 3H)

Step 86 g

In a flask was added 8-carbamoyl-6-(3,5-dimethylisoxazol-4-yl)-5-fluoro-9H-carbazole-2-carboxylic acid (0.2694 g, 0.733 mmol) in DMF (10 mL) was added HCTU (0.437 g, 1.100 mmol), DMAP (0.090 g, 0.733 mmol) and cis-2,6-dimethylmorpholine (0.507 g, 4.40 mmol) in DMF (10 mL). The reaction was stirred at room temperature for 16 hours. To the reaction mixture was added 10% LiCl solution, the brown ppt resulting was filtered, dried and purified further by ISCO (0%-100% of EtOAC/DCM in 15 minutes, 40 g column) to give the product 3-(3,5-dimethylisoxazol-4-yl)-7-(cis-2,6-dimethylmorpholine-4-carbonyl)-4-fluoro-9H-carbazole-1-carboxamide (300 mg, 0.646 mmol, 88% yield)

HPLC: RT=3.22 min ($H_2O$/MeOH with TFA, Sunfire C18 3.5 mm, 2.1×30 mm, gradient=4 min, wavelength=220 nm); MS (ES):m/z=465.13 [M+1]+;

To 3-(3,5-dimethylisoxazol-4-yl)-7-(cis-2,6-dimethylmorpholine-4-carbonyl)-4-fluoro-9H-carbazole-1-carboxamide (52 mg, 0.112 mmol) in acetone (1.0 mL) was potassium carbonate (61.9 mg, 0.448 mmol), 18 Crown 6 (2.96 mg, 0.011 mmol) and (bromomethyl)cyclopropane (0.217 mL, 2.239 mmol). The reaction solution was heated 80° C. for 16 hours. The crude product mixture was purified by preparative HPLC (Reverse phase Shimadzu HPLC system using a LUNA Phenomenex column, 5 g, 100 A°, 19×100 mm), 20% to 80% of Solvent B, (Solvent A (90% water, 10% methanol, 0.1% TFA), Solvent B (10% water, 90% methanol, 0.1% TFA), 10 min gradient, 12 minute run, 25 mL/min) giving the product 9-(cyclopropylmethyl)-3-(3,5-dimethyl-4-isoxazolyl)-7-(cis-2,6-dimethylmorpholine-4-carbonyl)-4-fluoro-9H-carbazole-1-carboxamide (12 mg, 0.022 mmol, 19.64% yield).

LCMS: MeOH/H2O/0.1% TFA, Waters Sunfire C18 2.1× 30 mm, 3.5 u, 4 min gradient, wavelength=220 nm: RT=3.193 min; m/z (M+1)+=519.22

HPLC Purity: 95/5 to 5/95 $H_2O$/$CH_3CN$/0.05% TFA, flow=0.5 mL/min, gradient=15 min Sunfire C18 3.5 um, 3.0×150 mm: RT=10.39 min; Purity @220 nm: 96%; @254 nm: 95% Xbridge Phenyl 3.5 um, 3.0×150 mm: RT=9.736 min; Purity @220 nm: 100%; @254 nm: 95%

$^1$H NMR (400 MHz, METHANOL-$d_4$) δ 8.29 (d, J=7.9 Hz, 1H), 7.77 (s, 1H), 7.53 (d, J=7.3 Hz, 1H), 7.37 (dd, J=8.1, 1.1 Hz, 1H), 4.61 (d, J=6.8 Hz, 3H), 3.84-3.52 (m, 3H), 3.09-2.53 (m, 2H), 2.43 (s, 3H), 2.27 (s, 3H), 1.45-0.95 (m, 9H), 0.56-0.34 (m, 4H).

Example 87

9-(cyclopropylsulfonyl)-3-(3,5-dimethyl-4-isoxazolyl)-6-(4-morpholinylcarbonyl)-9H-carbazole-1-carboxamide

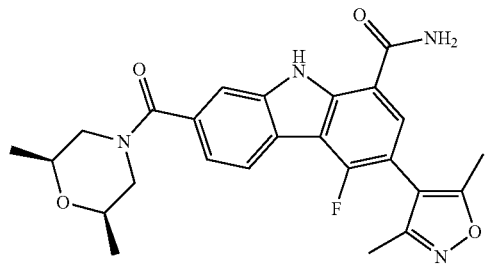

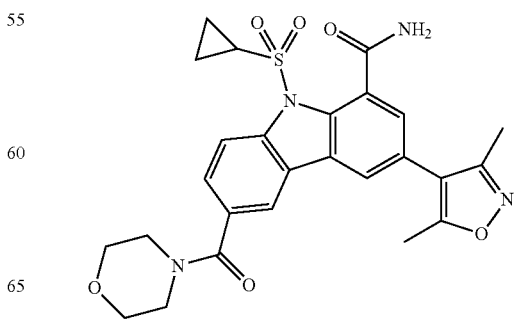

139

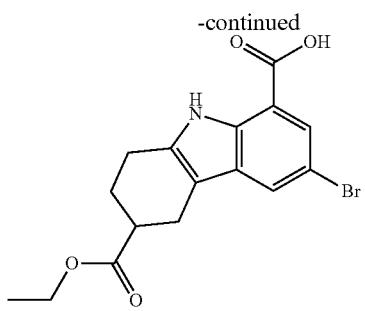

Step 87a: 6-bromo-3-(ethoxycarbonyl)-2,3,4,9-tetrahydro-1H-carbazole-8-carboxylic acid To 5-bromo-2-hydrazinylbenzoic acid dihydrochloride (814 mg, 2.68 mmol) in AcOH (12 mL) was added ethyl 4-oxocyclohexanecarboxylate (524 mg, 3.08 mmol). The reaction was refluxed for 3 hours. The reaction was quenched with water, extracted with ethyl acetate, dried and concentrated to give 6-bromo-3-(ethoxycarbonyl)-2,3,4,9-tetrahydro-1H-carbazole-8-carboxylic acid (1.0 g, 65% pure). Material was used without further purification.

HPLC RT: 1.00 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. LCMS: (ES) m/z 366.08 (M+H).

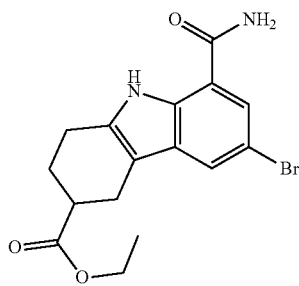 [SMILES: CCOC(=O)C1CCc2[nH]c3c(C(N)=O)cc(Br)cc3c2C1]

Step 87b: Ethyl 6-bromo-8-carbamoyl-2,3,4,9-tetrahydro-1H-carbazole-3-carboxylate To a light suspension of 65% pure 6-bromo-3-(ethoxycarbonyl)-2,3,4,9-tetrahydro-1H-carbazole-8-carboxylic acid (981 mg, 2.68 mmol), EDC (2054 mg, 10.72 mmol), and 1-hydroxybenzotriazole hydrate (1641 mg, 10.72 mmol) in THF/DCM (5/1) (12 mL) was added ammonium hydroxide (2.086 mL, 16.07 mmol) and it turned into a thick light yellow suspension and it was stirred at room temperature. After 5 hours, water was added and the precipitate was collected and dried to give ethyl 6-bromo-8-carbamoyl-2,3,4,9-tetrahydro-1H-carbazole-3-carboxylate 980 mg, 65% purity). Material was used without further purification.

HPLC RT: 0.94 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. LCMS: (ES) m/z 365.08 (M+H)

140

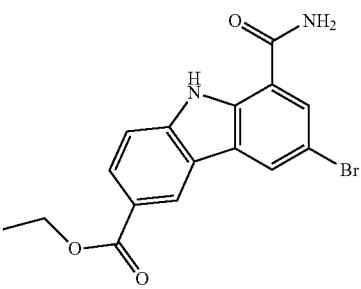 [SMILES: CCOC(=O)c1ccc2[nH]c3c(C(N)=O)cc(Br)cc3c2c1]

Step 87c: Ethyl 6-bromo-8-carbamoyl-9H-carbazole-3-carboxylate

To 65% pure ethyl 6-bromo-8-carbamoyl-2,3,4,9-tetrahydro-1H-carbazole-3-carboxylate (997 mg, 2.73 mmol) in Toluene (12 ml) was added DDQ (1391 mg, 6.01 mmol). The reaction was refluxed for 1.5 hours. The reaction was concentrated to dryness, then water was added. The solid was collected and dried to give ethyl 6-bromo-8-carbamoyl-9H-carbazole-3-carboxylate (1.0 g, contains a DDQ-derived byproduct). Material was used without further purification.

HPLC RT: 0.95 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. LCMS: (ES) m/e 361.08 (M+H).

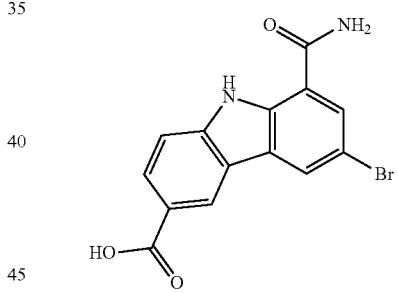

Step 87d: 6-bromo-8-carbamoyl-9H-carbazole-3-carboxylic acid

To ethyl 6-bromo-8-carbamoyl-9H-carbazole-3-carboxylate (980 mg, 2.71 mmol) in THF (5 mL) and MeOH (1 mL) was added sodium hydroxide (10 M in water, 1.357 mL, 13.57 mmol). After 3 hours, additional NaOH was added and the reaction was warmed to 60° C. The reaction was concentrated, 1N HCl was added and the precipitate collected by filtration to give 6-bromo-8-carbamoyl-9H-carbazole-3-carboxylic acid (1.0 g, contains a DDQ-derived byproduct). Material was used without further purification.

HPLC RT: 0.69 min Column: Waters Acquity SDS BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min.

141

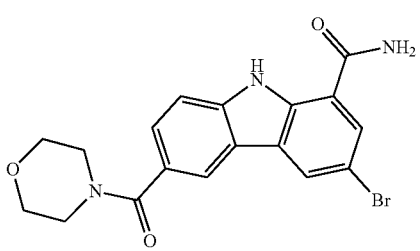 [SMILES: NC(=O)c1cc(Br)cc2c1[nH]c1ccc(C(=O)N3CCOCC3)cc12]

Step 87e: 3-bromo-6-(morpholine-4-carbonyl)-9H-carbazole-1-carboxamide

To 6-bromo-8-carbamoyl-9H-carbazole-3-carboxylic acid (900 mg, 2.70 mmol) in DMF (8 mL) was added HATU (3082 mg, 8.10 mmol), DMAP (990 mg, 8.10 mmol) and morpholine (1412 mg, 16.21 mmol. After 1 hour water was added. The precipitate was collected and washed with water to give 3-bromo-6-(morpholine-4-carbonyl)-9H-carbazole-1-carboxamide (350 mg).

HPLC RT: 0.73 min Column: Waters Acquity SDS BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 2.20 minutes. Flow: 1.11 mL/min. LCMS: (ES) m/z 402.08 (M+H)

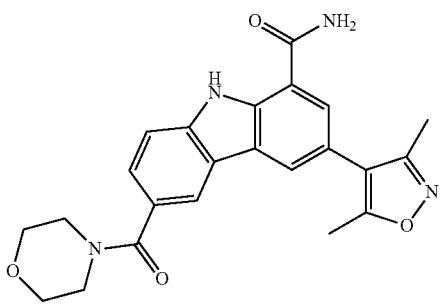 [SMILES: Cc1noc(C)c1-c1cc(C(N)=O)c2[nH]c3ccc(C(=O)N4CCOCC4)cc3c2c1]

Step 87f: 3-(3,5-dimethylisoxazol-4-yl)-6-(morpholine-4-carbonyl)-9H-carbazole-1-carboxamide A septum sealed vial containing 3-bromo-6-(morpholine-4-carbonyl)-9H-carbazole-1-carboxamide (275 mg, 0.684 mmol), 3,5-dimethyl-4-(4,4,5,5-tetramethyl-1,3,2-dioxaborolan-2-yl)isoxazole (229 mg, 1.026 mmol) and (1'1-Bis(diphenyl phosphino)Ferrocene)dichloropalladium (II) (25.01 mg, 0.034 mmol) was vacuum purged with nitrogen (3×). Tetrahydrofuran (20 mL) and 3 M potassium phosphate tribasic (0.684 mL, 2.051 mmol) were added, and the mixture was again vacuum purged with nitrogen (3×). The resulting suspension was warmed to 60° C. and stirred overnight. The mixture was cooled to room temperature, diluted with ethyl acetate, filtered through Celite, transferred to a separatory funnel, washed with water and brine, dried over anhydrous sodium sulfate, filtered and concentrated to provide a dark oil. The oil was dissolved in a minimum of dichloromethane and purified on an ISCO companion chromatography system (24 g silica cartridge, eluting with 0-100% ethyl acetate/heptane, 35 mL/min). Fractions 32-45 were combined to provide 3-(3,5-dimethylisoxazol-4-yl)-6-(morpholine-4-carbonyl)-9H-carbazole-1-carboxamide (93

142 mg, 0.222 mmol, 32.5% yield). $^1$H NMR (400 MHz, CHLOROFORM-d) δ 10.59 (s, 1H), 8.26 (s, 1H), 8.11 (d, J=1.1 Hz, 1H), 7.58 (d, J=1.1 Hz, 2H), 7.53 (d, J=1.3 Hz, 1H), 3.76 (br. s., 8H), 2.45 (s, 3H), 2.31 (s, 3H). LC/MS 419 (m+1).

Potassium t-butoxide (1M THF) (0.155 mL, 0.155 mmol) was added to a room temperature suspension of 3-(3,5-dimethylisoxazol-4-yl)-6-(morpholine-4-carbonyl)-9H-carbazole-1-carboxamide (48 mg, 0.115 mmol) in tetrahydrofuran (1 mL), a precipitate initially forms then dissolves. Cyclopropanesulfonyl chloride (0.033 mL, 0.344 mmol) was added, and the resulting clear yellow solution was stirred at room temperature. After approximately 2 hours, the mixture was concentrated, dissolved in DMF (2 mL), filtered through a 0.45 µM filter, and purified by preparative reverse phase HPLC to provide 9-(cyclopropylsulfonyl)-3-(3,5-dimethyl-4-isoxazolyl)-6-(4-morpholinylcarbonyl)-9H-carbazole-1-carboxamide (42.2 mg, 0.081 mmol, 70.4% yield).

Preparative LC/MS conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation. The yield of the product was 42.2 mg, and its estimated purity by LCMS analysis was 100%. Two analytical LC/MS injections were used to determine the final purity.

HPLC RT: 1.09 min conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min., m/z 523 (m+1).

HPLC RT: 1.09 min: Column: Waters Acquity UPLC BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min, m/z 523 (m+1)

$^1$H NMR (500 MHz, 1:1 methanol-d$_4$:CHLOROFORM-d) δ 8.19 (d, J=1.0 Hz, 1H), 8.10 (d, J=1.5 Hz, 1H), 8.02 (d, J=8.9 Hz, 1H), 7.61 (d, J=2.0 Hz, 1H), 7.60-7.57 (m, 1H), 3.95-3.52 (m, 9H), 2.49 (s, 3H), 2.33 (s, 3H), 1.56-1.37 (m, 2H), 1.24-0.98 (m, 2H)

Example 88

9-(cyclopropylsulfonyl)-3-(3,5-dimethyl-4-isoxazolyl)-7-((cis-2,6-dimethyl-4-morpholinyl)carbonyl)-9H-carbazole-1-carboxamide

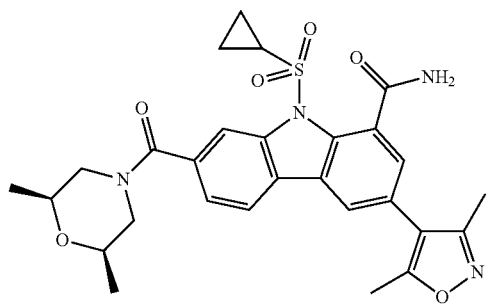

-continued

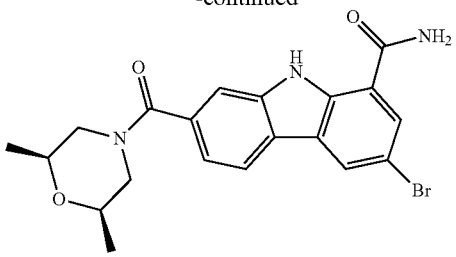

Step 88a: 3-bromo-7-(cis-2,6-dimethylmorpholine-4-carbonyl)-9H-carbazole-1-carboxamide To a solution of 6-bromo-8-carbamoyl-9H-carbazole-2-carboxylic acid (3.60 g, 8.65 mmol) in DMF (30 mL) was added HCTU (10.31 g, 25.9 mmol), DMAP (3.17 g, 25.9 mmol) and cis-2,6-dimethylmorpholine (5.97 g, 51.9 mmol). After 2 hours, 10% LiCl in water was added and the resulting precipitate was collected. The precipitate was washed with water and dried. The product was combined with the product of an identical reaction run using 5.25 g of 6-bromo-8-carbamoyl-9H-carbazole-2-carboxylic acid to give 3-bromo-7-(cis-2,6-dimethylmorpholine-4-carbonyl)-9H-carbazole-1-carboxamide (9.30 g, 99%). HPLC Ret. Time=0.88, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 0-100% B over 1 minute, then a 0.5-minute hold at 100% B; Flow: 0.8 mL/min. MS (ES): m/z=430 [M+H]$^+$.

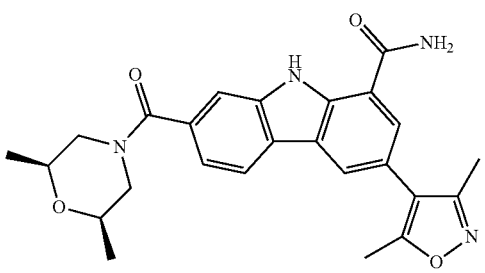

Step 88b: 3-(3,5-dimethylisoxazol-4-yl)-7-(cis-2,6-dimethylmorpholine-4-carbonyl)-9H-carbazole-1-carboxamide A solution of 3-bromo-7-(cis-2,6-dimethylmorpholine-4-carbonyl)-9H-carbazole-1-carboxamide (3.59 g, 8.34 mmol) and 3,5-dimethyl-4-(4,4,5,5-tetramethyl-1,3,2-dioxaborolan-2-yl)isoxazole (2.79 g, 12.51 mmol) in DMF (30 ml) was degassed, and then PdCl$_2$(dppf)-DCM Adduct (0.341 g, 0.417 mmol) and aqueous tripotassium phosphate (8.34 ml, 25.03 mmol) were added. The reaction was degassed and heated at 80° C. After 2 h, the reaction showed all product, and was cooled and 10% LiCl in water was added. The precipitate was collected to give 3-(3,5-dimethylisoxazol-4-yl)-7-(cis-2,6-dimethylmorpholine-4-carbonyl)-9H-carbazole-1-carboxamide (3.70 g), which was used without further purification. HPLC Ret. Time=0.83, column: Waters Acquity UPLC BEH C18, 2.1×50 mm, 1.7-μm particles; Mobile Phase A: water with 0.05% TFA; Mobile Phase B: acetonitrile with 0.05% TFA; Gradient: 0-100% B over 1 minute, then a 0.5-minute hold at 100% B; Flow: 0.8 mL/min. MS (ES): m/z=447 [M+H]$^+$.

To an SCP tube was added 3-(3,5-dimethylisoxazol-4-yl)-7-(cis-2,6-dimethylmorpholine-4-carbonyl)-9H-carbazole-1-carboxamide (120 mg, 0.269 mmol), DMF (1.0 mL) and sodium hydride (43.0 mg, 1.075 mmol). The reaction was allowed to stir at room temperature for 15 min then cyclopropanesulfonyl chloride (132 mg, 0.941 mmol) was added. The reaction mixture was stirred at room temperature for 1 h. LCMS shows about 30% product. Water was added and the precipitate collected.

The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation.

The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation.

The yield of 9-(cyclopropylsulfonyl)-3-(3,5-dimethyl-4-isoxazolyl)-7-((cis-2,6-dimethyl-4-morpholinyl)carbonyl)-9H-carbazole-1-carboxamide was 6.8 mg.

HPLC Retention Time: 1.481. Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Evaluation of Biological Activity

Exemplary compounds were tested for inhibition of BRD4 activity. Experimental procedures and results are provided below.

Cloning, Expression, and Purification of Human Bromodomains for Thermal Shift Assays (TSA)

Recombinant DNA clones encoding bromodomains of human proteins were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions. The non-native amino acids (MGSSHHHHHHSSGETVRFQSM) were immediately followed by bromodomain proteins with the amino acid residue sequences (followed by accessions referenced from and numbered according to the Uniprot Knowledgebase; Uniprot Consortium; www.uniprot.org) as follows:

CECR2(420-543), Q9BXF3-1; FALZ(2917-3037), Q12830-1; GCN5(731-837), Q92830-1; PCAF(715-831), Q92831-1; BRD2(73-194), BRD2(344-455), P25440-1; BRD3(24-144), BRD3(306-416), Q15059-1; BRD4(44-168), BRD4(333-460), BRD4(44-460), 060885-1; BRDT(21-137), Q58F21-1; BAZ1B(1340-1457), Q9UIG0-1; CREBBP (1081-1197), Q92793-1; EP300(1040-1161), Q09472-1; WDR9(1310-1430), Q9N516-1; ATAD2(981-1108), Q6PL18-1; BRD1(556-688), 095696-1; BRD7(129-236), Q9NPI1-1; BRD9(134-239), Q9H8M2-1; BRPF1(626-740), P55201-2; ATAD2B(952-1086), Q9ULI0-1; BAZ2B(2054-2168), Q9UIF8-1; SP140L(400-580), Q9H930-4; SP140 (687-862), Q13342-1; TIF1(896-1014), 015164-1; TRIM28 (619-805), Q13263-1; BRWD3(1295-1443), Q6R145-1; TAF1(1377-1503), TAF1(1501-1635), P21675-1; TAF1L (1402-1522), TAF1L(1523-1654), Q8IZX4-1; ASH1L (2433-2564), Q9NR48-1; PB1(43-156), PB1(178-291), PB1 (388-494), PB1(645-766), PB1(773-917), Q86U86-1; SMARCA2(1367-1511), P51531-1; SMARCA2-2(1367-1493), P51531-2.

The recombinant vectors were transformed into *E. coli* BL21(DE3). The transformed cells were cultured in 1 L terrific broth in 2.5 L Thomson Ultra Yield shaker flasks at 37° C., 230 rpm and, at a cell density of OD600 nm=1.0, were induced with 0.5 mM IPTG and incubated in the shaker at 20° C. for 16-18 hours. The cell pellets were harvested by sedimentation and lysed by sonication in buffer containing 0.1 mg/ml lysozyme. Each sample was clarified by sedimentation, and the supernatant was loaded onto a HisTrap affinity column (GE Healthcare Life Sciences). The column was washed and then eluted with an imidazole gradient. The peak protein fractions containing the bromodomain protein were pooled, concentrated, and the protein was purified further by size exclusion chromatography on a Superdex 200 column (GE Healthcare Life Sciences) equilibrated with the final storage buffer (20 mM Tris-HCl pH 8.0, 200 mM NaCl, 5% glycerol, 2 mM DTT). The SEC peak fractions containing purified protein at 2-5 mg/ml were pooled, and the pool was divided into aliquots, flash frozen in liquid nitrogen, and store at −80° C.

Cloning, Expression, and Purification of Biotinylated Human Bromodomains for TR-FRET Assays Recombinant DNA clones encoding bromodomains of human BRD4 were optimized for *E. coli* expression, chemically synthesized (GenScript, Piscataway N.J.), and inserted into a modified pET28 expression vector to construct tobacco vein mottling virus (TVMV) protease cleavable N-terminal hexahistidine fusions followed by a site specific biotinylation motif recognized by *E. coli* biotin ligase (BirA). The non-native amino acids (MGSSHHHHHHSS-GETVRFQGLNDIFEAQKIEWHEDTGHM) were immediately followed by bromodomain constructs of BRD4 with the amino acid residue sequences (followed by the BRD4 accession referenced from and numbered according to the Uniprot Knowledgebase; Uniprot Consortium; www.uniprot.org) as follows: BRD4(44-168), BRD4(333-460), BRD4 (44-460), BRD4(1-477), 060885-1.

Each of the recombinant vectors were co-transformed into *E. coli* BL21 STAR (DE3) together with a plasmid encoding BirA under chloramphenicol selection. The transformed cells were cultured at 37° C. in 2.5 L Thomson Ultra Yield shaker flasks containing 1 L M9-CAS medium (Teknova) supplemented with 40 μg/ml kanamycin, 35 μg/ml chloramphenicol, and 100 μM biotin. At a cell density corresponding to an OD600 nm=0.6, the cultures were induced with 0.5 mM IPTG and incubated in the shaker for an additional 20 hours at 20° C. The cell pellets were harvested by sedimentation and lysed by sonication in buffer containing 0.1 mg/ml lysozyme. Each sample was clarified by sedimentation, and the supernatant was loaded onto a HisTrap affinity column. The column was washed and then eluted with an imidazole gradient. The peak protein fractions containing the bromodomain protein were pooled and incubated for 18 hours at 4° C. with purified His-TVMV protease (1:15 mass ratio of TVMV:BRD4 protein). The sample was exchanged into low imidazole buffer and passed through a HisTrap column to capture the cleaved His-tag and His-TVMV enzyme. The protein in the HisTrap column flow through was further purified and exchanged into the final storage buffer (PBS pH 7.0, 5% Glycerol, 1 mM DTT) by size exclusion chromatography on a Superdex 200 column. To improve purity, the BRD4(1-477) and BRD4(44-460) proteins were subjected to an additional cation exchange chromatography purification step prior to size exclusion chromatography. Essentially quantitative mono-biotinylation (+226 Da) of each protein was confirmed by electrospray ionization mass spectrometry analysis on the final sample. The purified samples were divided into aliquots, flash frozen in liquid nitrogen, and stored at −80° C.

Time Resolved Fluorescence Resonance Energy Transfer (TR-FRET) Assay

The binding of compounds to bromodomain BRD4 (44-168), BRD4 (333-460), and BRD4 (1-477 or 44-460) was assessed using a time resolved fluorescent resonance energy transfer binding assay (1), that measures the binding of a fluorescently labeled probe molecule to the bromodomain protein. The bromodomain protein, fluorescent probe molecule (either a biotinylated histone peptide or a fluorescently labeled small molecule), and dose-responsed test compound are incubated together to reach thermodynamic equilibrium. In the absence of a test compound, the bromodomain and small molecule are bound, resulting in a high fluorescent signal. In the presence of a sufficient concentration of inhibitor, this intercation is disrupted resulting in a loss of fluorescent resonance energy transfer.

All assay components were dissolved in buffer composition 20 mM Hepes pH 7.5, 150 mM NaCl, 5 mM DTT, 0.005% Tween 20, and 100 ug/ml BSA for BRD4 (1-477 and 44-460). The final concentrations of the bromodomain proteins are 1.6 nM BRD4(44-168), 1 nM BRD4(333-460), and 1 nM BRD4(1-477 or 44-460), and the fluorescent probe molecule is 100 nM, 50 nM, and 7.5 nM respectively. All proteins were biotinylated. A streptavidin labeled with terbium cryptate (Cisbio SA-Tb) was used as detection, and pre-mixed with the bromodomain protein at a final concentration of 0.2 nM. In some instances for BRD4 (44-460), anti-His terbium cryptate was used as a detection. 7.5 nl of dose-responsed test compound or DMSO vehicle (0.0375%) was pre-spotted in a black Corning 384 well plate and 10 ul each of bromodomain/detection reagent and fluorescent small molecule solution were added to the plate, and the reaction incubated for 60 min at room temperature. Plates were then read on EnVision plate reader, (λex=340 nm, acceptor λEm=520 nm, and donor λEm=615 nm, LANCE D400 mirror). Time resolved fluorescence intensity measurements were made at both emissions, and the ratio of acceptor/donor was calculated and used for data analysis. All data was normalized to 16 high vehicle wells and 8 low reference control wells, and then a four parameter curve fit was applied:

$$Y=a+((b-a)/(1+(10x/10c)d)$$

Where 'a' is the minimum, 'b' is the Hill slope, 'c' is the IC50, and 'd' is the maximum. Histone peptide: Purchased from GenScript
H4K5K8K12K16
Biotin-AHA-SGRGK(Ac)GGK(Ac)GLGK(Ac)GGAK(Ac)RHRKV The fluorescently labeled small molecule used was a BRD4 inhibitor known in the art.

1. F. Degorce, A. Card, S. Soh, E. Trinquet, G. P. Knapik and B. Xie, HTRF: A technology tailored for drug discover—a review of theoretical aspects and recent applications. Curent Chemical Genomics (2009) 3, 22-32

Thermal Shift Assay

The effect of compound binding on the thermal stability of the bromodomains was measured using a BioRad CFX real time PCR instrument by monitoring the fluorescence enhancement of an external probe (SYPRO orange) as it binds preferentially to the unfolded protein. The unfolding reactions were carried out in a 384-well plate in a 4 uL volume with 2-8 uM of bromodomain protein, 1-2% (v/v) DMSO in buffer containing 10 mM Hepes, pH 7.4, 500 mM NaCl. SYPRO orange dye was added at a dilution of 1:500. Compound concentrations ranged from 1.6-100 uM. Unfolding reactions were monitored by first equilibrating the instrument at 25° C. for 2.4 sec, followed by ramping the temperature in 0.5° C. increments from 25 to 95° C. with 60 s equilibration prior to a read at each temperature. Excitation and emission filters for the SYPRO orange dye were set to FRET with the excitation range from 450-490 nm and the emission range from 560-580 nm. The midpoint temperature was determined by calculating the inflection point using the second derivative. The observed temperature shifts were recorded as the difference between the midpoint between a reference well containing protein with dmso but no ligand and a well containing protein with compound.

The thermal shift assay is a biophysical technique that compares the change in unfolding transition temperature of a protein obtained in the presence and absence of a ligand (1). Typically, a fluorescent dye is used to monitor the protein unfolding as the protein is heated. During the unfolding process, hydrophobic regions of the protein are exposed, resulting in an increase in the dye binding and an increase in fluorescence intensity. The midpoint of the protein unfolding transition is defined as the Tm. A ligand that binds to the protein causes an increase in the protein thermal stability, thus increasing the Tm, proportionally to both the ligand concentration and its binding affinity.

1. M. W. Pantoliano, E. C. Petrella, J. D. Kwasnoski, V. S. Lobanov, J. Myslik, E. Graf, T. Carver, E. Asel, B. A. Springer, P. Lane, F. R. Salemme, High-density miniaturized thermal shift assays as a general strategy for drug discovery. J. Biomol. Screen 6(2001) 429-440.
2. M. D. Cummings, M. A. Farnum, M. I. Nelen, Universal screening methods and application of ThermoFluor. J. Biomol. Screen 11 (2006) 854-863

MYC HCS Assay

Tumor cells in complete RPMI growth media (Gibco, 11875-085) supplemented with 10% FBS were harvested and plated into 384 black clear-bottom PDL cell culture plates in 30 ul media with 10,000 cells per well. After compound treatment at 37 C for 4 hrs, cells were fixed in 4% Formaldehyde at room temperature for 30 minutes and subsequently permeabilized. After washing and blocking, the plates were then incubated with anti-myc primary antibody 1:1000 (Cell Signaling Technology, 5605) at RT overnight. The following day, cells were washed and blocked before adding secondary antibody Alexa 488 Goat-anti Rabbit 1:2000 (Invitrogen, A11034) at RT in the dark for 1 hr. Cells were subsequently washed and scanned on the Cellomics ArrayScan with 10× objective lens.

MTS Cell Proliferation Assay

Tumor cells were plated at certain seeding densities in 384-well black clear bottom Matrix plates at 40 ul per well and incubated overnight at 37° C. in 5% CO2 before assaying. On the next day, one set of cell plates (T0 plates) were used to determine time zero cell density, and 3-(4,5-dimethylthiazol-2-yl)-5-(3-carboxymethoxyphenyl)-2-(4-sulfophenyl)-2H-tetrazolium from the CellTiter 96 AQueous Non-Radioactive Cell proliferation Kit (Promega, G5440) was added at 4 µl/well into T0 plates followed by incubation at 37° C. in 5% CO2 for three hours. Absorbance at 490 nm was measured on an Envision reader (Perkin Elmer, Boston, Mass.). On the same day, the remaining cell plates (T72 plates) were treated with compounds at 37° C. in 5% CO2. After 72 hours, 4 ul MTS reagents were then added onto those cell plates. The plates were further incubated at 37° C. in 5% CO2 for three hours and the absorbance values at A490 were measured on an Envision reader.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain using tumor fragments obtained from donor mice.

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2-Wt1) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight}=(\text{length}\times \text{width}^2)\div 2$$

Tumor response criteria are expressed by two different parameters: 1) percent tumor growth inhibition (% TGI) or 2) tumor growth delay or log cell kill (LCK). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,

Ct=Median control tumor size at end of treatment

C0=Median control tumor size at treatment initiation

Tt=Median tumor size of treated group at end of treatment

T0=Median tumor size of treated group at treatment initiation

Activity is defined as the achievement of durable tumor growth inhibition of 50% or greater (i.e. TGI≥50%) for a period equivalent to at least 1 tumor volume doubling time and drug treatment must be for a period equivalent to at least 2 tumor volume doubling time.

Tumor response was also expressed in terms of tumor growth delay and expressed as log cell kill (LCK value), defined as the difference in time (days) required for the treated tumors (T) to reach a predetermined target size compared to those of the control group (C):

To estimate tumor cell kill, the tumor volume doubling time was first calculated with the formula:

Log cell kill (LCK)=*T–C*÷(3.32×TVDT)

Where, TVDT=Median time (days) for control tumor weight to reach target size−Median time (days) for control tumor weight to reach half the target size Whenever possible, antitumor activity was determined at a range of dose levels up to the maximum tolerated dose (MTD) which is defined as the dose level immediately below which excessive toxicity (i.e. more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Results of the assays are shown in the Table below. The activity data is based on the use of one of the FRET assays described. Compounds with an IC50 less than 5 µM are shown with (+), compounds with an IC50 less than 0.5 µM are shown with (++) and those with an IC50 less than 0.05 µM are shown with (+++).

| Example # | FRET BRD4 IC$_{50}$ (uM) |
|---|---|
| Example 1 | ++ |
| Example 2 | +++ |
| Example 3 | ++ |
| Example 4 | +++ |
| Example 5 | +++ |
| Example 6 | +++ |
| Example 7 | +++ |
| Example 8 | ++ |
| Example 9 | +++ |
| Example 10 | +++ |
| Example 11 | +++ |
| Example 12 | +++ |
| Example 13 | +++ |
| Example 14 | +++ |
| Example 15 | + |
| Example 16 | +++ |
| Example 17 | +++ |
| Example 18 | +++ |
| Example 19 | ++ |
| Example 20 | +++ |
| Example 21 | +++ |
| Example 22 | +++ |
| Example 23 | +++ |
| Example 24 | +++ |
| Example 25 | +++ |
| Example 26 | +++ |
| Example 27 | ++ |
| Example 28 | ++ |
| Example 29 | ++ |
| Example 30 | ++ |
| Example 31 | ++ |
| Example 32 | + |
| Example 33 | ++ |
| Example 34 | ++ |
| Example 35 | ++ |
| Example 36 | ++ |
| Example 37 | ++ |
| Example 38 | +++ |
| Example 39 | ++ |
| Example 40 | +++ |
| Example 41 | + |
| Example 42 | ++ |
| Example 43 | +++ |
| Example 44 | +++ |
| Example 45 | ++ |
| Example 46 | ++ |
| Example 47 | ++ |
| Example 48 | ++ |
| Example 49 | +++ |
| Example 50 | ++ |
| Example 51 | ++ |
| Example 52 | +++ |
| Example 53 | ++ |
| Example 54 | +++ |
| Example 55 | +++ |
| Example 56 | ++ |
| Example 57 | ++ |
| Example 58 | + |
| Example 59 | + |
| Example 60 | + |
| Example 61 | + |
| Example 62 | + |
| Example 63 | ++ |
| Example 64 | + |
| Example 65 | + |
| Example 66 | + |
| Example 67 | ++ |
| Example 68 | + |
| Example 69 | ++ |
| Example 70 | + |
| Example 71 | +++ |
| Example 72 | ++ |
| Example 73 | ++ |
| Example 74 | ++ |
| Example 75 | ++ |
| Example 76 | +++ |
| Example 77 | ++ |

| Example # | FRET BRD4 IC$_{50}$ (uM) |
|---|---|
| Example 78 | +++ |
| Example 79 | ++ |
| Example 80 | +++ |
| Example 81 | +++ |
| Example 82 | ++ |
| Example 83 | ++ |
| Example 84 | ++ |
| Example 85 | ++ |
| Example 86 | +++ |
| Example 87 | +++ |
| Example 88 | +++ |

What is claimed is:

1. A compound which is 3-(3,5-dimethyl-4-isoxazolyl)-7-(1-piperidinylcarbonyl)-9H-carbazole-1-carboxamide, 3-(3,5-dimethyl-4-isoxazolyl)-7-(4-morpholinylcarbonyl)-9H-carbazole-1-carbonitrile, 3-(3,5-dimethyl-4-isoxazolyl)-1-(5-methyl-1,3-oxazol-2-yl)-7-(4-morpholinylcarbonyl)-9H-carbazole, 3-(3,5-dimethyl-4-isoxazolyl)-7-(4-morpholinylcarbonothioyl)-9H-carbazole-1-carbothioamide, 3-(3,5-dimethyl-4-isoxazolyl)-7-(4-morpholinylcarbonyl)-9H-carbazole-1-carbothioamide, 3-(3,5-dimethyl-4-isoxazolyl)-1-(4-methyl-1,3-thiazol-2-yl)-7-(4-morpholinylcarbonothioyl)-9H-carbazole, 3-(3,5-dimethyl-4-isoxazolyl)-1-(4-methyl-1,3-thiazol-2-yl)-7-(4-morpholinylcarbonyl)-9H-carbazole;

3-(3,5-dimethyl-4-isoxazolyl)-7-(4-morpholinylcarbonyl)-1-(1H-1,2,4-triazol-3-yl)-9H-carbazole, or a pharmaceutically acceptable salt thereof.

2. A pharmaceutical composition which comprises one or more compounds according to claim 1 or a pharmaceutically acceptable salt thereof and one or more pharmaceutically acceptable carriers, diluents or excipients.

3. A combination pharmaceutical product comprising one or more compounds according to claim 1, or a pharmaceutically acceptable salt thereof together with one or more other therapeutically active agents.

4. A compound according to claim 1 or a pharmaceutically acceptable salt thereof for use in the treatment of diseases or conditions for which a bromodomain inhibitor is indicated.

5. A compound or a pharmaceutically acceptable salt thereof for use according to claim 4, wherein the disease or condition is cancer.

* * * * *